(12) United States Patent  
Haines

(10) Patent No.: US 8,740,906 B2
(45) Date of Patent: Jun. 3, 2014

(54) METHOD AND APPARATUS FOR WIREPLASTY BONE RESECTION

(75) Inventor: Timothy G. Haines, LaCrosse, WI (US)

(73) Assignee: Hudson Surgical Design, Inc., Seattle, WA (US)

( * ) Notice: Subject to any disclaimer, the term of this patent is extended or adjusted under 35 U.S.C. 154(b) by 1540 days.

(21) Appl. No.: 12/171,843

(22) Filed: Jul. 11, 2008

(65) Prior Publication Data

US 2009/0082773 A1 Mar. 26, 2009

Related U.S. Application Data

(63) Continuation of application No. 11/049,634, filed on Feb. 2, 2005, now abandoned, which is a continuation of application No. 11/036,584, filed on Jan. 14, 2005, now Pat. No. 7,815,645.

(60) Provisional application No. 60/540,992, filed on Feb. 2, 2004, provisional application No. 60/536,320, filed on Jan. 14, 2004.

(51) Int. Cl.
*A61B 17/00* (2006.01)

(52) U.S. Cl.
USPC .............................................. 606/79

(58) Field of Classification Search
USPC .................. 606/86 R–89, 167–172
See application file for complete search history.

(56) References Cited

U.S. PATENT DOCUMENTS

| 2,697,433 | A | 12/1954 | Zehnder |
| 3,457,922 | A | 7/1969 | Ray |
| 3,739,662 | A | 6/1973 | Windelman et al. |
| 3,748,662 | A | 7/1973 | Helfet |
| 3,774,244 | A | 11/1973 | Walker |
| 3,798,679 | A | 3/1974 | Ewald |
| 3,816,855 | A | 6/1974 | Saleh |
| 3,906,550 | A | 9/1975 | Rostoker |

(Continued)

FOREIGN PATENT DOCUMENTS

| EP | 0104732 | 4/1984 |
| EP | 0121142 | 10/1984 |

(Continued)

OTHER PUBLICATIONS

T.D.V. Cooke et al., *Universal Bone Cutting Device for Precision Knee Replacement Arthroplasty and Osteotomy*, 7 J. Biomed. Eng'g 45, 47, col. 2,11. 52-57 (1985).

(Continued)

*Primary Examiner* — Kevin T Truong
*Assistant Examiner* — Michael Araj
(74) *Attorney, Agent, or Firm* — Patterson Thuente Pedersen, P.A.

(57) ABSTRACT

A cutting tool to be utilized in the resection or removal of bone tissue from patients includes a handle that tensions a wire or cable-like cutting member with a small diameter between at least two features on the handle to present a thin cutting profile. The design of the cutting tool includes features that protect against soft tissue damage and minimize the incision size necessary to utilize the tool. Some embodiments feature details of the cutting tool that interface with a surgical cutting guide system. Other embodiments describe a cutting tool with a selectively changeable length of the cutting profile of the wire cutting member. In one embodiment, the wire cutting member of the cutting tool is energized by mechanical energy in the form of a unidirectional rotation of the cutting member, a mechanical vibration of the cutting member, or an oscillating movement of the wire cutting member.

20 Claims, 77 Drawing Sheets

(56) References Cited

U.S. PATENT DOCUMENTS

| | | |
|---|---|---|
| 3,943,934 A | 3/1976 | Bent |
| 3,953,899 A | 5/1976 | Charnley |
| 3,958,278 A | 5/1976 | Lee |
| 3,977,289 A | 8/1976 | Tuke |
| 4,000,525 A | 1/1977 | Klawitter |
| 4,016,606 A | 4/1977 | Murray |
| 4,069,824 A | 1/1978 | Weinstock |
| 4,178,641 A | 12/1979 | Grundel |
| 4,207,627 A | 6/1980 | Cloutier |
| 4,213,209 A | 7/1980 | Insall |
| 4,249,270 A | 2/1981 | Bahler |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A | 12/1983 | Mains |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,886 A | 2/1986 | Petersen |
| 4,568,348 A | 2/1986 | Johnson et al. |
| 4,584,999 A | 4/1986 | Arnegger |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,703,751 A | 11/1987 | Pohl |
| 4,709,699 A | 12/1987 | Michael |
| 4,711,639 A | 12/1987 | Grundei |
| 4,714,472 A | 12/1987 | Averill |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,808,185 A | 2/1989 | Penenberg |
| 4,822,365 A | 4/1989 | Walker |
| 4,834,758 A | 5/1989 | Lane |
| 4,841,975 A | 6/1989 | Woolson |
| 4,880,429 A | 11/1989 | Stone |
| 4,892,093 A | 1/1990 | Zarnowski |
| 4,893,619 A | 1/1990 | Dale |
| 4,896,663 A | 1/1990 | Vandewalle |
| 4,919,667 A | 4/1990 | Richmond |
| 4,926,847 A | 5/1990 | Luckman |
| 4,935,023 A | 6/1990 | Whiteside |
| 4,936,853 A | 6/1990 | Fabian |
| 4,938,762 A | 7/1990 | Wehrli |
| 4,938,769 A | 7/1990 | Shaw |
| 4,944,757 A | 7/1990 | Martinez |
| 4,950,298 A | 8/1990 | Gustilo |
| 4,952,213 A | 8/1990 | Bowman |
| 4,963,152 A | 10/1990 | Hofmann |
| 4,963,153 A | 10/1990 | Noesberger |
| 4,971,075 A | 11/1990 | Lee |
| 4,979,949 A | 12/1990 | Matsen |
| 4,986,833 A | 1/1991 | Worland |
| 5,002,545 A | 3/1991 | Whiteside |
| 5,002,547 A | 3/1991 | Poggie |
| 5,007,933 A | 4/1991 | Sidebotham |
| 5,007,934 A | 4/1991 | Stone |
| 5,021,056 A | 6/1991 | Hofman |
| 5,021,061 A | 6/1991 | Wevers |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,059,037 A | 10/1991 | Albert |
| 5,062,852 A | 11/1991 | Dorr |
| 5,080,675 A | 1/1992 | Lawes |
| 5,092,869 A | 3/1992 | Waldron |
| 5,098,436 A | 3/1992 | Ferrante |
| 5,100,409 A | 3/1992 | Coates |
| 5,108,398 A | 4/1992 | McQueen |
| 5,112,336 A | 5/1992 | Krevolin |
| 5,116,375 A | 5/1992 | Hofmann |
| 5,122,144 A | 6/1992 | Bert |
| 5,129,907 A | 7/1992 | Heldreth |
| 5,129,909 A | 7/1992 | Sutherland |
| 5,133,758 A | 7/1992 | Hollister |
| 5,133,759 A | 7/1992 | Turner |
| 5,137,536 A | 8/1992 | Koshino |
| 5,147,364 A | 9/1992 | Comparetto |
| 5,147,365 A | 9/1992 | Whitlock |
| 5,147,405 A | 9/1992 | Van Zile |
| 5,176,710 A | 1/1993 | Hahn |
| 5,178,626 A | 1/1993 | Pappas |
| 5,190,547 A | 3/1993 | Barber, Jr. |
| 5,197,944 A | 3/1993 | Steele |
| 5,201,881 A | 4/1993 | Evans |
| 5,203,807 A | 4/1993 | Evans |
| 5,206,023 A | 4/1993 | Hunziker |
| 5,219,362 A | 6/1993 | Tuke |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,432 A | 8/1993 | Matsen |
| 5,236,461 A | 8/1993 | Forte |
| 5,236,875 A | 8/1993 | Trigg |
| 5,250,050 A | 10/1993 | Poggie |
| 5,263,498 A | 11/1993 | Caspari |
| 5,263,956 A | 11/1993 | Nobles |
| 5,269,786 A | 12/1993 | Morgan |
| 5,275,603 A | 1/1994 | Ferrante |
| 5,279,575 A | 1/1994 | Sugarbaker |
| 5,282,803 A | 2/1994 | Lackey |
| 5,282,867 A | 2/1994 | Mikhail |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,326,358 A | 7/1994 | Aubriot |
| 5,330,533 A | 7/1994 | Walker |
| 5,330,534 A | 7/1994 | Herrington |
| 5,342,368 A | 8/1994 | Petersen |
| 5,358,527 A | 10/1994 | Forte |
| 5,358,529 A | 10/1994 | Davidson |
| 5,358,531 A | 10/1994 | Goodfellow |
| 5,364,401 A | 11/1994 | Ferreante |
| 5,364,402 A | 11/1994 | Mumme |
| 5,370,699 A | 12/1994 | Hood |
| 5,370,701 A | 12/1994 | Finn |
| 5,391,170 A | 2/1995 | McGuire |
| 5,397,330 A | 3/1995 | Mikhail |
| 5,405,349 A | 4/1995 | Burkinshaw |
| 5,413,604 A | 5/1995 | Hodge |
| 5,415,663 A | 5/1995 | Luckman |
| 5,417,694 A | 5/1995 | Marik |
| 5,417,695 A | 5/1995 | Axelson, Jr. |
| 5,443,464 A | 8/1995 | Russell |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,480,446 A | 1/1996 | Goodfellow |
| 5,514,136 A | 5/1996 | Richelsoph |
| 5,514,139 A | 5/1996 | Goldstein |
| 5,514,143 A | 5/1996 | Bonutti |
| 5,520,694 A | 5/1996 | Dance |

(56) References Cited

U.S. PATENT DOCUMENTS

| | | |
|---|---|---|
| 5,520,695 A | 5/1996 | Luckman |
| 5,540,695 A | 7/1996 | Levy |
| 5,542,947 A | 8/1996 | Treacy |
| 5,549,683 A | 8/1996 | Bonutti |
| 5,549,684 A | 8/1996 | Amino |
| 5,549,688 A | 8/1996 | Ries |
| 5,551,429 A | 9/1996 | Fitzpatrick |
| 5,562,674 A | 10/1996 | Stalcup |
| 5,569,262 A | 10/1996 | Carney |
| 5,571,100 A | 11/1996 | Goble |
| 5,578,039 A | 11/1996 | Vendrely |
| 5,593,411 A | 1/1997 | Stalcup |
| 5,597,379 A | 1/1997 | Haines |
| 5,601,563 A | 2/1997 | Burke |
| 5,601,566 A | 2/1997 | Dance |
| 5,609,645 A | 3/1997 | Vinciguerra |
| 5,611,802 A | 3/1997 | Samuelson |
| 5,613,969 A | 3/1997 | Jenkins, Jr. |
| 5,628,749 A | 5/1997 | Vendrely |
| 5,639,279 A | 6/1997 | Burkinshaw |
| 5,643,272 A | 7/1997 | Haines |
| 5,643,402 A | 7/1997 | Schmid |
| 5,649,928 A | 7/1997 | Grundei |
| 5,653,714 A | 8/1997 | Dietz |
| 5,658,293 A | 8/1997 | Vanlaningham |
| 5,667,511 A | 9/1997 | Vendrely |
| 5,681,354 A | 10/1997 | Eckhoff |
| 5,682,886 A | 11/1997 | Delp |
| 5,690,632 A | 11/1997 | Schwartz |
| 5,690,635 A | 11/1997 | Matsen, III |
| 5,690,637 A | 11/1997 | Wen |
| 5,697,935 A | 12/1997 | Moran |
| 5,702,458 A | 12/1997 | Burstein |
| 5,723,016 A | 3/1998 | Minns |
| 5,725,530 A | 3/1998 | Popken |
| 5,728,162 A | 3/1998 | Eckhoff |
| 5,755,801 A | 5/1998 | Walker |
| 5,755,803 A | 5/1998 | Haines |
| 5,755,804 A | 5/1998 | Schmotzer |
| 5,766,257 A | 6/1998 | Goodman |
| 5,769,855 A | 6/1998 | Bertin |
| 5,769,899 A | 6/1998 | Schwartz |
| 5,776,200 A | 7/1998 | Johnson |
| 5,782,921 A | 7/1998 | Colleran |
| 5,782,925 A | 7/1998 | Collaz |
| 5,799,055 A | 8/1998 | Peshkin |
| 5,800,552 A | 9/1998 | Forte |
| 5,810,827 A | 9/1998 | Haines |
| 5,824,100 A | 10/1998 | Kester |
| 5,824,102 A | 10/1998 | Buscayret |
| 5,824,105 A | 10/1998 | Ries |
| 5,871,545 A | 2/1999 | Goodfellow |
| 5,871,546 A | 2/1999 | Colleran |
| 5,879,354 A | 3/1999 | Haines |
| 5,879,392 A | 3/1999 | McMinn |
| 5,906,643 A | 5/1999 | Walker |
| 5,908,424 A | 6/1999 | Bertin |
| 5,925,049 A | 7/1999 | Gustilo |
| 5,935,173 A | 8/1999 | Roger |
| 5,944,758 A | 8/1999 | Mansat |
| 5,954,770 A | 9/1999 | Schmotzer |
| 5,980,526 A | 11/1999 | Johnson |
| 5,986,169 A | 11/1999 | Gjunter |
| 5,997,577 A | 12/1999 | Herrington |
| 6,039,764 A | 3/2000 | Pottenger |
| 6,056,754 A | 5/2000 | Haines |
| 6,059,788 A | 5/2000 | Katz |
| 6,068,658 A | 5/2000 | Insall |
| 6,080,195 A | 6/2000 | Colleran |
| 6,083,228 A | 7/2000 | Michelson |
| 6,099,570 A | 8/2000 | Livet |
| 6,110,182 A | 8/2000 | Mowlai-Ashtiani |
| 6,120,543 A | 9/2000 | Meesenburg |
| 6,132,468 A | 10/2000 | Mansmann |
| 6,139,581 A | 10/2000 | Engh |
| 6,165,223 A | 12/2000 | Metzger |
| 6,171,340 B1 | 1/2001 | McDowell |
| 6,195,577 B1 | 2/2001 | Truwit |
| 6,197,064 B1 | 3/2001 | Haines |
| 6,203,576 B1 | 3/2001 | Afriat |
| 6,206,926 B1 | 3/2001 | Pappas |
| 6,210,443 B1 | 4/2001 | Marceaux |
| 6,235,060 B1 | 5/2001 | Meesenburg |
| 6,236,875 B1 | 5/2001 | Bucholz |
| 6,264,697 B1 | 7/2001 | Walker |
| 6,285,902 B1 | 9/2001 | Kienzle |
| 6,306,146 B1 | 10/2001 | Dinkler |
| 6,306,172 B1 | 10/2001 | O'Neil |
| 6,325,828 B1 | 12/2001 | Dennis |
| 6,340,363 B1 | 1/2002 | Bolger |
| 6,342,075 B1 | 1/2002 | MacArthur |
| 6,348,058 B1 | 2/2002 | Melkent |
| 6,361,564 B1 | 3/2002 | Marceaux |
| 6,368,353 B1 | 4/2002 | Arcand |
| 6,375,658 B1 | 4/2002 | Hangody |
| 6,379,388 B1 | 4/2002 | Ensign |
| 6,401,346 B1 | 6/2002 | Roberts |
| 6,406,497 B2 | 6/2002 | Takei |
| 6,413,279 B1 | 7/2002 | Metzger |
| 6,430,434 B1 | 8/2002 | Mittelstadt |
| 6,436,145 B1 | 8/2002 | Miller |
| 6,443,991 B1 | 9/2002 | Running |
| 6,458,128 B1 | 10/2002 | Schulze |
| 6,470,207 B1 | 10/2002 | Simon |
| 6,475,241 B2 | 11/2002 | Pappas |
| 6,477,400 B1 | 11/2002 | Barrick |
| 6,482,409 B1 | 11/2002 | Lobb |
| 6,485,519 B2 | 11/2002 | Meyers |
| 6,491,699 B1 | 12/2002 | Henderson |
| 6,491,726 B2 | 12/2002 | Pappas |
| 6,500,208 B1 | 12/2002 | Metzger |
| 6,506,215 B1 | 1/2003 | Letot |
| 6,520,964 B2 | 2/2003 | Tallarida |
| 6,554,838 B2 | 4/2003 | McGovern |
| 6,575,980 B1 | 6/2003 | Robie |
| 6,579,290 B1 | 6/2003 | Hardcastle |
| 6,595,997 B2 | 7/2003 | Axelson, Jr. et al. |
| 6,620,198 B2 | 9/2003 | Burstein |
| 6,623,526 B1 | 9/2003 | Lloyd |
| 6,645,251 B2 | 11/2003 | Salehi |
| 6,679,917 B2 | 1/2004 | Ek |
| 6,685,711 B2 | 2/2004 | Axelson |
| 6,694,168 B2 | 2/2004 | Traxel |
| 6,694,768 B2 | 2/2004 | Lu |
| 6,695,848 B2 | 2/2004 | Haines |
| 6,697,664 B2 | 2/2004 | Kienzle |
| 6,697,768 B2 | 2/2004 | Yingzhong Lue |
| 6,701,174 B1 | 3/2004 | Krause |
| 6,702,821 B2 | 3/2004 | Bonutti |
| 6,711,432 B1 | 3/2004 | Krause et al. |
| 6,725,080 B2 | 4/2004 | Melkent |
| 6,755,563 B2 | 6/2004 | Wahlig |
| 6,755,835 B2 | 6/2004 | Schultheiss |
| 6,755,864 B1 | 6/2004 | Brack |
| 6,764,516 B2 | 7/2004 | Pappas |
| 6,767,356 B2 | 7/2004 | Tallarida et al. |
| 6,770,097 B2 | 8/2004 | Leclercq |
| 6,773,461 B2 | 8/2004 | Meyers |
| 6,783,550 B2 | 8/2004 | MacArthur |
| 6,796,988 B2 | 9/2004 | Estes |
| 6,827,723 B2 | 12/2004 | Carson |
| 6,858,032 B2 | 2/2005 | Chow |
| 6,875,222 B2 | 4/2005 | Long |
| 6,886,684 B2 | 5/2005 | Hacikyan |
| 6,898,858 B1 | 5/2005 | Spell |
| 6,911,044 B2 | 6/2005 | Fell |
| 6,916,324 B2 | 7/2005 | Sanford |
| 6,916,340 B2 | 7/2005 | Metzger |
| 6,942,627 B2 | 9/2005 | Huitema |
| 6,942,694 B2 | 9/2005 | Liddicoat |
| 7,018,418 B2 | 3/2006 | Amrich |
| 7,029,477 B2 | 4/2006 | Grimm |
| 7,048,741 B2 | 5/2006 | Swanson |
| 7,060,074 B2 | 6/2006 | Rosa |

(56) References Cited

U.S. PATENT DOCUMENTS

| | | |
|---|---|---|
| 7,077,867 B1 | 7/2006 | Pope |
| 7,104,966 B2 | 9/2006 | Shiber |
| 7,104,996 B2 | 9/2006 | Bonutti |
| 7,141,053 B2 | 11/2006 | Rosa |
| 7,172,596 B2 | 2/2007 | Coon |
| 7,175,630 B2 | 2/2007 | Farling |
| 7,241,298 B2 | 7/2007 | Nemec |
| 7,247,157 B2 | 7/2007 | Prager |
| 7,326,252 B2 | 2/2008 | Otto |
| 7,344,541 B2 | 3/2008 | Haines |
| 7,371,240 B2 | 5/2008 | Pinczewski |
| 7,422,605 B2 | 9/2008 | Burstein |
| 7,491,235 B2 | 2/2009 | Fell |
| 7,922,771 B2 | 4/2011 | Otto |
| 2001/0018615 A1 | 8/2001 | Biegun |
| 2001/0044627 A1 | 11/2001 | Justin |
| 2001/0049558 A1 | 12/2001 | Liddicoat |
| 2002/0055784 A1 | 5/2002 | Burstein |
| 2002/0103541 A1 | 8/2002 | Meyers |
| 2002/0107576 A1 | 8/2002 | Meyers |
| 2002/0120340 A1 | 8/2002 | Metzger |
| 2002/0161447 A1 | 10/2002 | Salehi |
| 2002/0183760 A1 | 12/2002 | McGovern |
| 2002/0198531 A1 | 12/2002 | Millard |
| 2003/0028196 A1 | 2/2003 | Bonutti |
| 2003/0055501 A1 | 3/2003 | Fell |
| 2003/0055509 A1 | 3/2003 | McCue |
| 2003/0060882 A1 | 3/2003 | Fell |
| 2003/0060883 A1 | 3/2003 | Fell |
| 2003/0060884 A1 | 3/2003 | Fell |
| 2003/0060885 A1 | 3/2003 | Fell |
| 2003/0069585 A1 | 4/2003 | Axelson |
| 2003/0069591 A1 | 4/2003 | Carson |
| 2003/0093156 A1 | 5/2003 | Metzger |
| 2003/0130665 A1 | 7/2003 | Pinczewski |
| 2003/0158606 A1 | 8/2003 | Coon |
| 2003/0181986 A1 | 9/2003 | Buchholz |
| 2003/0208122 A1 | 11/2003 | Melkent |
| 2003/0212413 A1 | 11/2003 | Wilk |
| 2004/0039396 A1 | 2/2004 | Couture |
| 2004/0044414 A1 | 3/2004 | Nowakowski |
| 2004/0122305 A1 | 6/2004 | Grimm |
| 2004/0152970 A1 | 8/2004 | Hunter |
| 2004/0153066 A1 | 8/2004 | Coon |
| 2004/0199249 A1 | 10/2004 | Fell |
| 2004/0199250 A1 | 10/2004 | Fell |
| 2004/0249467 A1 | 12/2004 | Meyers |
| 2004/0249471 A1 | 12/2004 | Bindseil |
| 2004/0267363 A1 | 12/2004 | Fell |
| 2005/0033424 A1 | 2/2005 | Fell |
| 2005/0149038 A1 | 7/2005 | Haines |
| 2005/0149039 A1 | 7/2005 | Haines |
| 2005/0149040 A1 | 7/2005 | Haines |
| 2005/0171604 A1 | 8/2005 | Michalow |
| 2005/0283251 A1 | 12/2005 | Coon |
| 2006/0015115 A1 | 1/2006 | Haines |
| 2006/0015116 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero |
| 2006/0058882 A1 | 3/2006 | Haines |
| 2007/0078517 A1 | 4/2007 | Engh |
| 2007/0179607 A1 | 8/2007 | Hodorek |
| 2008/0154270 A1 | 6/2008 | Haines |
| 2009/0015109 A1 | 1/2009 | Schuh |
| 2009/0076514 A1 | 3/2009 | Haines |
| 2009/0138018 A1 | 5/2009 | Haines |
| 2010/0100192 A1 | 4/2010 | Haines |
| 2010/0191244 A1 | 7/2010 | White |

FOREIGN PATENT DOCUMENTS

| | | |
|---|---|---|
| EP | 0189253 | 7/1986 |
| EP | 0243109 | 10/1987 |
| EP | 0327249 | 8/1989 |
| EP | 0337901 | 10/1989 |
| EP | 0380451 | 1/1990 |
| EP | 0941719 | 9/1990 |
| EP | 0415837 | 3/1991 |
| EP | 0466659 A2 | 1/1992 |
| EP | 0538153 A1 | 4/1993 |
| EP | 0555003 | 8/1993 |
| EP | 556998 | 8/1993 |
| EP | 0682916 A2 | 11/1995 |
| EP | 0761242 | 3/1997 |
| EP | 0916321 | 5/1999 |
| EP | 0923916 | 6/1999 |
| EP | 0970667 | 1/2000 |
| EP | 0988840 | 3/2000 |
| FR | 2635675 | 3/1990 |
| FR | 2664157 A1 | 1/1992 |
| FR | 2701387 | 8/1994 |
| FR | 2710258 | 3/1995 |
| FR | 2760352 | 9/1998 |
| GB | 1409150 | 10/1975 |
| GB | 2007980 | 7/1982 |
| GB | 2296443 | 7/1996 |
| GB | 2324249 | 10/1998 |
| GB | 2335145 | 9/1999 |
| JP | 02-501806 | 1/1983 |
| JP | 58-209343 | 12/1983 |
| JP | 61-170453 | 8/1986 |
| JP | 62-133948 | 6/1987 |
| JP | 62-254750 | 6/1987 |
| JP | 01-119244 | 5/1989 |
| JP | 01-126957 | 5/1989 |
| JP | 01-209055 | 8/1989 |
| JP | 02-057247 | 2/1990 |
| JP | 02-234756 | 9/1990 |
| JP | 02-234757 | 9/1990 |
| JP | 02-243143 | 9/1990 |
| JP | 239861 | 9/1990 |
| JP | 02-246971 | 10/1990 |
| JP | 2002/274214 | 11/1990 |
| JP | 03-032663 | 2/1991 |
| JP | 04-297254 | 10/1992 |
| JP | 04-361746 | 12/1992 |
| JP | 05-003880 | 1/1993 |
| JP | 05-502814 | 5/1993 |
| JP | 5-41510 | 6/1993 |
| JP | 05-269140 | 10/1993 |
| JP | 05-277130 | 10/1993 |
| JP | 06-08033 | 1/1994 |
| JP | 06-38971 | 2/1994 |
| JP | 6-217984 | 8/1994 |
| JP | 06-233775 | 8/1994 |
| JP | 06-237941 | 8/1994 |
| JP | 7-501966 | 3/1995 |
| JP | 7-116185 | 5/1995 |
| JP | 7-136200 | 5/1995 |
| RU | 2121319 | 11/1998 |
| SE | 382155 | 1/1976 |
| SU | 577020 T | 10/1977 |
| WO | WO 81/03122 | 11/1981 |
| WO | WO 91/00061 | 1/1991 |
| WO | WO 91/10408 | 7/1991 |
| WO | WO 93/22990 | 11/1993 |
| WO | WO 93/25157 | 12/1993 |
| WO | WO 94/05212 | 3/1994 |
| WO | WO 94/08528 | 4/1994 |
| WO | WO 94/09730 | 5/1994 |
| WO | WO 94/14366 | 7/1994 |
| WO | WO 94/22397 | 10/1994 |
| WO | WO96/01588 | 1/1996 |
| WO | WO96/07361 A1 | 3/1996 |
| WO | WO 96/24295 | 8/1996 |
| WO | WO 97/05827 | 2/1997 |
| WO | WO97/29703 A1 | 8/1997 |
| WO | WO97/29704 A1 | 8/1997 |

(56) References Cited

FOREIGN PATENT DOCUMENTS

| WO | WO 9820817 | 5/1998 |
|---|---|---|
| WO | WO 99/27872 | 6/1999 |
| WO | WO 99/30649 | 6/1999 |
| WO | WO 01/13825 | 3/2001 |
| WO | WO02/34310 | 5/2002 |
| WO | WO2004/069036 | 8/2004 |
| WO | WO2004/070580 | 8/2004 |
| WO | WO2004/100758 | 11/2004 |
| WO | WO2004/100839 | 11/2004 |

OTHER PUBLICATIONS

E. Marlowe Goble and Daniel F. Justin, *Minimally invasive total knee replacement: principles and technique*, Orthop. Clin. N. Am. 35 (2004) 235-245.

Whiteside Ortholoc Total Knee System: Surgical Procedure, Dow Corning Wright, pp. WMT000001-WMT000040, Jun. 1985.

Zimmer, Insall/Burstein II, *Constrained Condylar: Modular Knee System*, 35 pages, copyright 1989.

File History for U.S. Appl. No. 12/187,210, filed Aug. 6, 2008.

File History for U.S. Appl. No. 11/075,842, filed Mar. 8, 2005.

File History for U.S. Appl. No. 11/075,828, filed Mar. 8, 2005.

File History for U.S. Appl. No. 11/075,836, filed Mar. 8, 2005.

U.S. Appl. No. 11/036,584, Inventor: Haines, filed Jan. 14, 2005.

File History for U.S. Appl. No. 11/075,840, filed Mar. 8, 2005.

U.S. Appl. No. 11/075,552, Inventor: Haines, filed Mar. 8, 2005.

U.S. Appl. No. 11/825,857, Inventor: Haines, filed Jul. 9, 2007.

File History for U.S. Appl. No. 11/049,634, filed Feb. 5, 2005.

File History for U.S. Appl. No. 11/074,599, filed Mar. 8, 2005.

File History for U.S. Appl. No. 11/075,553, filed Mar. 8, 2005.

Zimmer, The Miller/Galante Advantage: Total Knee System, pp. ZH000156953-ZH000156968.

Whiteside Ortholoc Total Knee System, Dow Coming Wright, pp. ZH000109679-ZH000109690.

Zimmer, Insall/Burnstein II, *Modular Knee System*, Surgical Technique, pp. ZH000109691-ZH000109710.

Freeman Samuelson, *Total Knee System*, published by Biomet, Inc., 1994 ("Biomet Brochure") (Attached as Exhibit F).

Freeman, Mark II *Total Knee Replacement System*, published 1985 (Attached as Exhibit G).

Protek F/S Modular Total Knee Replacement System, pp. 1-57, published by Protek in Jan. 1991 (Attached as Exhibit H).

*Low Contact Stress Meniscal Bearing Unicompartmental Knee Replacement: Long-Term Evaluation of Cemented and Cementless Results*, Journal of Orthopaedic Rheumatology (presented at the 57th Annual American Academy of Orthopaedic Surgeons Meetings, New Orleans, LA, Feb. 11, 1990), Bates No. DEP00004096-DEP00004107.

N.J. Unicompartmental Knee, Dated Sep. 15, 1989, Bates No. DEP00004108-DEP00004116.

Buechel, Frederick F., *NJ LCS Unicompartmental Knee System with Porocoat*, dated Oct. 24, 1994, Bates No. DEPO00004117-DEP00004130.

Buechel, Frederick F. *NJ LCS Unicompartmental Knee System with Porocoat*, 1994, Bates No. DEP00004131-DEP00004141.

Buechel, Frederick F. *NJ LCS Unicompartmental Knee System with Porocoat*, 1994, Bates No. DEP00004142-DEP00004152.

Engh, et al., *The AMK Total Knee System, Design Rationale and Surgical Procedure*, dated 1989, Bates No. DEP00004153-DEP00004201.

*Advertising Proteck Mark II PCR Total Knee Replacement System*, Journal of Bone and Joint Surgery, 1987, Bates No. DEP00004202-DEP00004230.

Protek, *Parts Brochure for Mark II Protek*,1987, Bates No. DEP00004231-DEP00004235.

Chapman, Michael W., *Operative Orthopaedics*, vol. 1, Published by J.B. Lipponcott Co., Philadelphia, dated 1988, Bates No. DEP00004236-DEP00004247.

American Academy of Orthopaedic Surgeons, *Flyer from 57th Annual American Academy of Orthopaedic Surgeons Meeting*, Feb. 13, 1990, Bates No. DEP00004248-DEP00004251.

Crossett et al., *AMK Congruency Instrument System, Surgical Technique*, dated 1997, Bates No. DEP00004252-DEP00004267.

Engh et al., *AMK Surgical Technique*, Bates No. DEP00004268-DEP00004298, dated 1989.

Engh et al., *AMK Surgical Technique*, Bates No. DEP00004299-DEP0004329, dated 1989.

Crenshaw, A.H., *Campbell's Operative Orthopaedics*, 4th Edition, vol. 1, Bates No. DEP00004330-DEP00004333, dated 1963.

Howmedica, *Duraconcept, Design Concepts of the Duracon Total Knee System*, Bates No. DEP00004337-DEP00004337, dated 1993.

Freeman et al., *Total Knee System*, Bates No. DEP00004350-DEP00004361, Published prior to Jun. 7, 1994.

Freeman et al., *F/S Modular Total Knee Replacement System-SICOT*, 90 Edition, Bates No. DEP00004362-DEP00004373, dated 1990.

Buechel, Frederick F., *Howmedica Product Catalog*, Bates No. DEP00004374-DEP00004375, dated 1994.

Massarella, Antony, *Interax Bulletin*, No. 6, *Tibial Intramedullary Alignment Surgical Technique*, Bates No. DEP00004387-DEP00004390, dated Feb. 23, 1994.

Desjardins et al., *Interax Operative Technique*, Bates No. DEP00004391-DEP00004411, dated 1994.

Desjardins et al., *Interax Total Knee Operative Technique: Monogram Total Knee Instruments*, Bates No. DEP00004412-DEP00004432, dated 1993.

Howmedica, *Interax Tibial IM*, Bates No. DEP00004433-DEP00004433, dated 1994.

Depuy, *LCS UNI PMA Data from Fda Website*, Bates No. DEP00004434-DEP00004434, dated 1991.

Briard et al., *LCS Uni Unicompartmental Knee System with Porocoat*, Bates No. DEP00004452-DEP00004462, dated 1991.

Freeman et al., *Mark II Total Knee Replacement System*, Bates No. DEP00004463-DEP00004492, dated 1985.

Buechel, Frederick F., *NJ LCS Unicompartmental Knee System with Porocoat*, Bates No. DEP00004493-DEP00004503, dated 1994.

Chapman, Michael W. *Operative Orthopaedics*, vol. 3, 2nd Edition, Published by J.B. Lipponcott Co., Bates No. DEP00004504-DEP00004508, dated 1993.

Biomet, *Oxford Meniscal Knee Phase II Unicompartmental Replacement*, Bates No. DEP00004509-DEP00004515, Published prior to Jun. 7, 1994.

Scott et al., *P.F.C. Sigma Unicompartmental Knee System*, Bates No. DEP00004531-DEP00004539, dated 1998.

Freeman et al., *F/S Modular Total Knee Replacement System*, Bates No. DEP00004540-DEP00004596, dated 1990.

Broughton et al., *Unicompartmental Replacement and High Tibial Osteotomy for Osteoarthritis of the Knee*, Journal of Bone and Joint Surgery, vol. 68-B, No. 3, May 1, 1986, pp. 447-452, Bates No. DEP00004752-DEP00004763.

Scott et al., *Unicompartmental and High Tibial Osteotomy for Osteoarthritis of the Knee*, Journal of Bone and Joint Surgery, vol. 63-A, No. 4, Apr. 1, 1981, Bates No. DEP00004764-DEP00004775.

Thornhill, Thomas S., *Unicompartmental Knee Arthroplasty Clinical Orthopaedics and Related Research*, No. 205, Apr. 1, 1986, pp. 121-131, Bates No. DEP00004776-DEP00004791.

Forst et al., *A Special jg for Tibial Resection for the Implantation of GSB-Knee-Prostheses in Problematic cases*, pp. 162-166, dated Jun. 1, 1984, Bates No. DEP00004838-DEP00004842.

Ingillis et al., *Revision Total Knee Replacement Techniques in Orthopedics*, dated Apr. 1, 1990, Bates No. DEP00005583-DEP00005592.

Uvehammer et al., "In Vivo Kinematics of Total Knee Arthroplasty: Concave Versus Posterior-Stabilised Tibial Joint Surface", vol. 82-B, No. 4, May 2000, pp. 499-505.

U.S. Appl. No. 12/638,692, filed Dec. 15, 2009, Haines.

WIRE HANDLE RETAINING CLIPS - ASSISTS IN MAINTAINING THE HANDLE IN PROPER RELATION AND ENGAGEMENT TO A CUTTING GUIDE, IF USED.

Application No.: 12/171,843
Office Action dated 04/03/12
Replacement Sheet

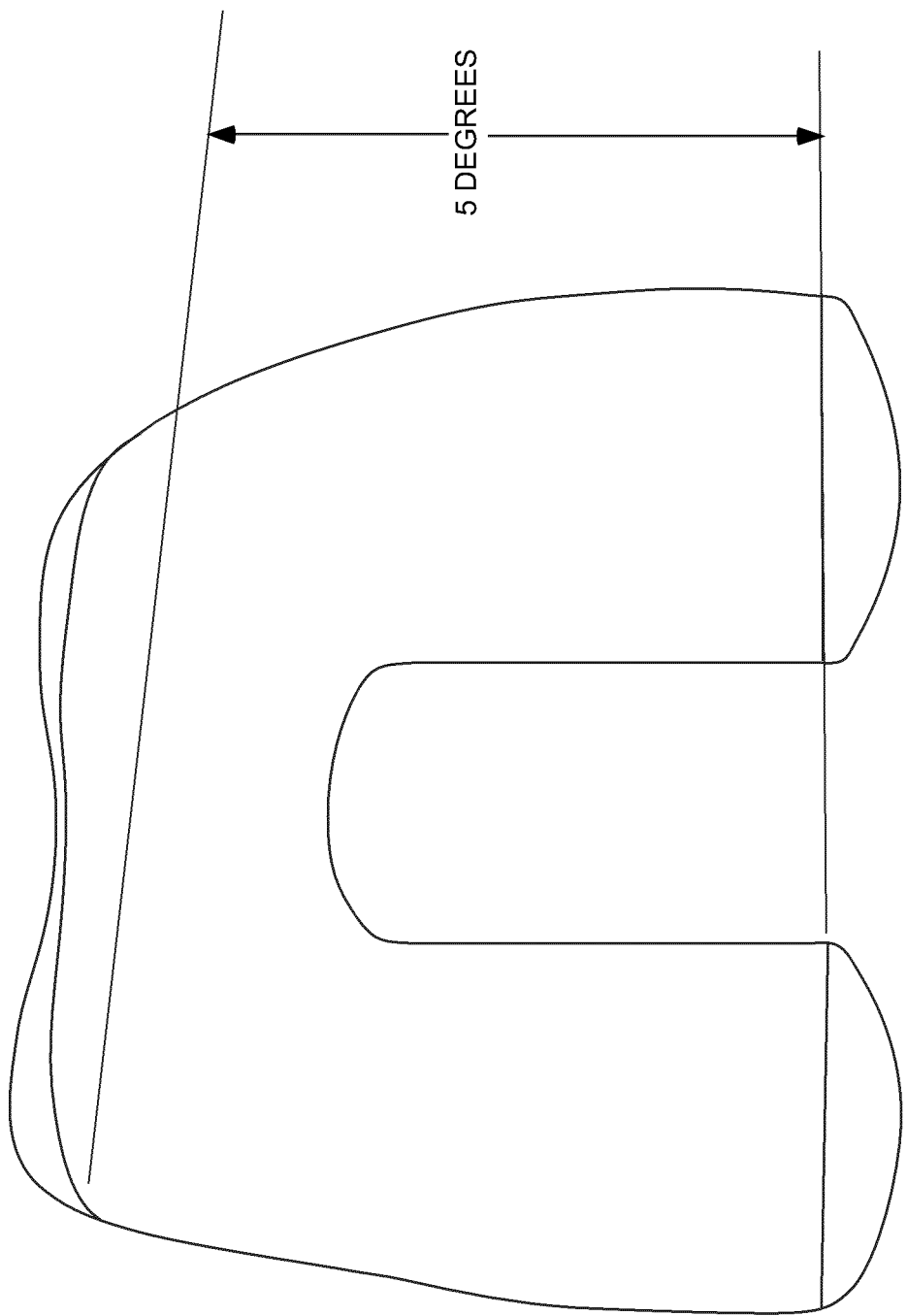

METHOD AND APPARATUS FOR WIREPLASTY BONE RESECTION

RELATED APPLICATION

This application is a continuation of application Ser. No. 11/049,634 filed Feb. 2, 2005, which claims the benefit of U.S. Provisional Application No. 60/540,992 filed Feb. 2, 2004, and claims priority to continuation application Ser. No. 11/036,584 filed Jan. 14, 2005, which claims the benefit of U.S. Provisional Application No. 60/536,320 filed Jan. 14, 2004, each of which is hereby fully incorporated herein by reference.

BACKGROUND OF THE INVENTION

1. Field of the Invention

This invention generally relates to methods and apparatus for bone resection to allow for the interconnection or attachment of various prosthetic devices with respect to the patient. More particularly, the present invention relates to the use of a wireplasty bone resection technique in which wires or cables act as bone cutting tools.

2. Background Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, for example, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating saw blade based resection systems has been the standard in total knee replacement and other forms of bone resection for over 30 years. Unfortunately, present approaches to using such planar saw blade instrumentation systems all possess certain limitations and liabilities.

Perhaps the most critical factor in the clinical success of any bone resection for the purpose of creating an implant surface on the bone is the accuracy of the implant's placement. This can be described by the degrees of freedom associated with each implant. In the case of a total knee arthroplasty (TKA), for example, for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of 1/8 or 3/16 inch diameter pin or drill placement in the anterior or distal faces of the femur for placement of cutting guides. In the case of posterior referencing systems for TKA, the distal resection cutting guide is positioned by drilling two long drill bits into the anterior cortex along the longitudinal axis of the bone. As these long drills contact the oblique surface of the femur they very often deflect, following the path of least resistance into the bone. As the alignment guides are disconnected from these cutting guides, the drill pins will "spring" to whatever position was dictated by their deflected course thus changing their designated, desired alignment to something less predictable and/or desirable. This kind of error is further compounded by the "tolerance stacking," inherent in the use of multiple alignment guides and cutting guides.

Another error inherent in these systems further adding to mal-alignment is deflection of the oscillating saw blade during the cutting process. The use of an oscillating saw blade is very skill intensive as the blade will also follow the path of least resistance through the bone and deflect in a manner creating variations in the cut surfaces which further contribute to prosthesis mal-alignment as well as poor fit between the prosthesis and the resection surfaces. Despite the fact that the oscillating saw has been used in TKA and other bone resection procedures for more than 30 years, there are still reports of incidences where poor cuts result in significant gaps in the fit between the implant and the bone. The safety of these saws is also questionable as minor incidences of misuse can result in serious harm and disability.

While oscillating saws have been the preferred tools for performing bone resections as part of an implantation procedure, other forms of bone saws and cutting instruments have also been used to cut bones. Generally, the problems of precision, accuracy and safety of these other cutting instruments are even greater than with an oscillating saw. U.S. Pat. No. 5,725,530 describes a planar surgical saw that utilizes a dual chain saw arrangement with guards along the outer sides of the chain saw blades. A surgeon's gigli saw, for example, has a cutting wire with a handle on each end that is wrapped around a bone to be cut. The surgeon alternates pulling each handle to run the cutting wire back and forth around the bone to cut the bone. U.S. Pat. No. 4,709,699 describes an improved cutting wire for a surgeon's gigli saw. U.S. Pat. No. 6,368,353 describes the use of a gigli saw for resecting the neck of the humerous bone as part of an implant procedure for a shoulder prosthesis. Although conventional chain saws and gigli saws can be very efficient general purpose cutting tools, these saws have little ability to be guided and aligned so as to make the precise and accurate resection cuts required for effective implants.

Improvements in the precision, accuracy, and safety of tools for resecting bone surfaces are desired in order to increase the efficacy of orthopedic procedures and enable the surgeon to better achieve the benefits of a standard, less invasive, and more efficacious joint reconstruction.

SUMMARY OF THE INVENTION

The present invention provides for a cutting tool to be utilized in the resection or removal of bone tissue from patients. The cutting tool includes a handle that tensions a wire or cable-like cutting member with a small diameter between at least two stationary points on the handle to present a thin cutting profile. The design of the cutting tool includes features that protect against soft tissue damage and minimize the incision size necessary to utilize the tool. Some embodiments feature details of the cutting tool that interface with a surgical cutting guide system. Other embodiments describe a cutting tool with a selectively changeable length of the cutting profile of the wire cutting member. In one embodiment, the wire cutting member of the cutting tool is energized by mechanical energy in the form of a unidirectional rotation of the cutting member, a mechanical vibration of the cutting member, or an oscillating movement of the wire cutting member. In another embodiment, a very small diameter wire is used to permit manual manipulation of the cutting tool, but still provide sufficient force to effect cutting of the bone.

It is an often repeated rule of thumb for orthopedic surgeons that a "Well placed, but poorly designed implant will perform well clinically, while a poorly placed, well designed implant will perform poorly clinically." The present invention provides a method and apparatus for reducing implant placement errors in order to create more reproducible, consistently excellent clinical results in a manner that is less dependent upon the manual skill of the surgeon creating a resected surface. Importantly, some of the embodiments of the present invention demonstrate the ability to be inserted into small incisions and yet extend the cutting surfaces of the tool significantly across the bone to be cut beneath the soft tissues of the joint, thus cutting bone surfaces that are not readily visible to the surgeon during the procedure.

It should be clear that applications of the present invention is not limited to Total Knee Arthroplasty, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), Bunionectomy, ACL or PCL reconstruction, and many others. In essence, any application where an inexpensive, accurate, and relatively precise system is required or desired for a bone resection is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

Other important objects and features of the invention will be apparent from the following detailed description of the invention taken in connection with the accompanying drawings in which:

FIGS. 3-77 show various depictions of the placement and use of wire cutting tools and operation with or without a cutting guide in accordance with alternate embodiments of the present invention.

DETAILED DESCRIPTION OF THE PREFERRED EMBODIMENTS

Figure 1:
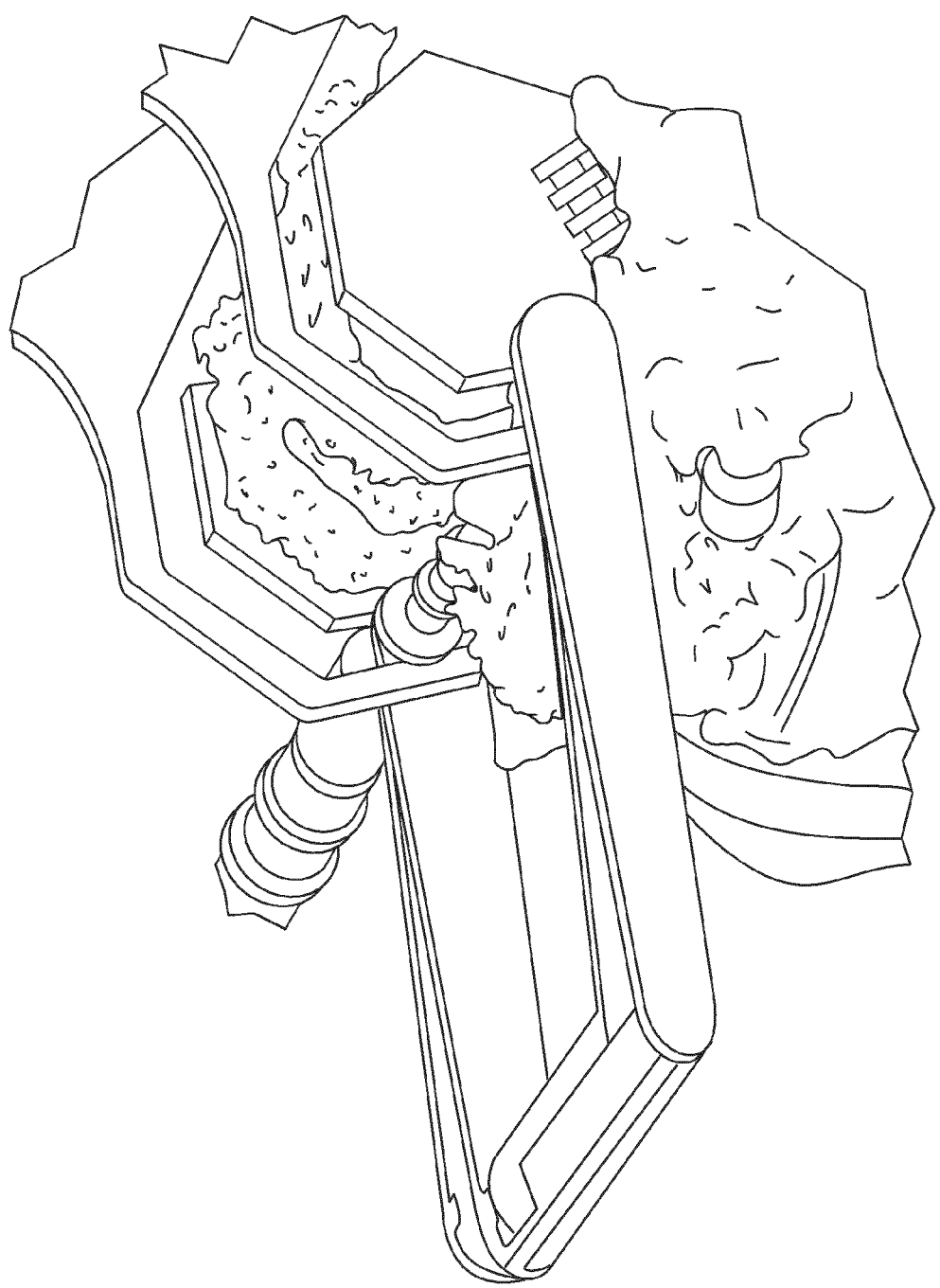
FIGS. 1 and 2 are pictorial representations of a prior art femoral resection device being used in an open approach TKA and a 19$^{th}$ Century Gigli Saw, respectively, of the prior art.
Figure 41:
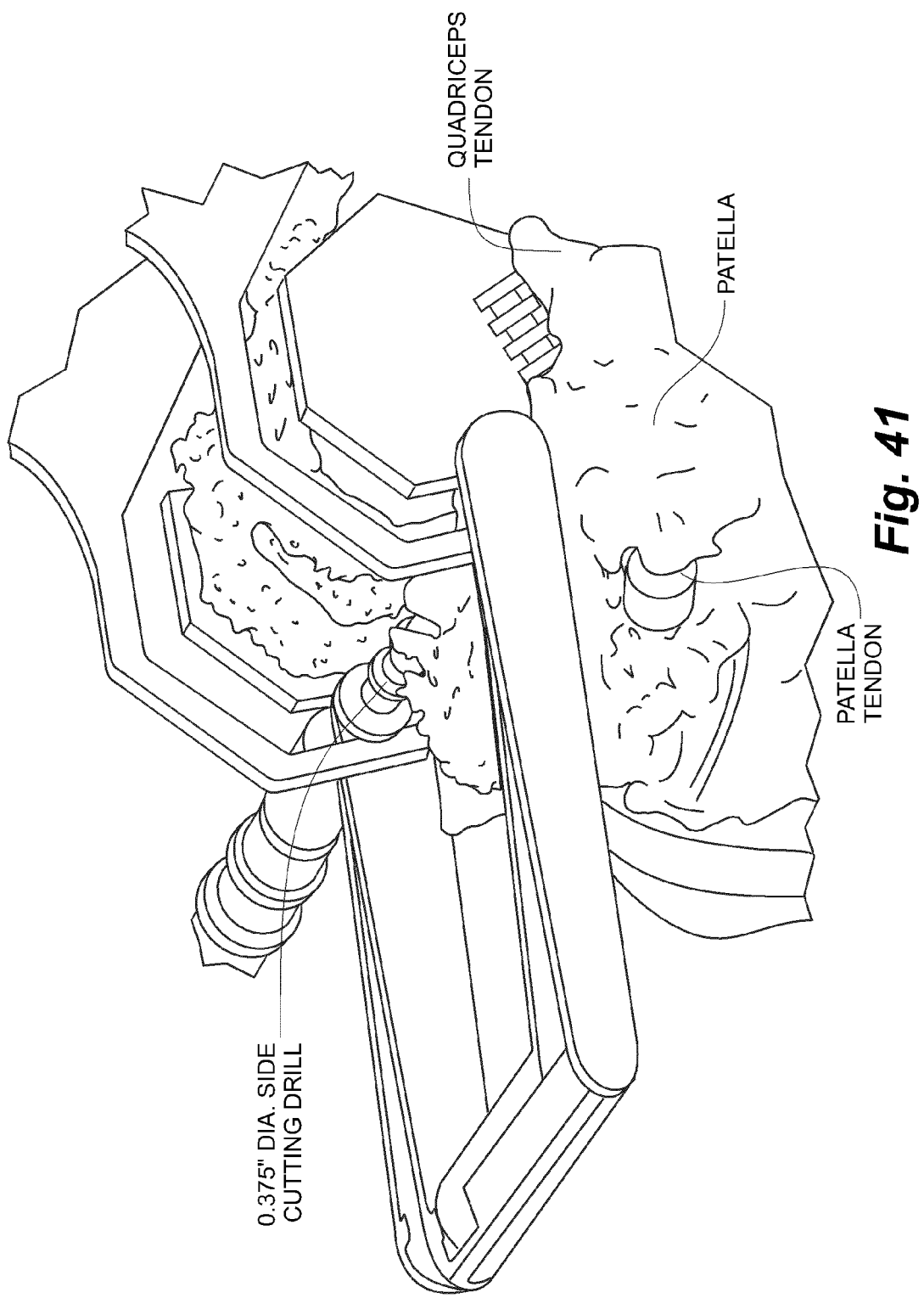

FIGS. 1 and 41 shows a Profile Based Resection (PBR) type cutting guide in conjunction with a side cutting drill in action. This will be recognized as an embodiment of the inventions of U.S. Pat. No. 5,810,827. The basic components are the side cutting drill, the PBR guide, the guide handle, and fixation features of the cutting guide, which in this case are cannulated screws or drill guides and 0.125 inch drill pins. The PBR guide possesses at least one plate to which the guide handle is engaged during cutting. A drawback about this particular design or embodiment of the PBR technology is that, in the hands of an average surgeon, it required an incision length of at least 6 inches in order to be attached to the femur and utilized to resect or cut bone. It is an object of some of the embodiments of the present invention to provide for improvements upon this design enabling it to be used in a manner that is less invasive or minimally invasive while maintaining the outstanding reproducibility provided by the PBR technology.

Figure 2:
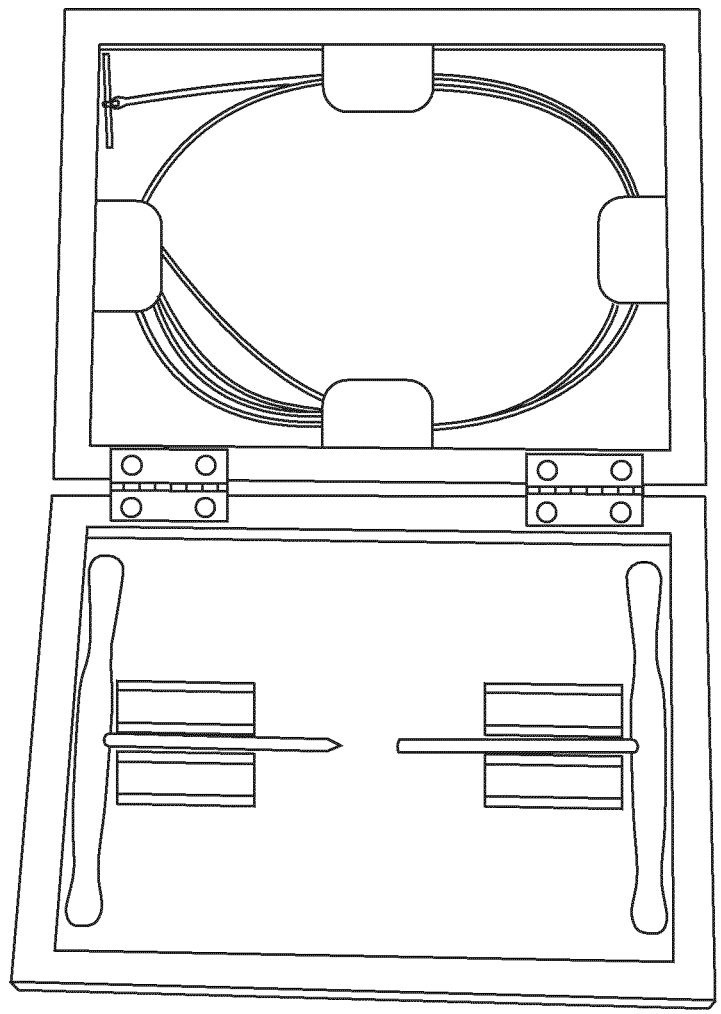

FIG. 2 shows an antique gigli saw surgical kit. It is noted that the date of manufacture of this kit was 1896. The top of the box shown contains the gigli saw, while the bottom of the box shows the handles used to manipulate the gigli saw in a back-and-forth sawing motion by alternating pulling on each handle.

The present invention provides for a cutting tool to be utilized in the resection or removal of bone tissue from patients. The cutting tool includes a handle that tensions a wire or cable-like cutting member with a small diameter between at least two stationary points on the handle to present a thin cutting profile. The design of the cutting tool includes features that protect against soft tissue damage and minimize the incision size necessary to utilize the tool. Some embodiments feature details of the cutting tool that interface with a surgical cutting guide. Other embodiments describe a cutting tool with a selectively changeable length of the wire cutting member. In one embodiment, the wire cutting member of the cutting tool is energized by mechanical energy in the form of a unidirectional rotation of the cutting member, a mechanical vibration of the cutting member, or an oscillating movement of the wire cutting member. In another embodiment, a very small diameter wire is used to permit manual manipulation of the cutting tool, but still provide sufficient force to effect cutting of the bone.

Figure 5:
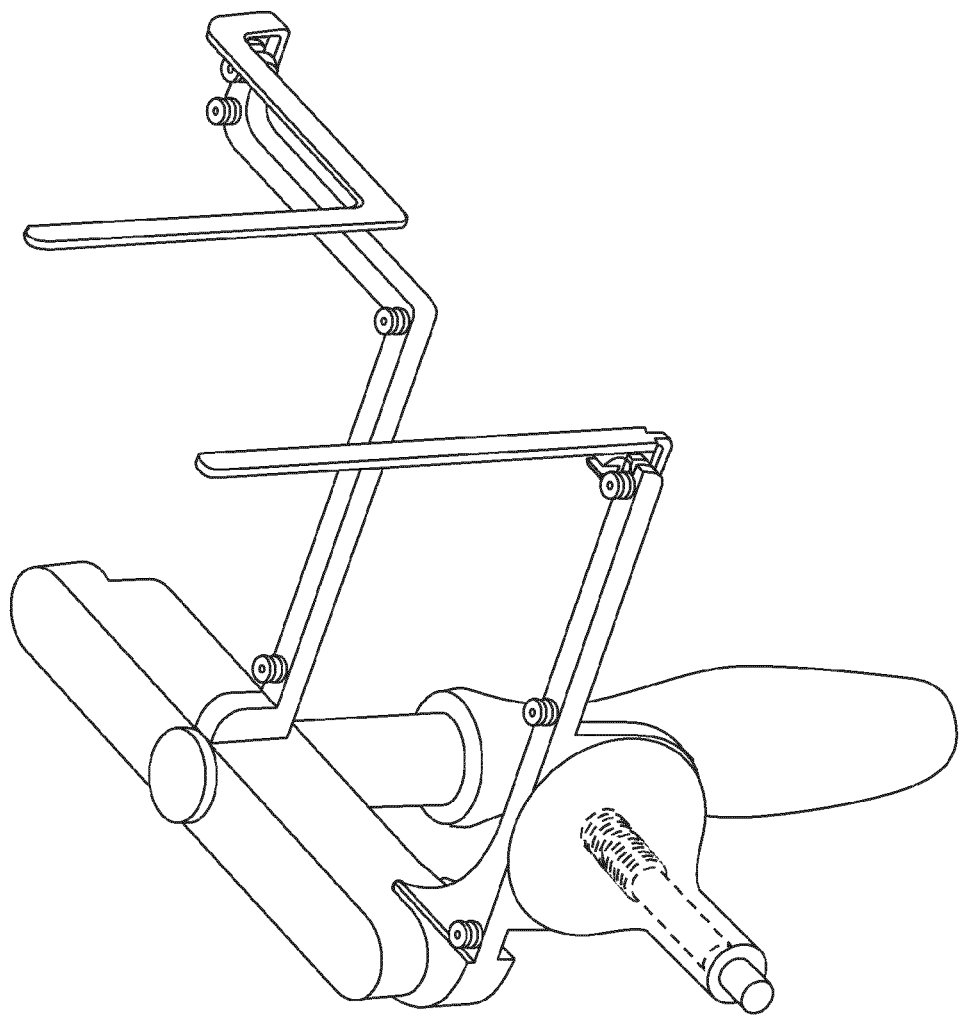
Figure 6:
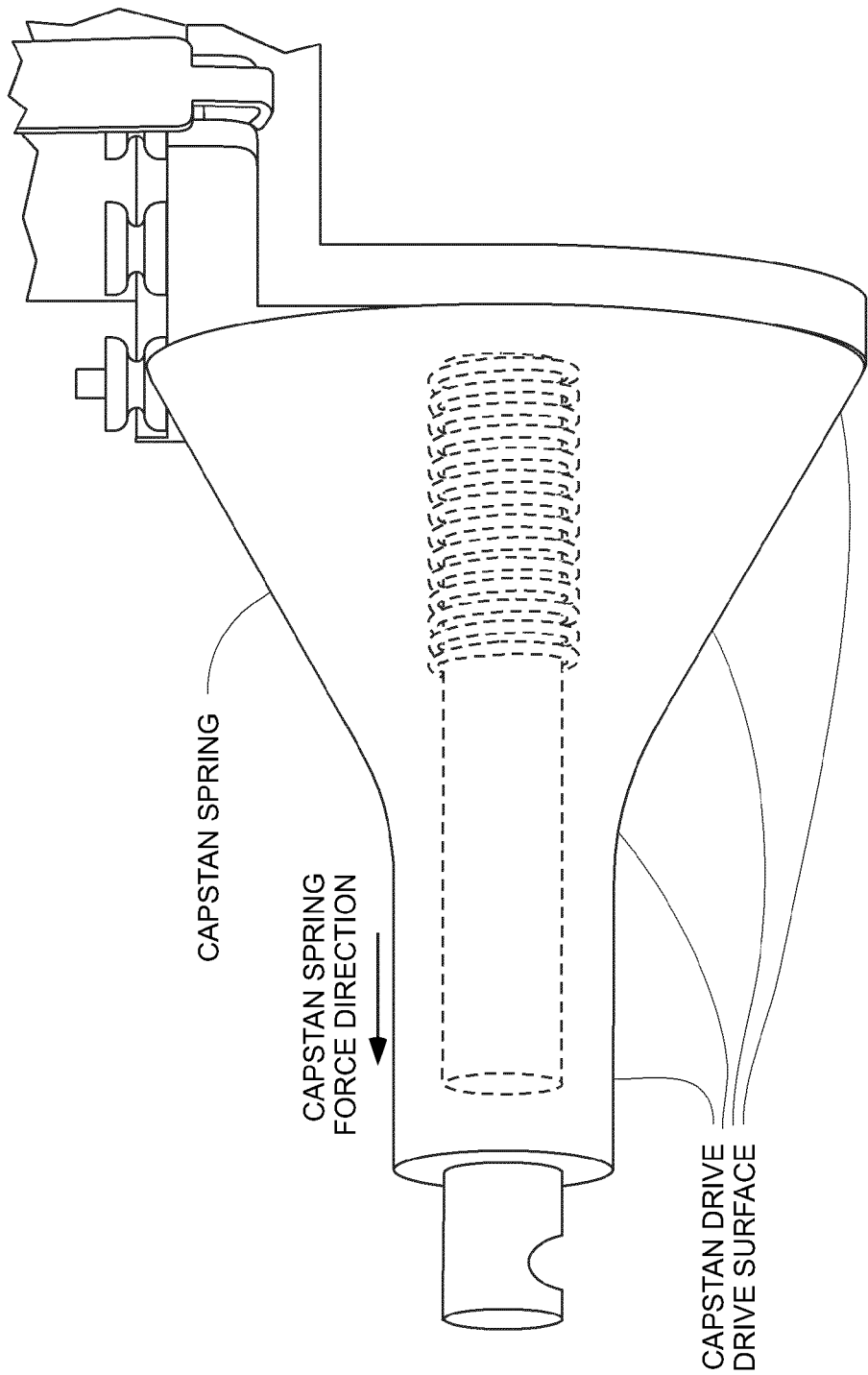
Figure 7:
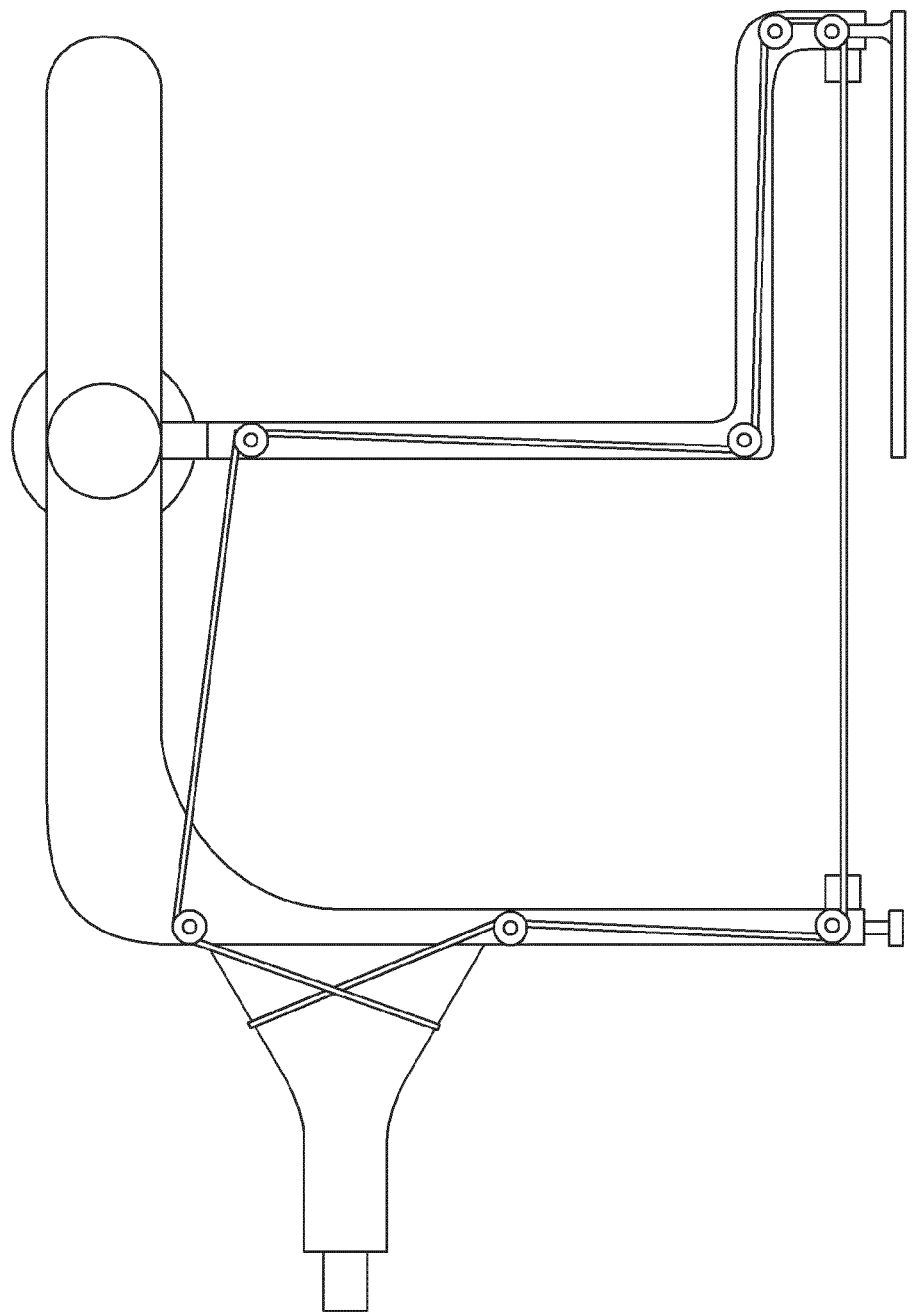
Figure 8:
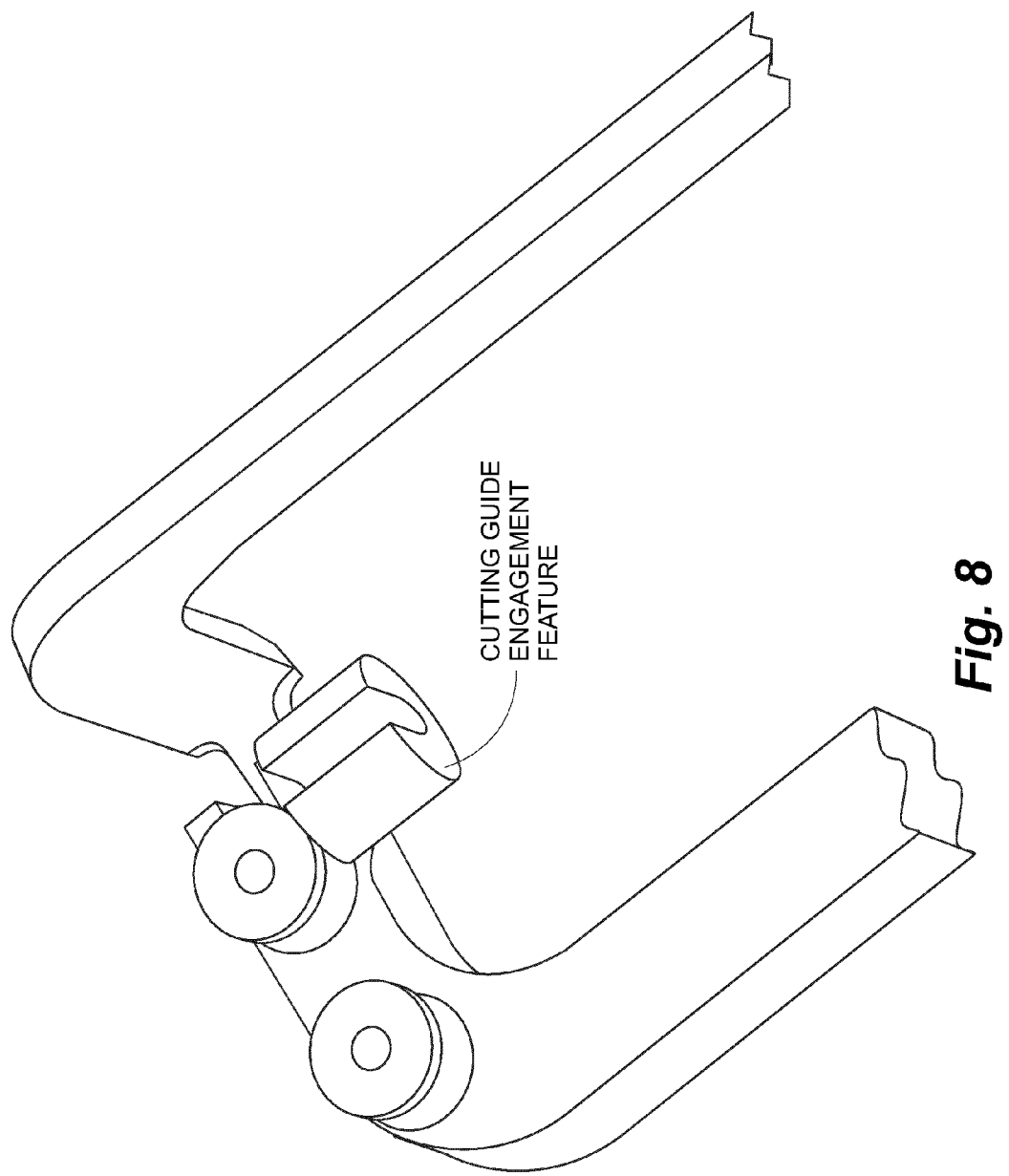
Figure 66:
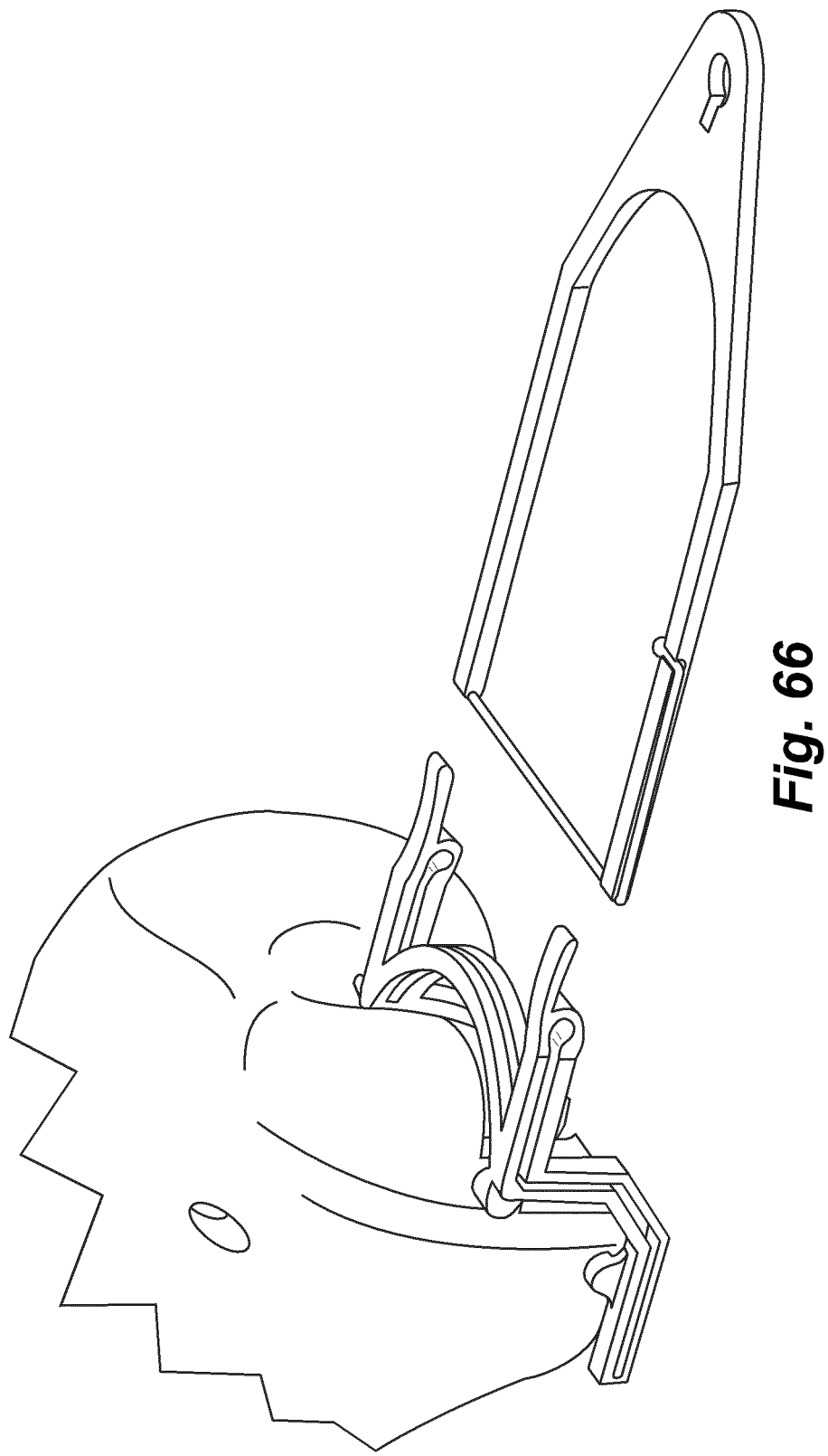

It should be noted that the manner in which mechanical energy is transmitted to these wire cutting members is shown as being a rotary input, or electrical or pneumatic drill. There are many variations which may impart improved performance in different ways. For instance, the wire cutting tool shown in FIG. 5 is driven in a fashion reminiscent of a band saw, but the wire could be a semi-static structure suspended between the two opposing handle arms where ultrasonic energy is imparted to the wire. The advantage to ultrasonic cutting methods is that the 'waveform' or 'waveforms' may be tuned (different frequencies, amplitudes, and waveforms) such that the tool slices through bone like a hot knife through butter, but is incapable or highly resistant to harming soft tissue it contacts. In such an ultrasonic embodiment, the cutting tool preferably has different settings that are selectable by the surgeon depending on the material he wishes to cut. The mechanical energy can also be imparted to the wire cutting elements by commonly used oscillating saw drivers. FIG. 66 shows a simple embodiment of the present invention relying on this form of driver. It is interesting to note that this embodiment enables the cutting tool, quite uniquely, to easily create curved surfaces in addition to the continuous, but rectilinear surfaces shown. All that is required is to make the guide slots or surfaces correspondingly curved.

Another embodiment of the present invention does not incorporate mechanical energy applied to the wire cutting member. In this embodiment, the wire cutting member has an extremely small in diameter or thickness, ideally as small as a single molecule in thickness, and the wire cutting member is placed under tension. The manual cutting operation of this embodiment is similar to that of a cheese slicer. In essence, the surgeon, by pulling on the handle, imparts sufficient force to the wire that, given its extremely small thickness, results in exceedingly high contact pressures, thus cutting the bone. While molecular thickness wires are ideal for this embodiment, such as wires based on carbon nanotubes, wire thicknesses of 0.005 mm to 0.5 mm are more practicable.

It will also be recognized that numerous kinds of wires or cables, such as single stranded or multi-stranded wires, or wires with teeth or protrusion features or relief features along the wire can be used as the wire cutting member in accordance with the various embodiments of the present invention. In the capstan embodiment of the present invention that will be described, for example, it is preferred that a wire member without teeth or protrusion members capable of abrading the capstan be used to minimize wear to the capstan drive. Preferably, the effective outer diameter of the wire cutting member is no greater than about 4 mm and more preferably less than about 0.5 mm. The wire cutting member may be formed of metal or a high tensile strength multi or mono-filament, such as Kevlar® fiber. Alternatively, the wire cutting member may be formed of a flexible substrate core adhesively coated with abrasive media. Still another embodiment provides for wires spun from Liquidmetal® alloys. Preferably, the wire cutting member is disposable and is used for a single patient procedure and is then replaced. Alternatively, the wire cutting member can be made sterilizable and reusable.

One important benefit provided by the low thickness wire cutter embodiments of the present invention is the fact that they will cut or morselize a very small total volume of bone, thus minimizing difficulty in removal of the debris prior to finishing the procedure. In Total Joint Replacement this is especially important as morselized bone debris remaining in the joint may lead to premature failure of the bearing components of the implant via the mechanisms of third body wear.

Figure 4:
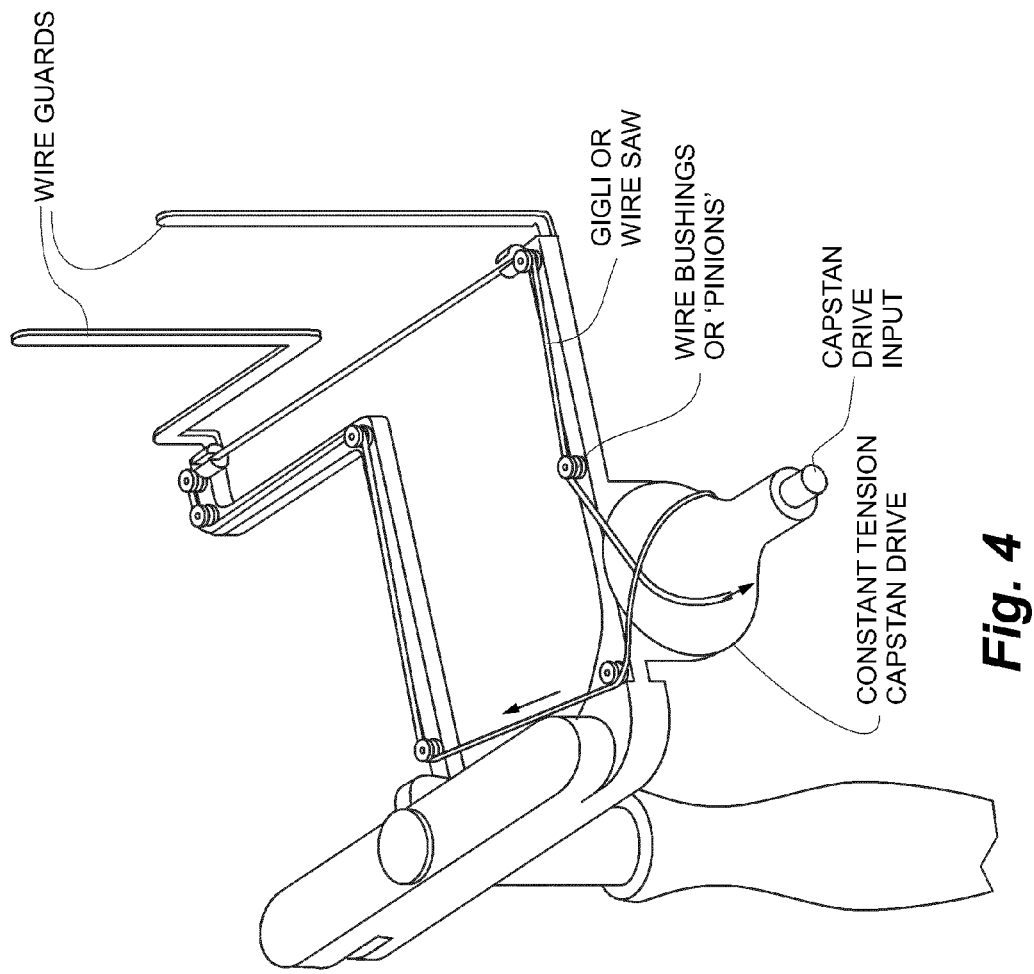

As shown, for example, in FIG. 4, a crank handle can be connected to the capstan drive input and the cutting wire member manually driven by the surgeon in a manner similar to that of reeling in a fish with a fishing pole and reel. Although this may sound a bit archaic relative to some of the higher technology means disclosed herein, surgeons may prefer this option as it provides for outstanding control of the wire, and a direct tactile response as the cutting tool is manipulated to cut bone. In this embodiment of the present invention, to cut a ligament will feel different than cutting bone and in that unlikely event the surgeon will know immediately that a ligament or other soft tissue is in the way of a cut, even though he may not be able to see what is happening. Especially in minimally invasive procedures where visibility may be compromised, this additional level of feedback may be very comforting and enable surgeons to more easily adapt to the demands of less invasive surgery.

Figure 23:
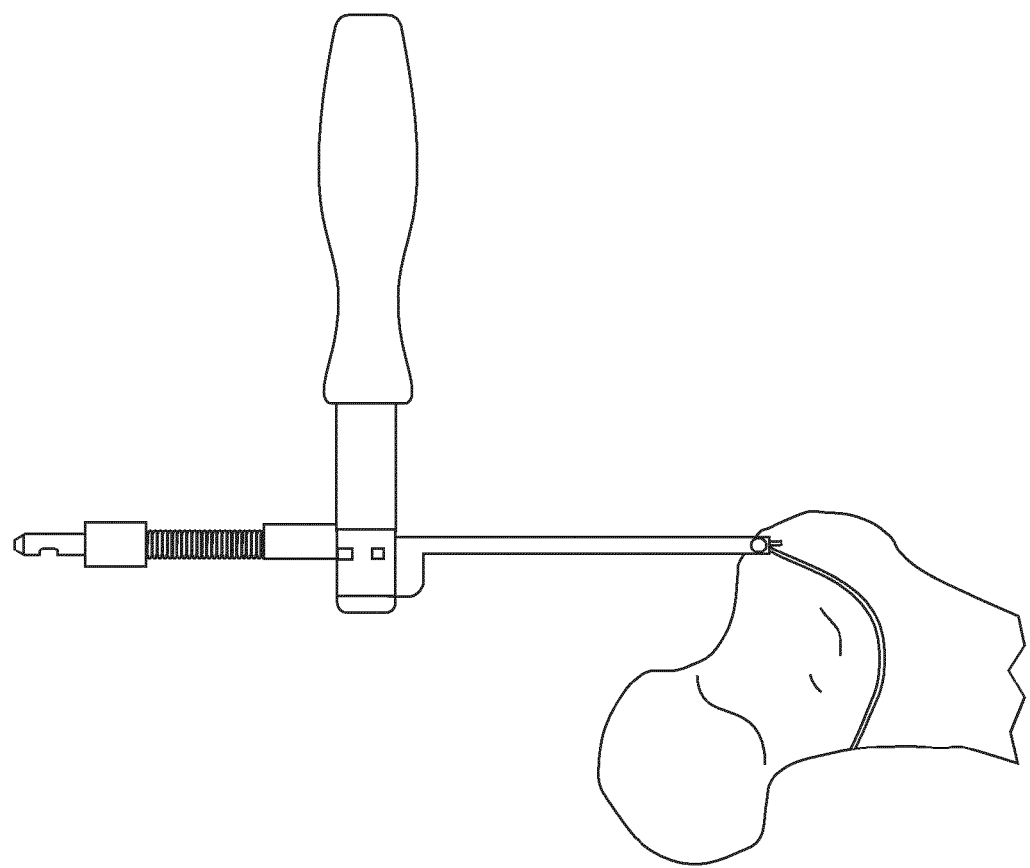
Figure 31:
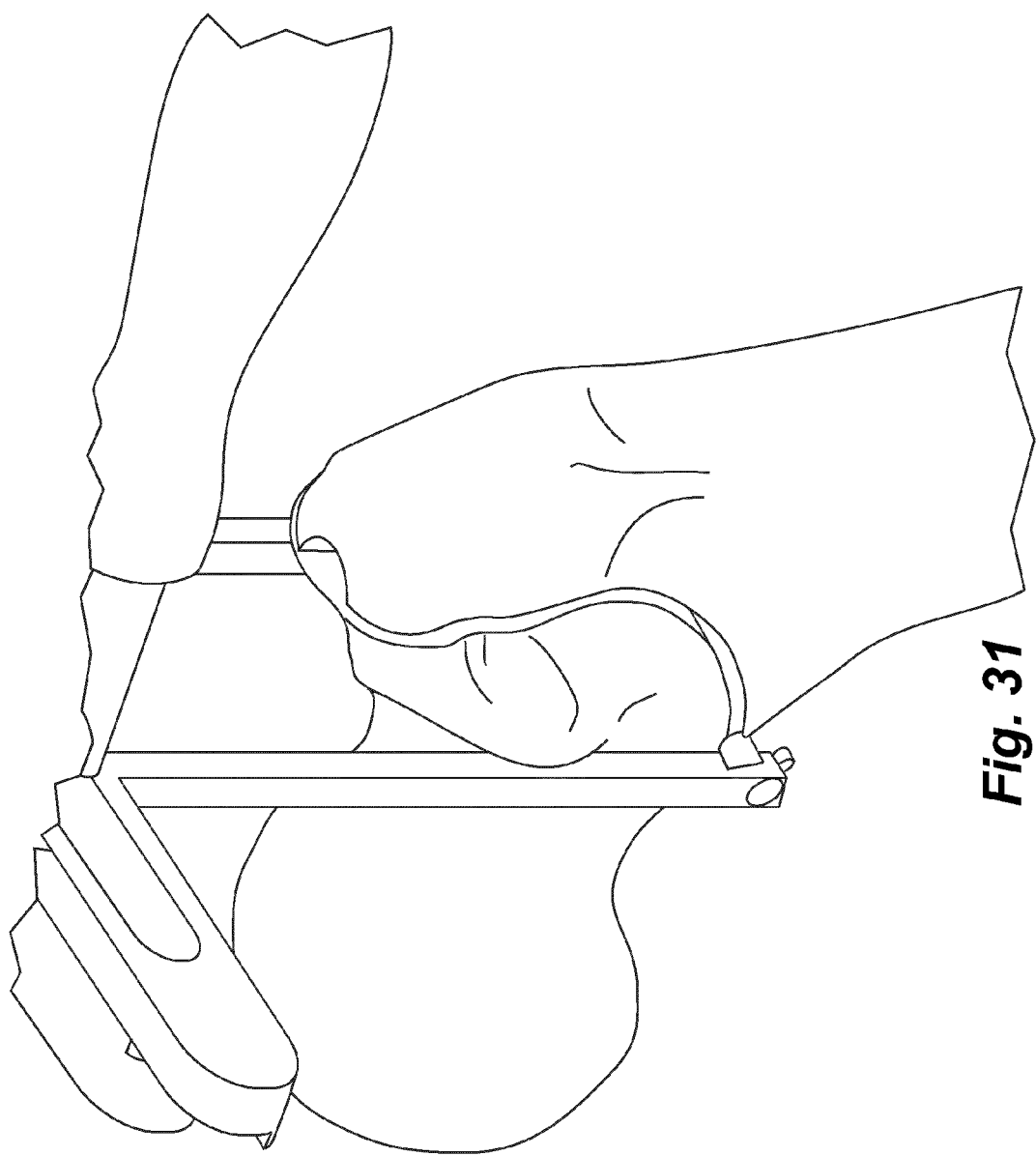
Figure 32:
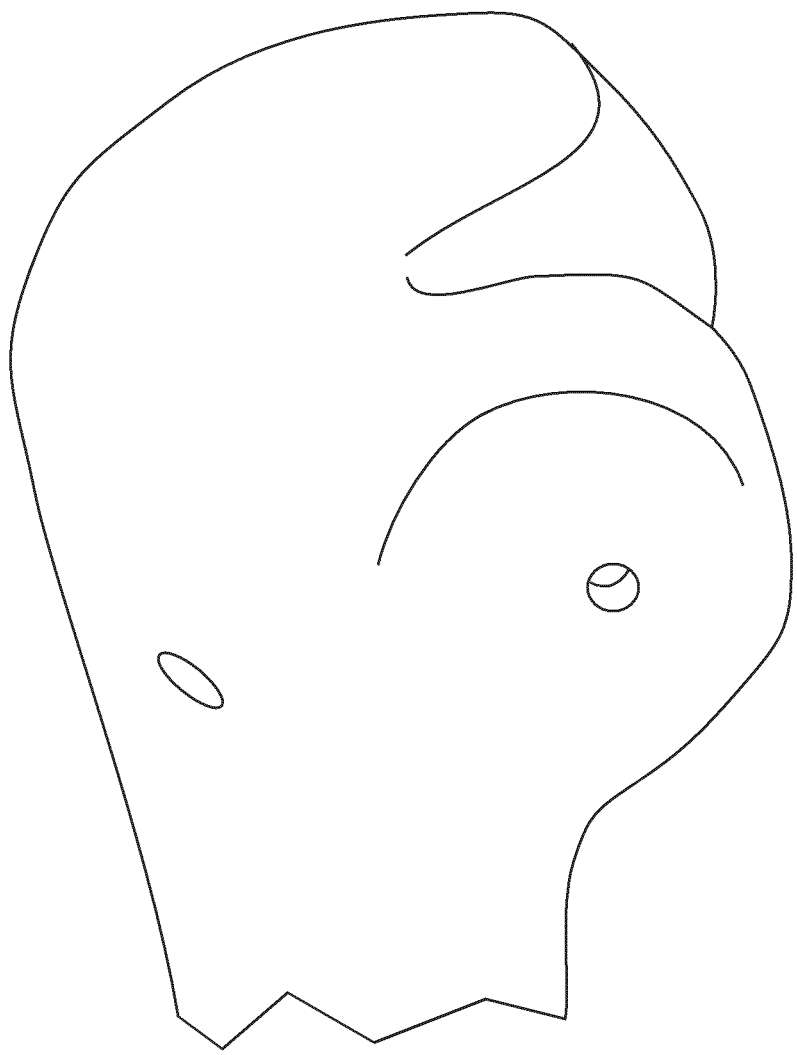

Another critical aspect of the present invention is preventing cutting tools which are capable of cutting soft tissue from coming into contact with soft tissue, thus damaging the soft tissue. As can be seen in FIGS. 23 and 31, the cutting surfaces of the wire extend from a handle surface in contact with one side of the bone, through the bone, and into another handle surface on the far side of the bone. In this manner, only the handle surfaces incapable of harming soft tissue are allowed to contact soft tissue, thus enabling safe use of the wire. If a standard oscillating saw were used to cut, for instance, the neck of the femur through a small incision, the saw, having completed the cut, could accidentally plunge into the soft tissue on the far side of the bone causing severe harm to those soft tissues. The ability of the handle to open and close in response to its engagement to bone, or to a cutting guide is key in attaining this benefit in many applications.

FIGS. 3-22 show several different embodiments of the present invention. FIGS. 3-11 show a continuous loop embodiment wherein a continuous wire loop is engaged and captured within the guide handle and driven in a rotary (like a band saw) or reciprocal motion (like a scroll saw). One interesting feature of this is the capstan drive shown in FIGS. 4, 6 and 11, which imparts driving force to the wire and maintains tension in the wire. This mechanism takes advantage of what has been referred to as the capstan effect, a very effective means of obtaining incredible mechanical advantage. The mathematic relationships between torque input, capstan or drive input rpm, force input and output, tension, and wire velocity or surface speed are as follows:

The relationship between the tensile force exerted on the wire by the capstan prior to failure of the drive to move the wire ($F_{tmax}$), the number of times the wire is wrapped around the capstan ($\theta$ in radians), the dynamic or static coefficient of friction ($\mu$), and the force resisting movement of the wire at the moment of failure of the capstan to drive the wire ($F_r$) is $$F_{tmax} = F_r e^{(\mu\theta)} \qquad \text{(Equation 1)}$$

The relationship between torque input to the capstan ($T_c$—manual or powered), the location of the wire with respect to the drive axis or centerline of the capstan (R—the effective radius of contact between the wire and the capstan), and $F_t$ (the tensile force imparted to the wire in operation) is $$F_t = T_c R \qquad \text{(Equation 2)}$$

The relationship between the speed of rotary input ($S_r$), and the surface or linear speed of the wire ($S_l$) is $$S_l = S_r R \qquad \text{(Equation 3)}$$

Figure 18:
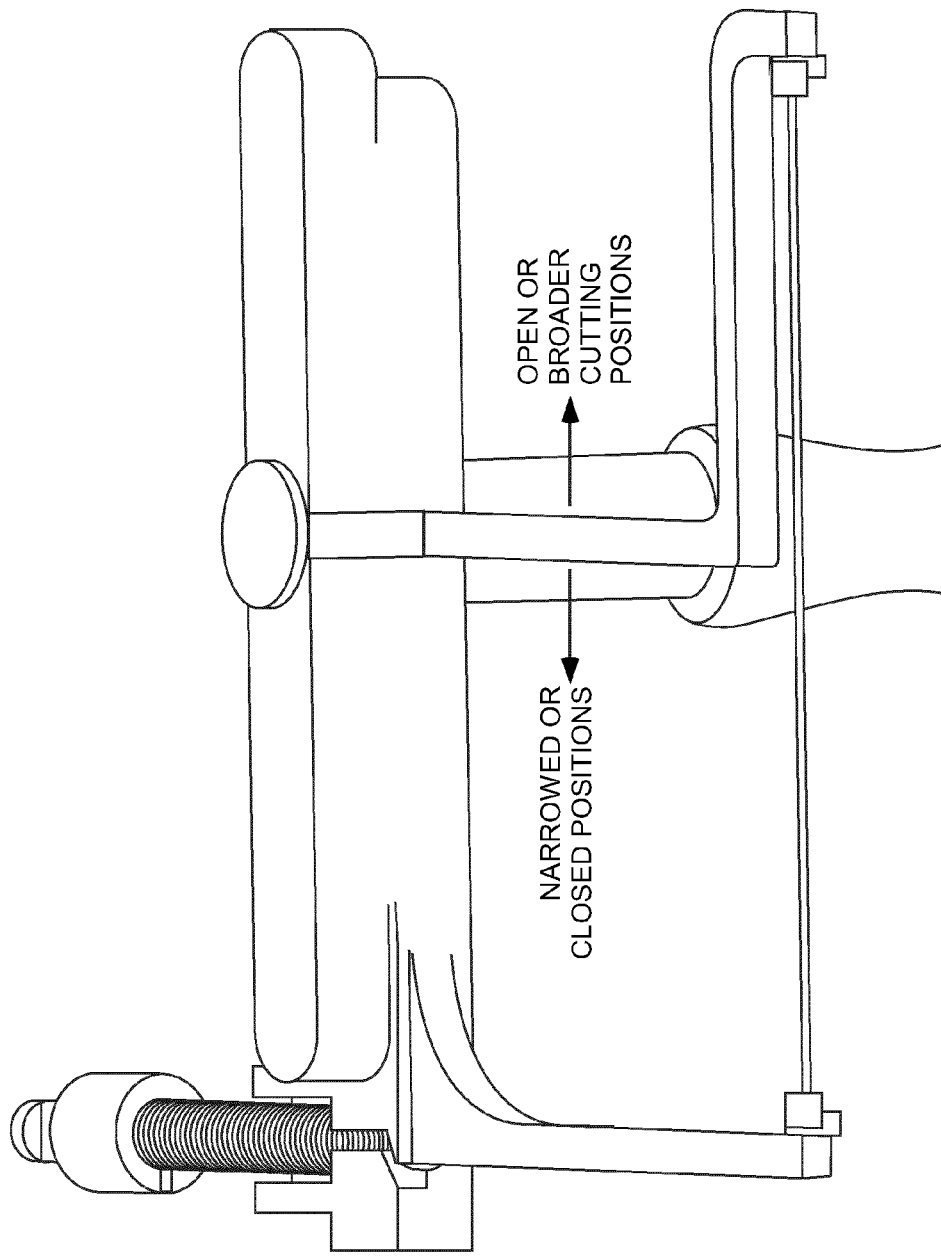
Figure 24:
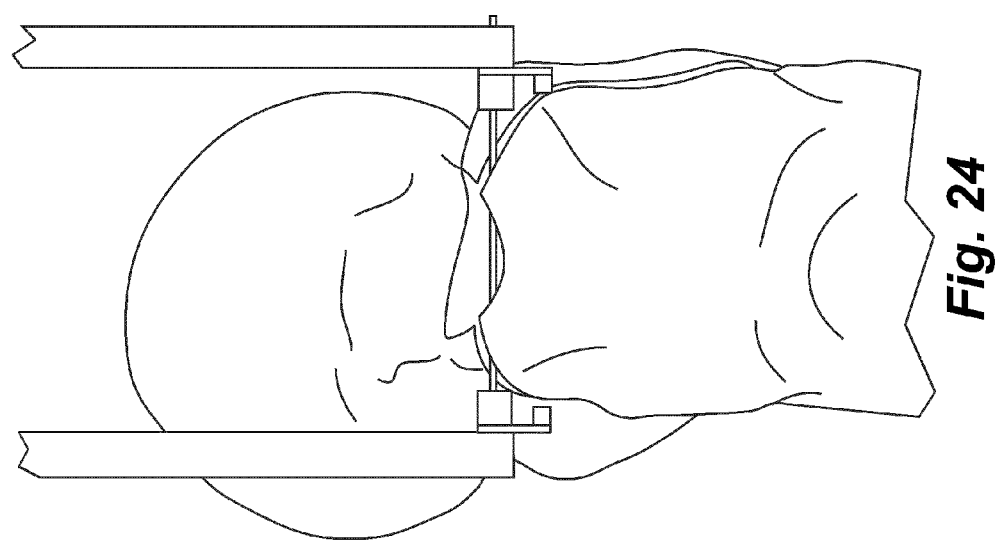
Figure 25:
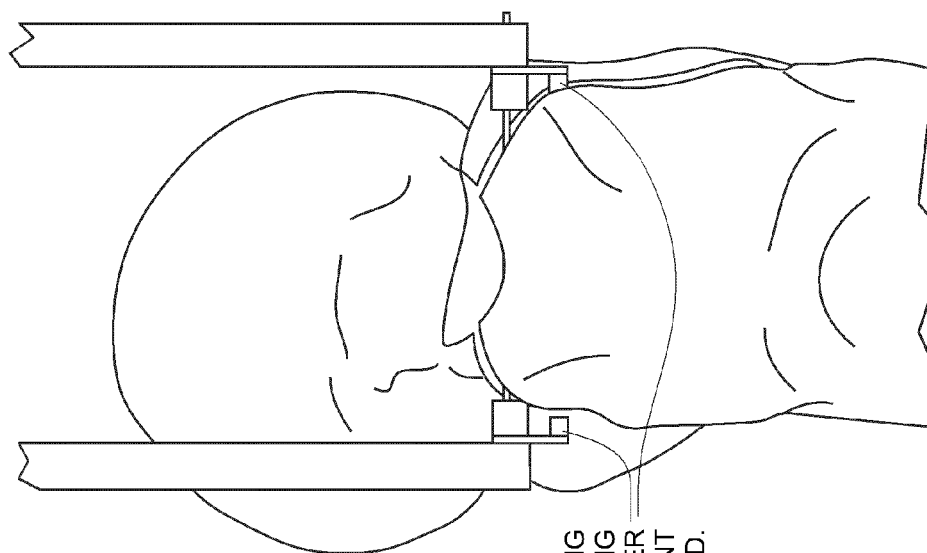
Figure 26:
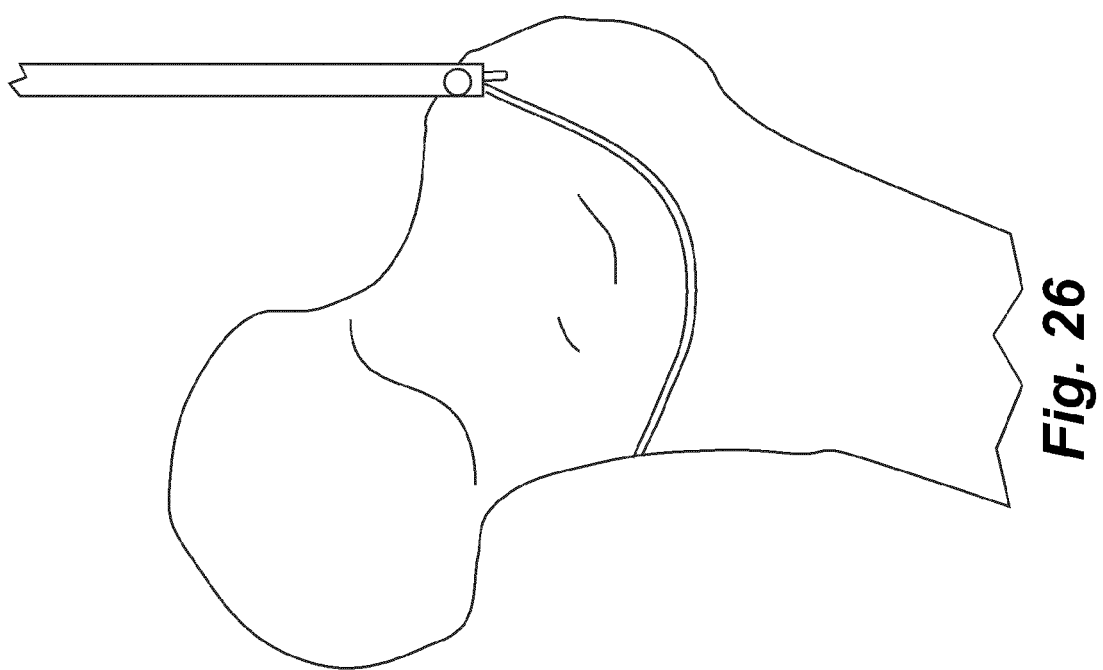
Figure 37:
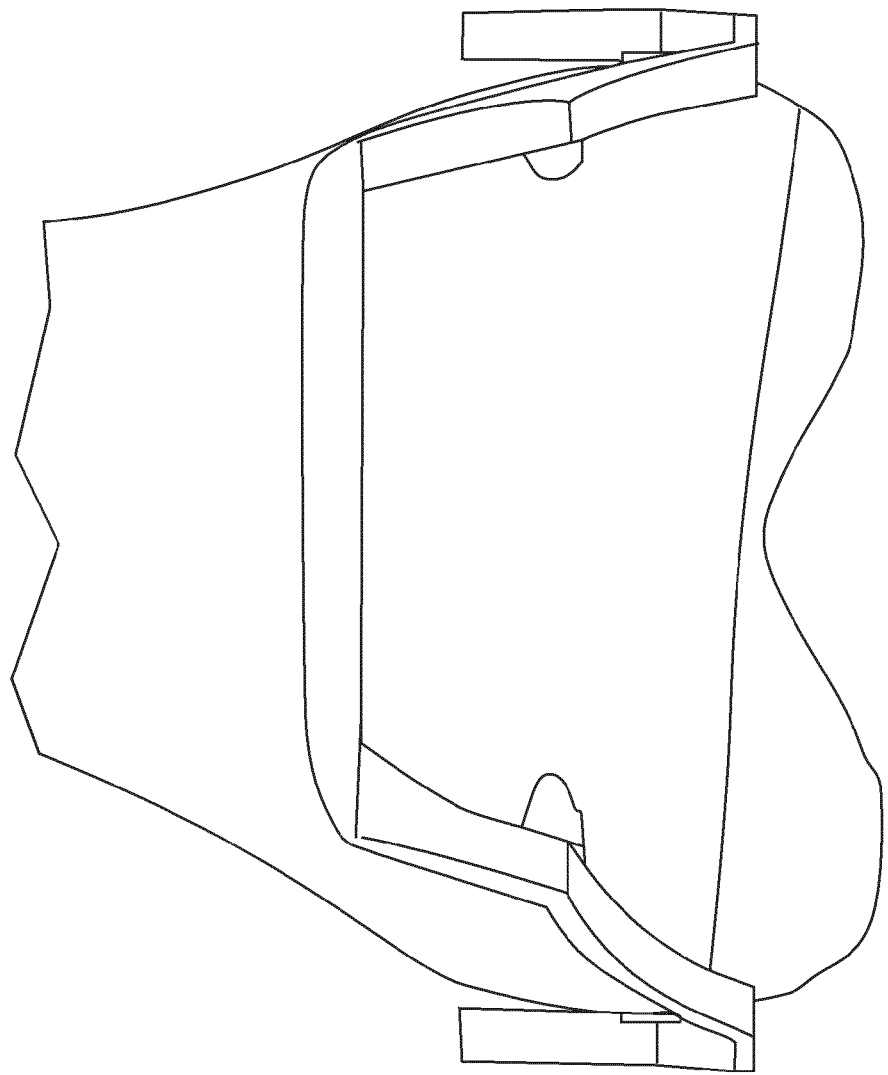
Figure 38:
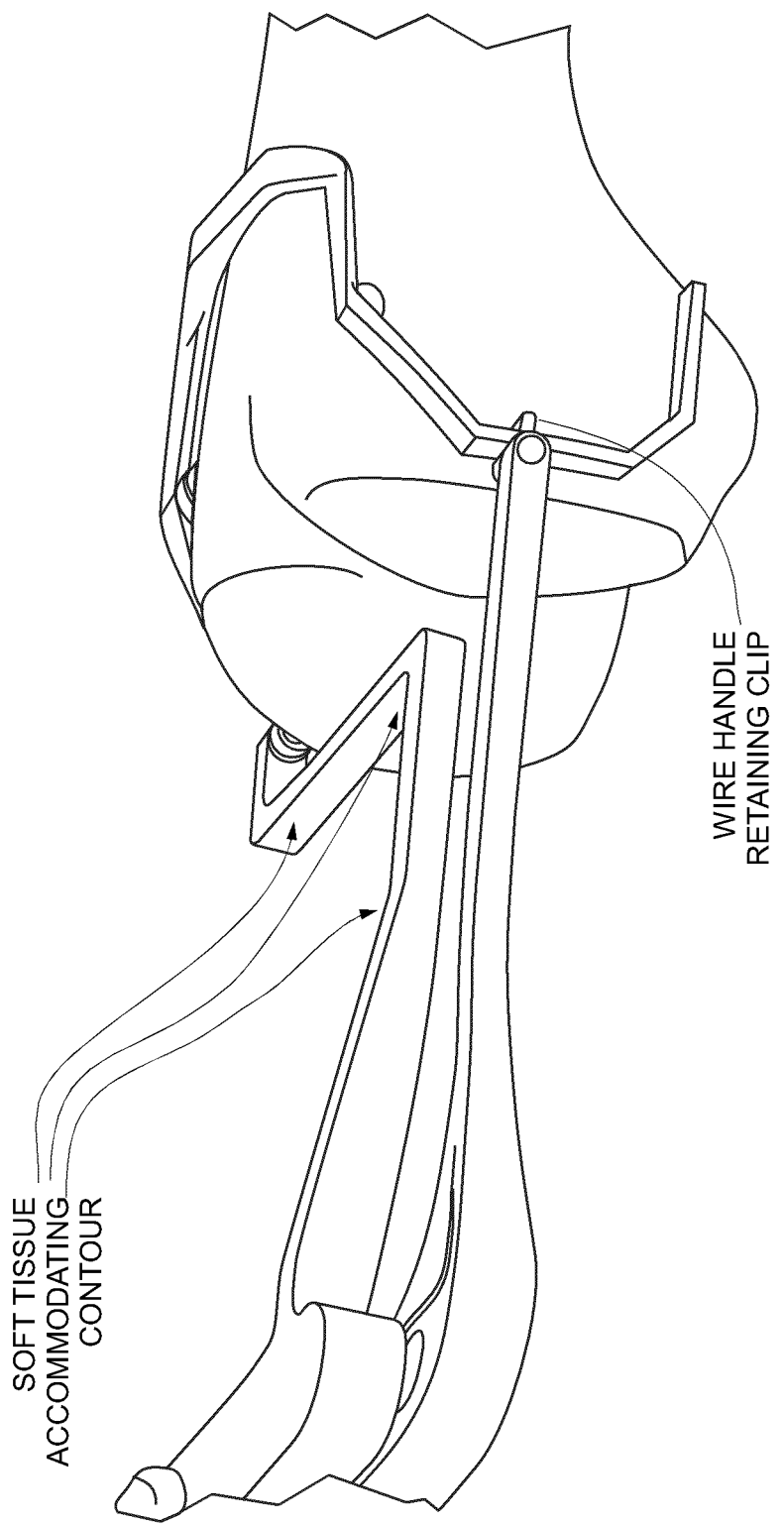

As shown in FIG. 18, in some applications, it is desirable to enable the arms of the handle to open and close smoothly while cutting bone without demanding the surgeon perform some adjustment of the device that would require him to delay the cutting process. As the arms open or close, it is desirable to maintain tension on the wire. To enable these desirable goals, FIG. 6 demonstrates that the capstan can be spring loaded to maintain firm contact between the wire and the capstan as the arms open and close. Although not shown, it may also be desirable to implement a derailer mechanism similar to that used on 10-speed bicycles to change gears—thus the operator could select a 'speed setting' and manipulate the derailer mechanism to establish the preferred cutting speed. Alternatively, the derailer can be an automatic or semi-automatic device that dictates the location of the wire on the capstan as in response to wire tension. It is within the scope of the present invention that the capstan be of any radially concentric geometry, and it is not simply limited to the conical configuration shown. For instance, the wire can take the embodiment of a cogged cable or chain wherein the capstan could take the form of a gear. Also, the handle can be further biased to force the arms of the handle toward open or closed positions during operation to maintain the cutting guide engagement features and/or bone engagement features in contact with cutting guides and/or bone, respectively, without time consuming manipulation of the device by the surgeon (as seen in FIG. 37 where the width of the guide changes along its cutting path to enable the guide to conform to the geometry of the boundary of the resected surface, and FIG. 24 where no guide is shown but the boundary of the resected surface changes and the engagement features of the guide are able to remain in contact with the boundary). It is an important objective of the present invention to reduce both the amount of time and intellectual effort required to use the invention and thus the device should be 'smart,' automatically doing what the surgeon wishes it to without requiring his attention or conscious intervention regarding the details of the device's operation.

Figure 3:
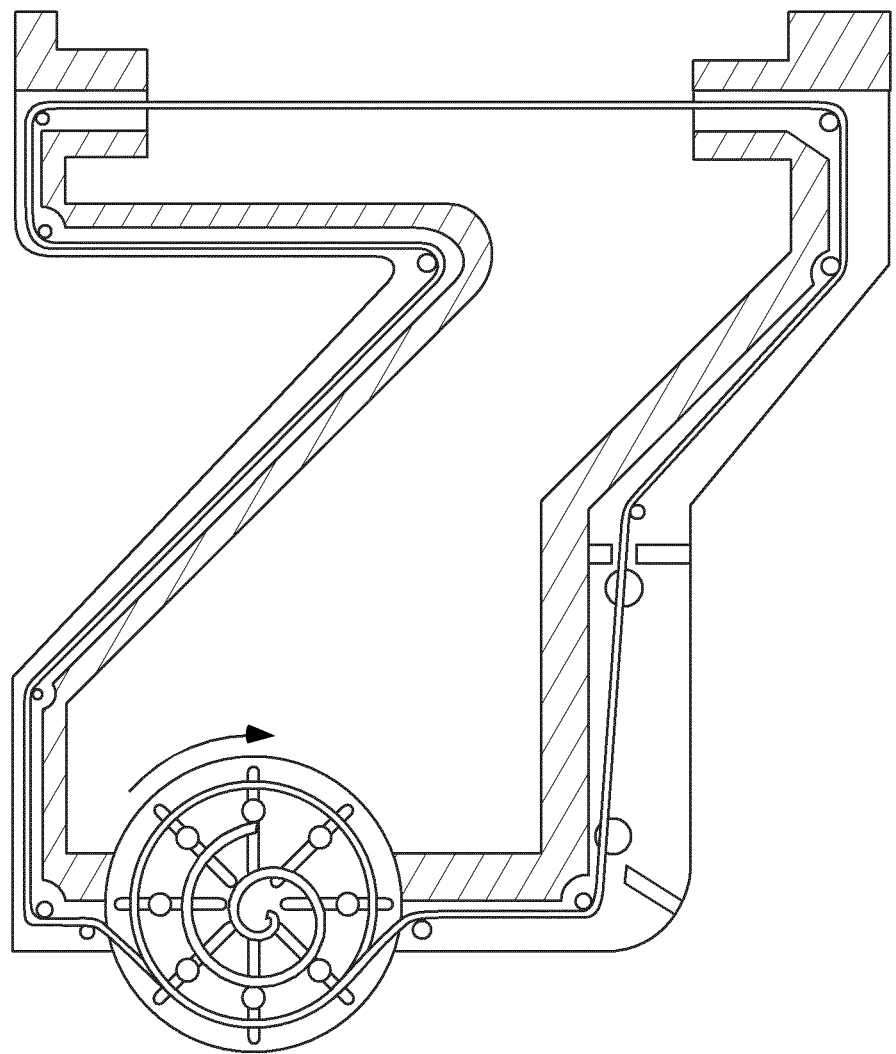
Figure 9:
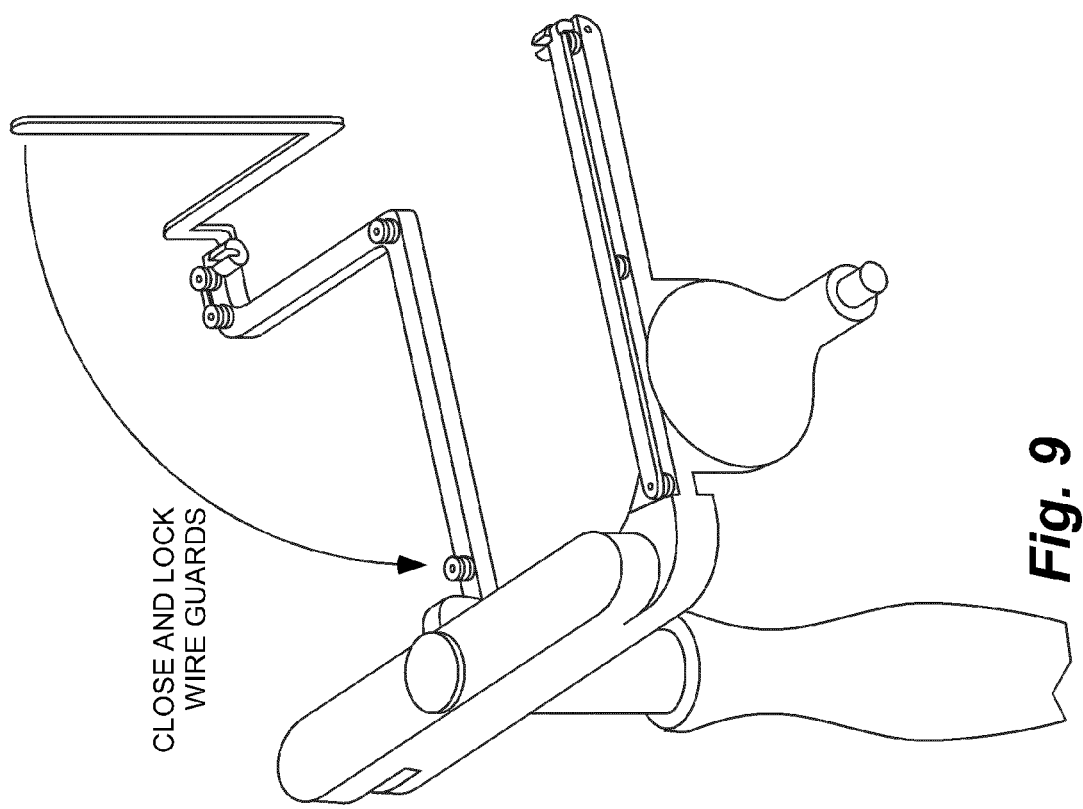
Figure 10:
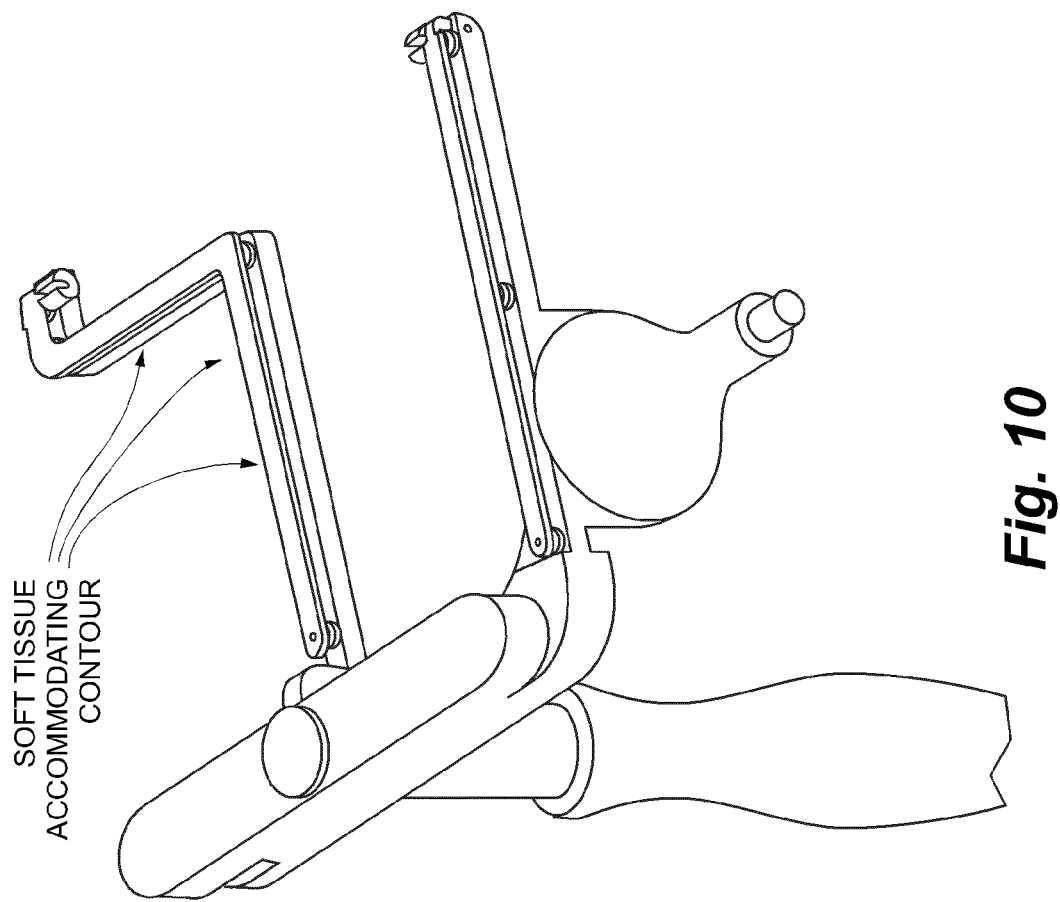
Figure 11:
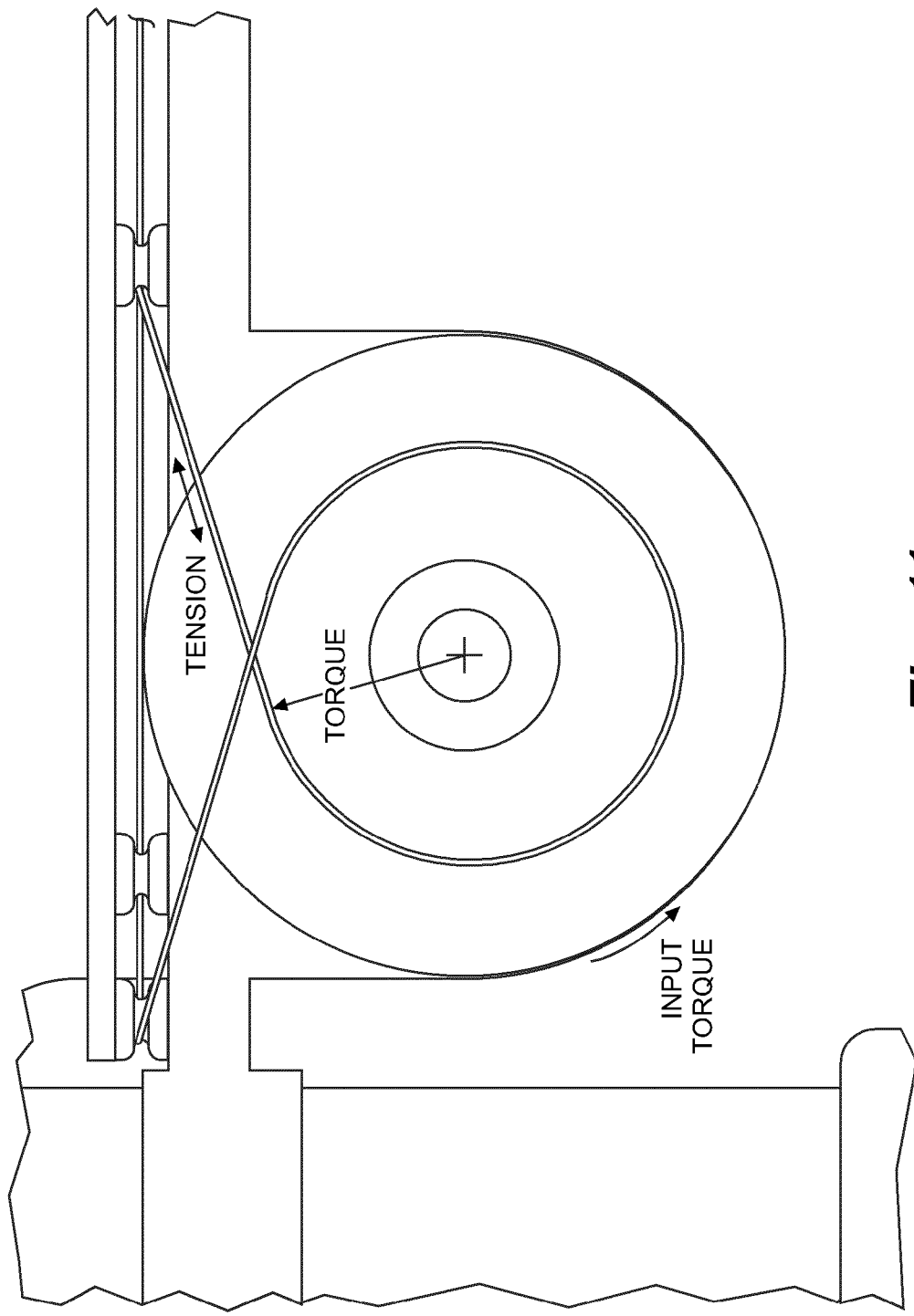

Patient safety is important, but the safety of the surgeon and the OR staff is also critical. As shown in FIGS. 4, 9 and 10, it may be desirable to include wire guards that prevent contact between the surgeon's hands and the wire during handling and use. As gigli saws are capable of amputating a human femur in a matter of seconds, preventing accidental contact with the surgeon's fingers or OR staff is key to the safety design of a wire or cable saw. FIG. 3 shows a different embodiment of the capstan drive embodiment of the present invention where the capstan is radially expandable to maintain tension and impart driving force to the wire. This also may be used to keep the wire in a single plane, as opposed to multiple planes of operation as in FIG. 11, which may help simplify and lessen the cost of the design. An interesting safety feature of capstan based embodiments is that if the wire breaks, tension drops to zero instantly and, since the wire has very little mass, thus little momentum, the wire will stop moving simultaneously with breakage. Although not shown in FIG. 6, a mechanism may be utilized to collapse the capstan spring during assembly to facilitate ease of assembly.

Figure 12:
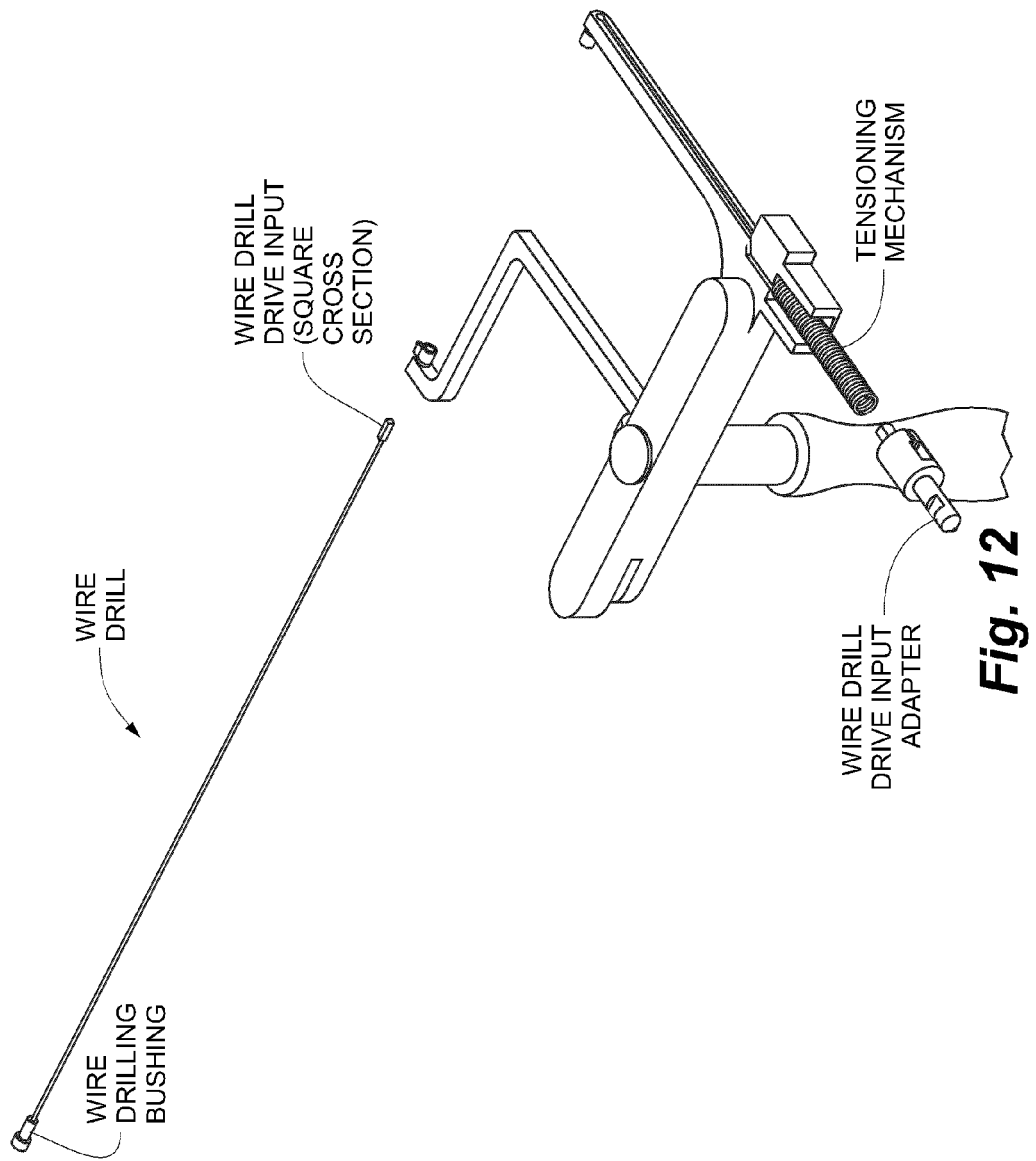
Figure 13:
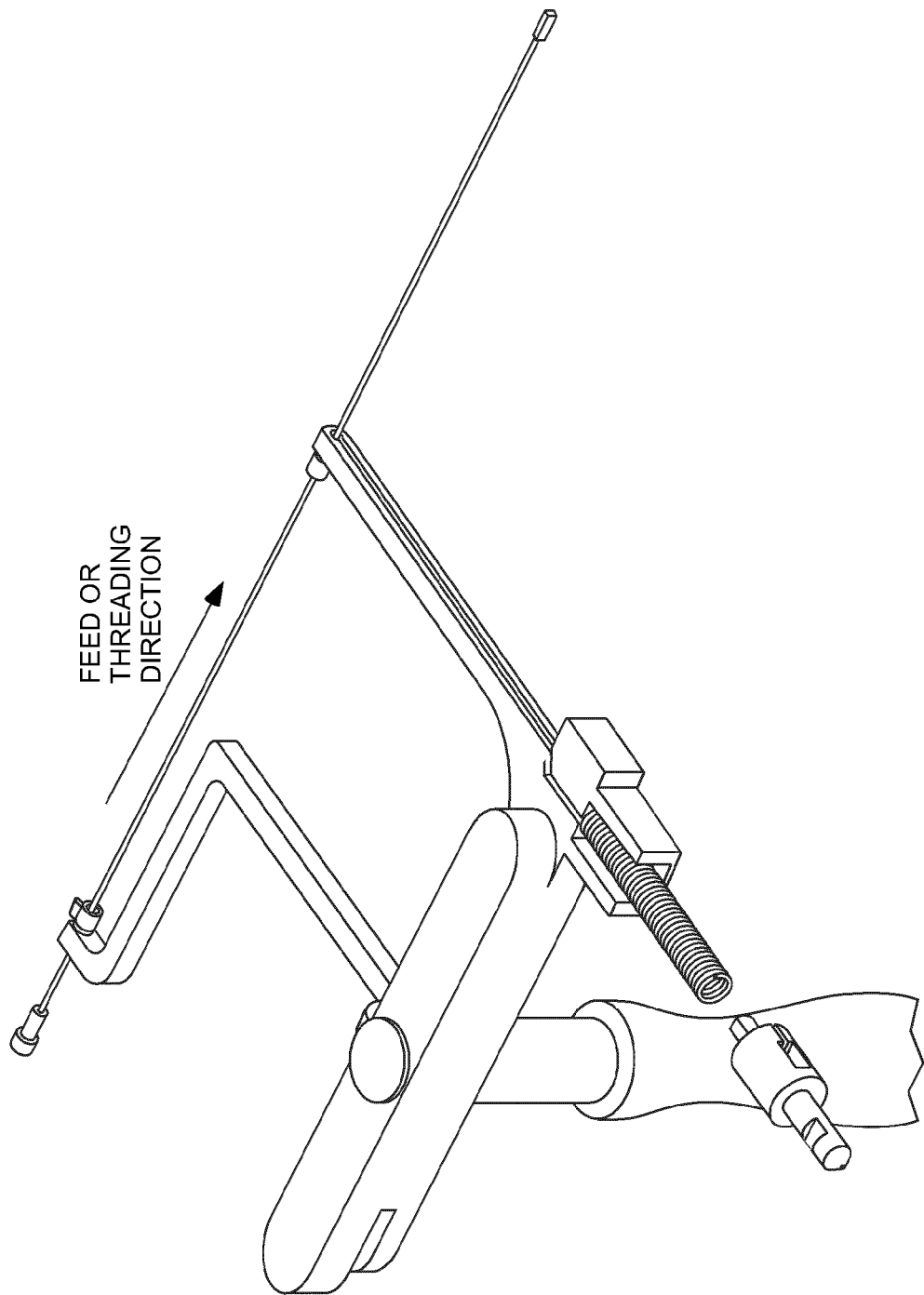
Figure 14:
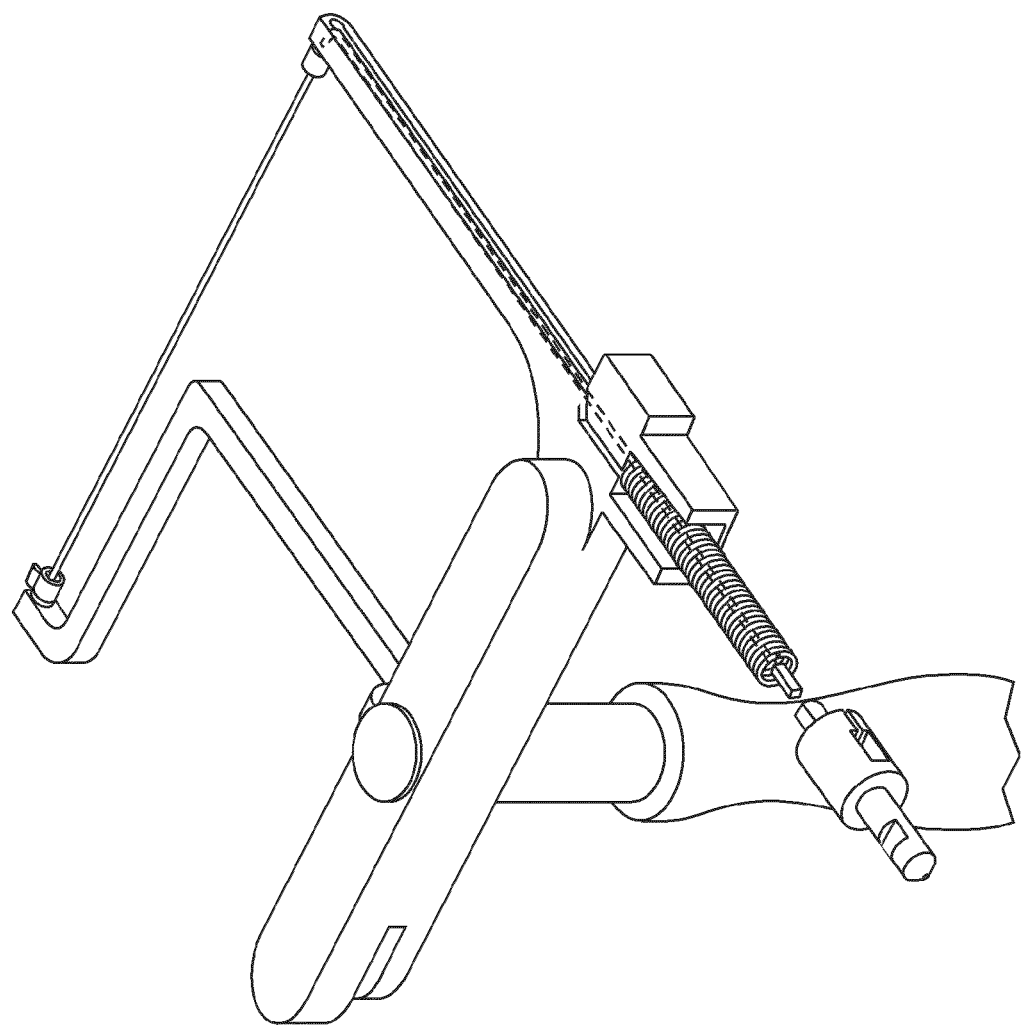
Figure 15:
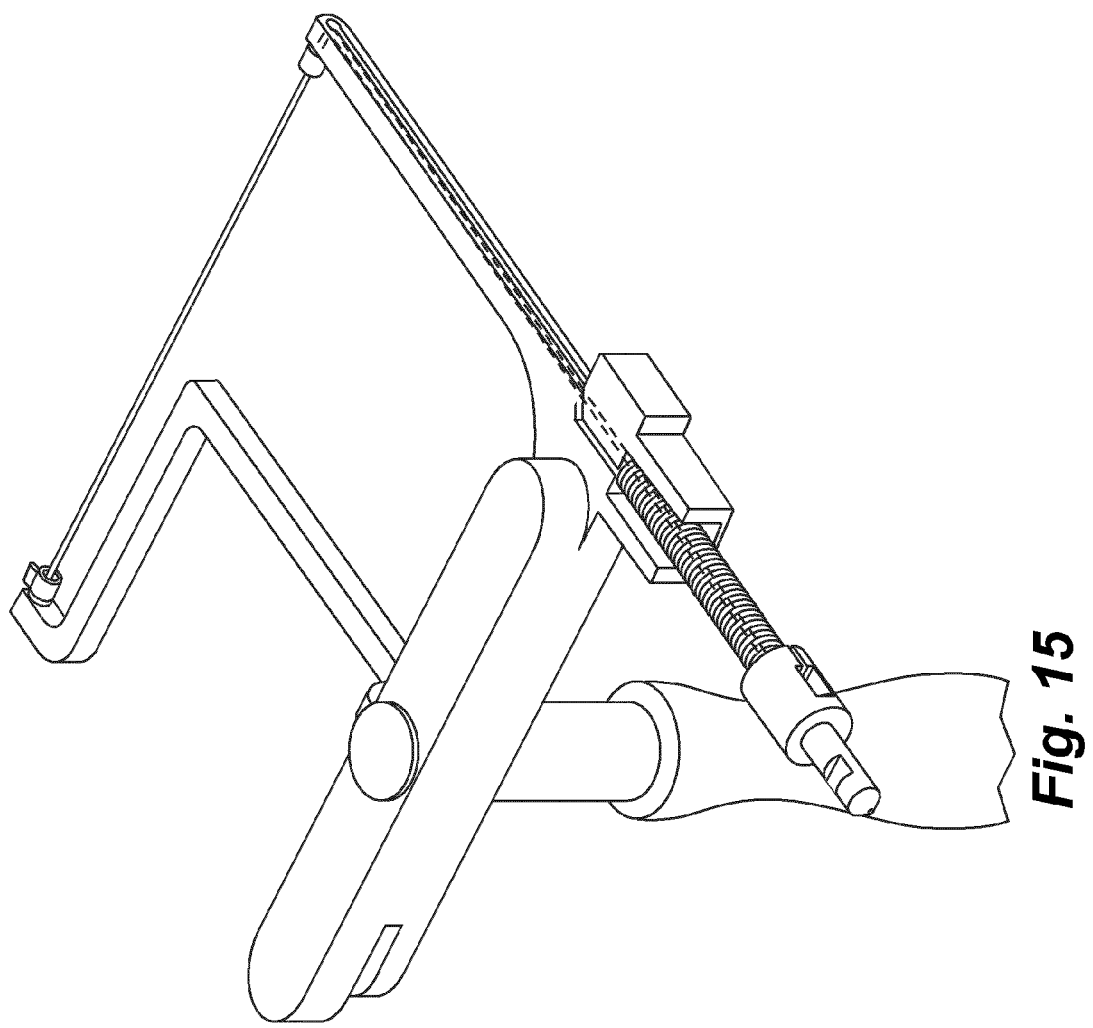
Figure 16:
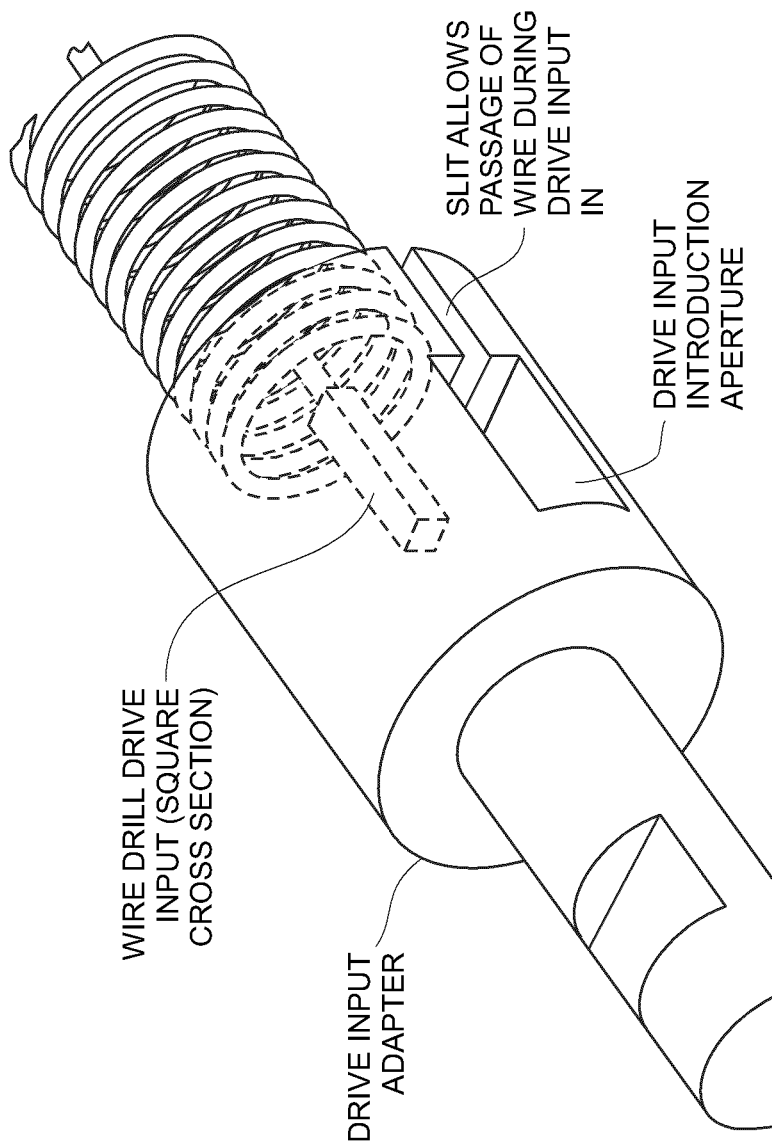
Figure 17:
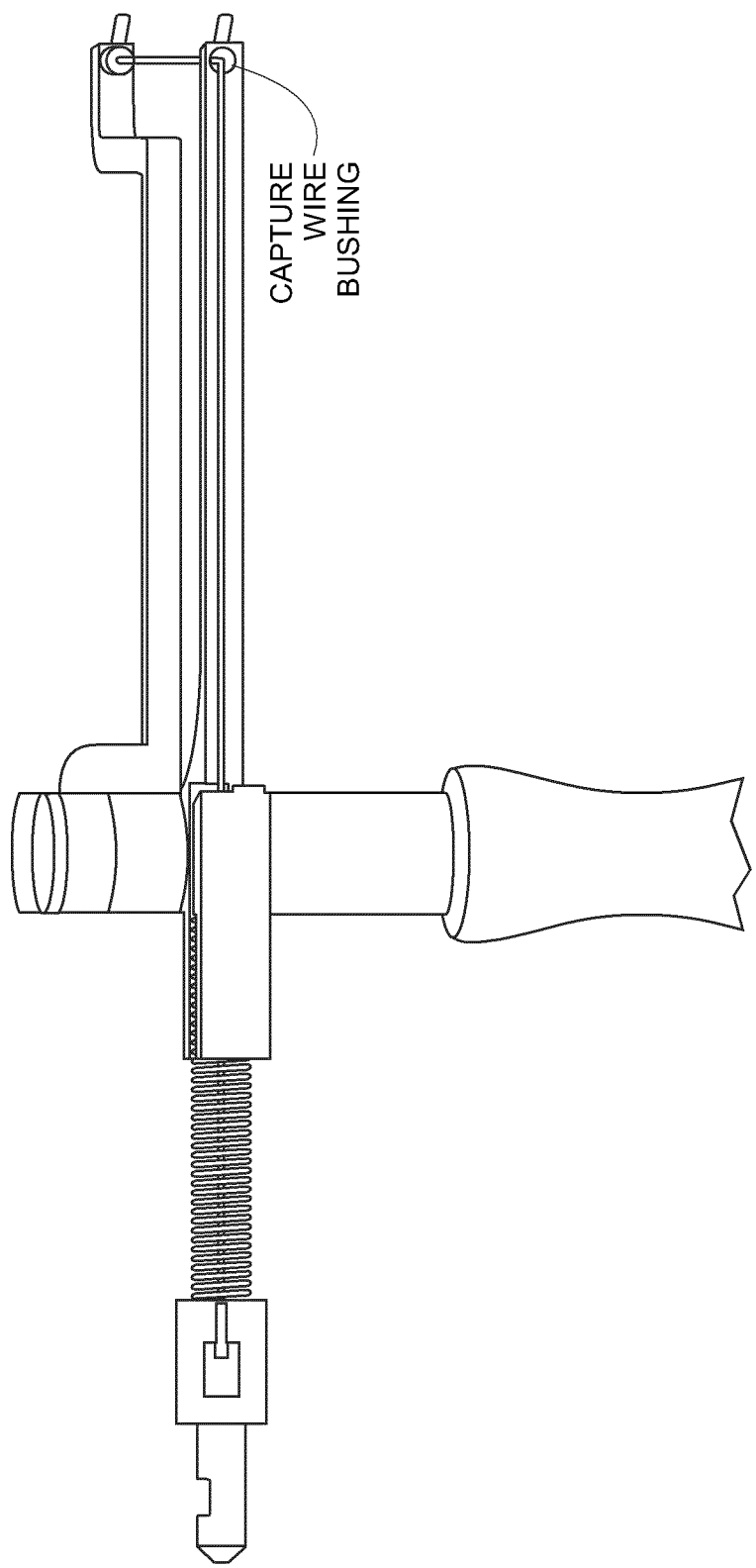

FIGS. 12-18 show an embodiment of the present invention which may further reduce cost and utilize a wire cutter in a manner similar to that of the side cutting drill shown in FIG. 1. Once again, a spring is utilized to maintain tension on the wire as the handle arms move toward opened or closed positions (see FIG. 18). In this embodiment of the present invention, the wire saw includes a Bushing, a cutting portion, and a drive input (which is square in cross-section in this embodiment for mating engagement with a square recess in the drive input adapter), as shown in FIGS. 12 and 16. Although this embodiment can be preassembled for ease of use, economics may make it desirable for the wire saw to be disposable, while the handle is durable, thus requiring preoperative or intraoperative assembly of the wire saw with the handle. As shown in FIGS. 12-16, assembly of this embodiment could involve threading the wire through apertures, captured bushings and/or slots in the handle and engaging the wire drive input feature of this wire cutter embodiment to the drive input adapter. It is of importance to note that this embodiment of the present invention provides for complete internal capture of the wire preventing accidental contact between the wire and either the patient's soft tissue or the surgeon. Alternatively, if exposed fixtures are used for threading the wire, a cover member could be installed over the wire and exposed fixtures, either prior to use or after threading the wire through the device, depending upon the particular embodiment of the cutting tool. Both the Wire Drill Bushing of the wire drill shown in FIG. 6, and the Captured Wire Bushing of the Handle in FIG. 17 act to prevent contact between the features of the Handle and the cutting surfaces of the Wire Drill during use. In operation in this embodiment, a powered drill is connected to the wire drill by way of the Drive Input Adapter, FIG. 16, the wire drill brought into contact with bone, and the powered drill actuated to spin the drill. With a diameter of, for instance, 0.04 inches, it may be desirable to rotate the wire drill at fairly high rpm to attain the necessary surface speed to easily resect bone. Balancing out the issue of surface speed is the small contact area between the wire and the bone thus leading to high pressures despite lower force levels. Optimum rpm for the powered drill in this embodiment will depend upon various factors, but drive speeds between 100 rpm and 60,000 rpm will work nicely.

Figure 19:
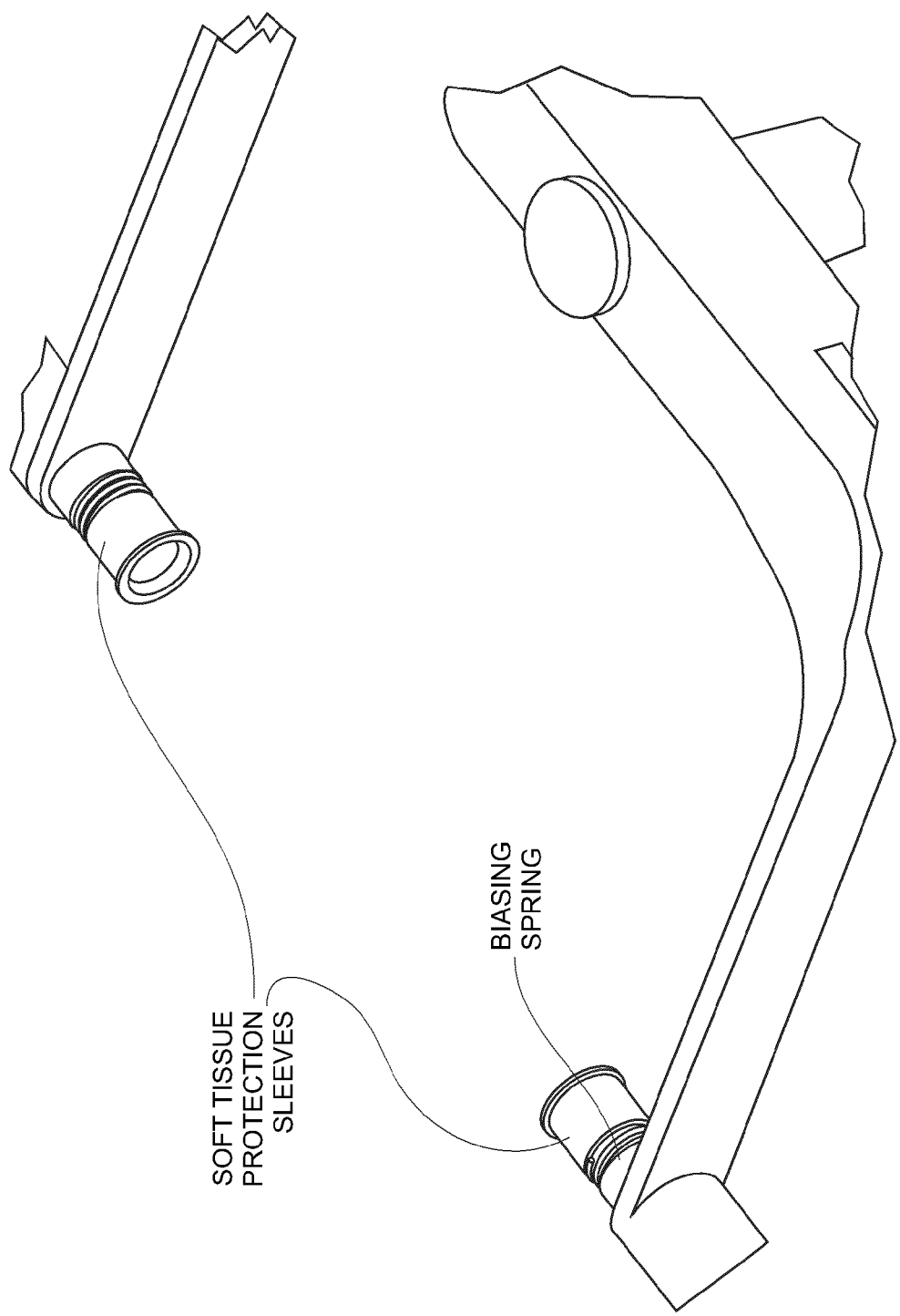
Figure 20:
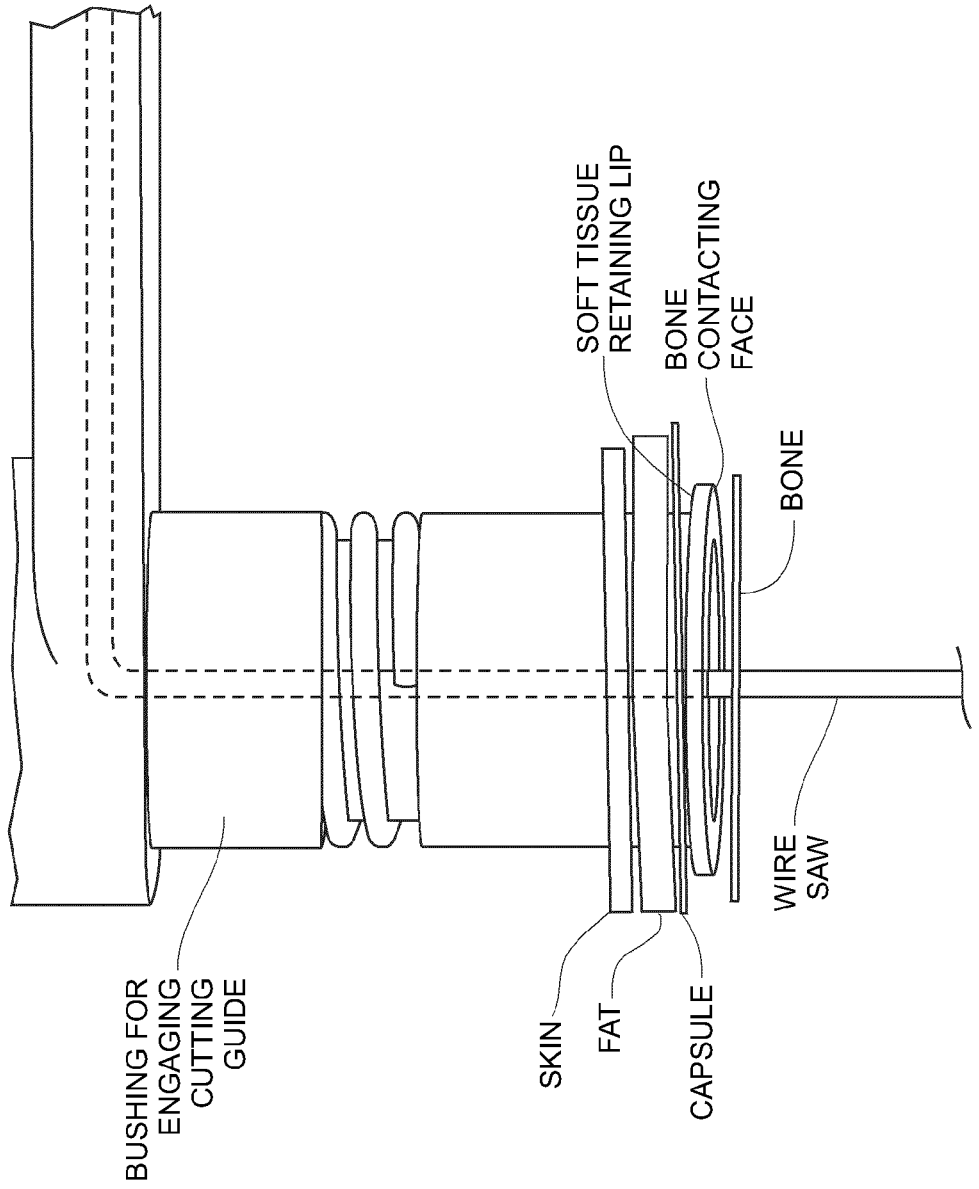
Figure 21:
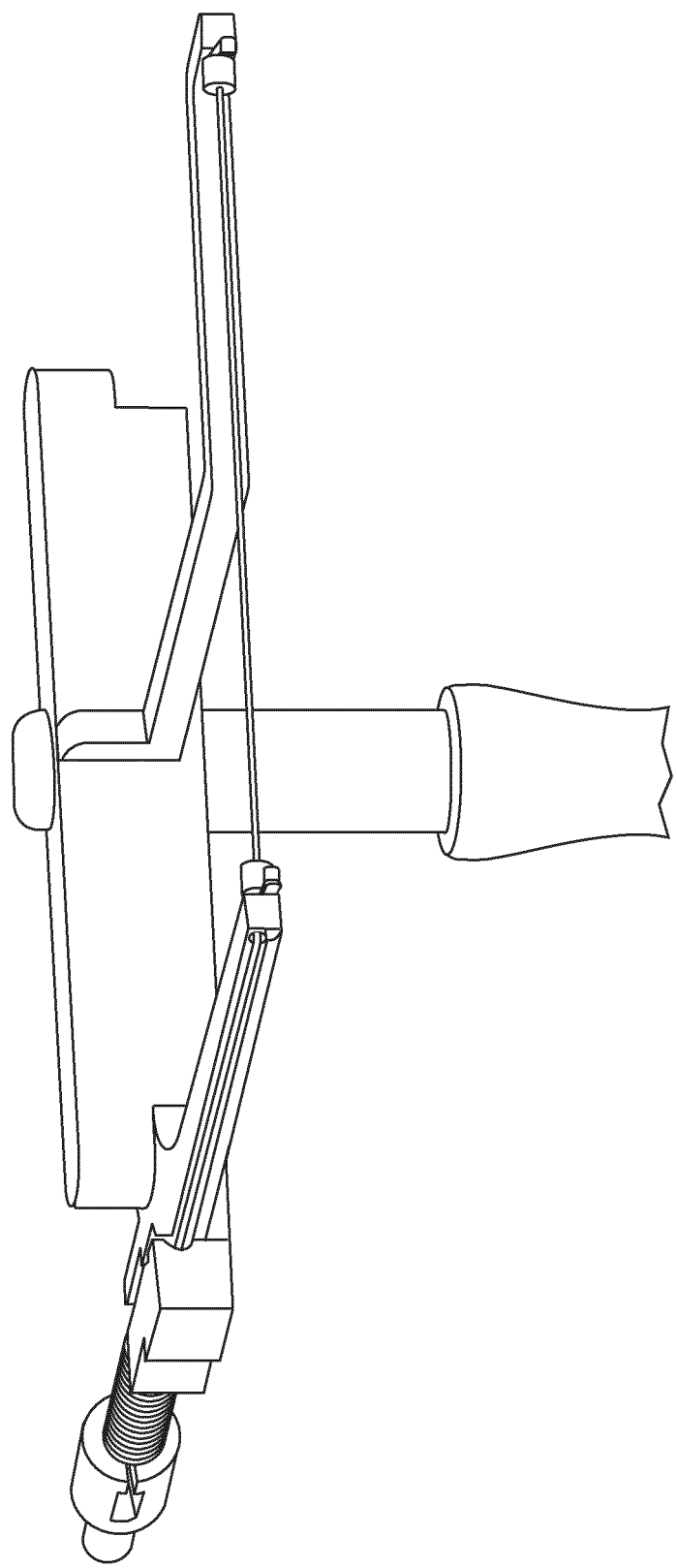
Figure 22:
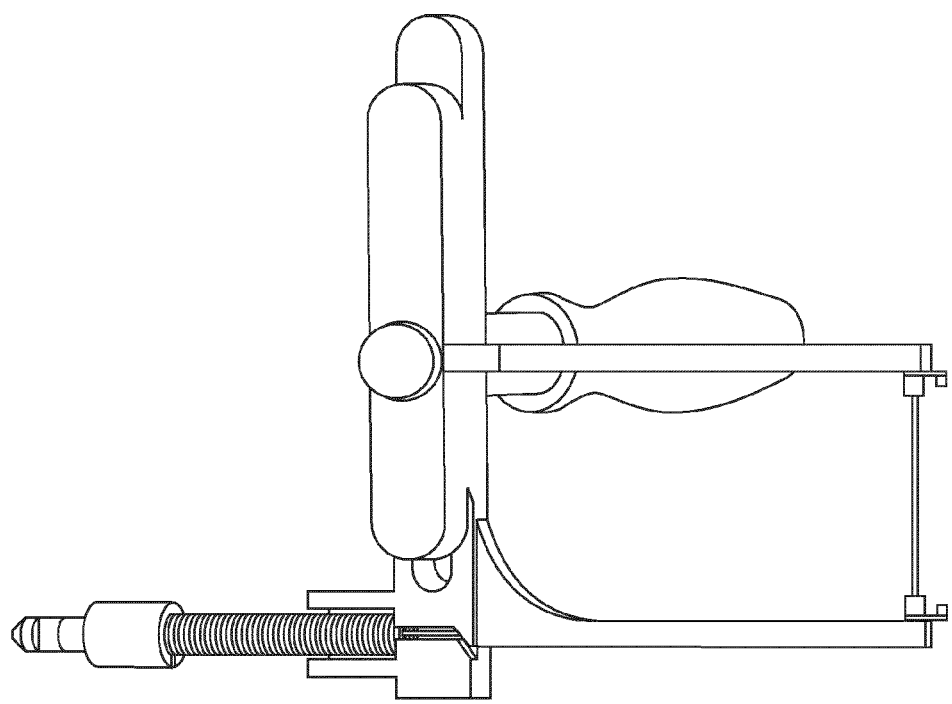
Figure 60:
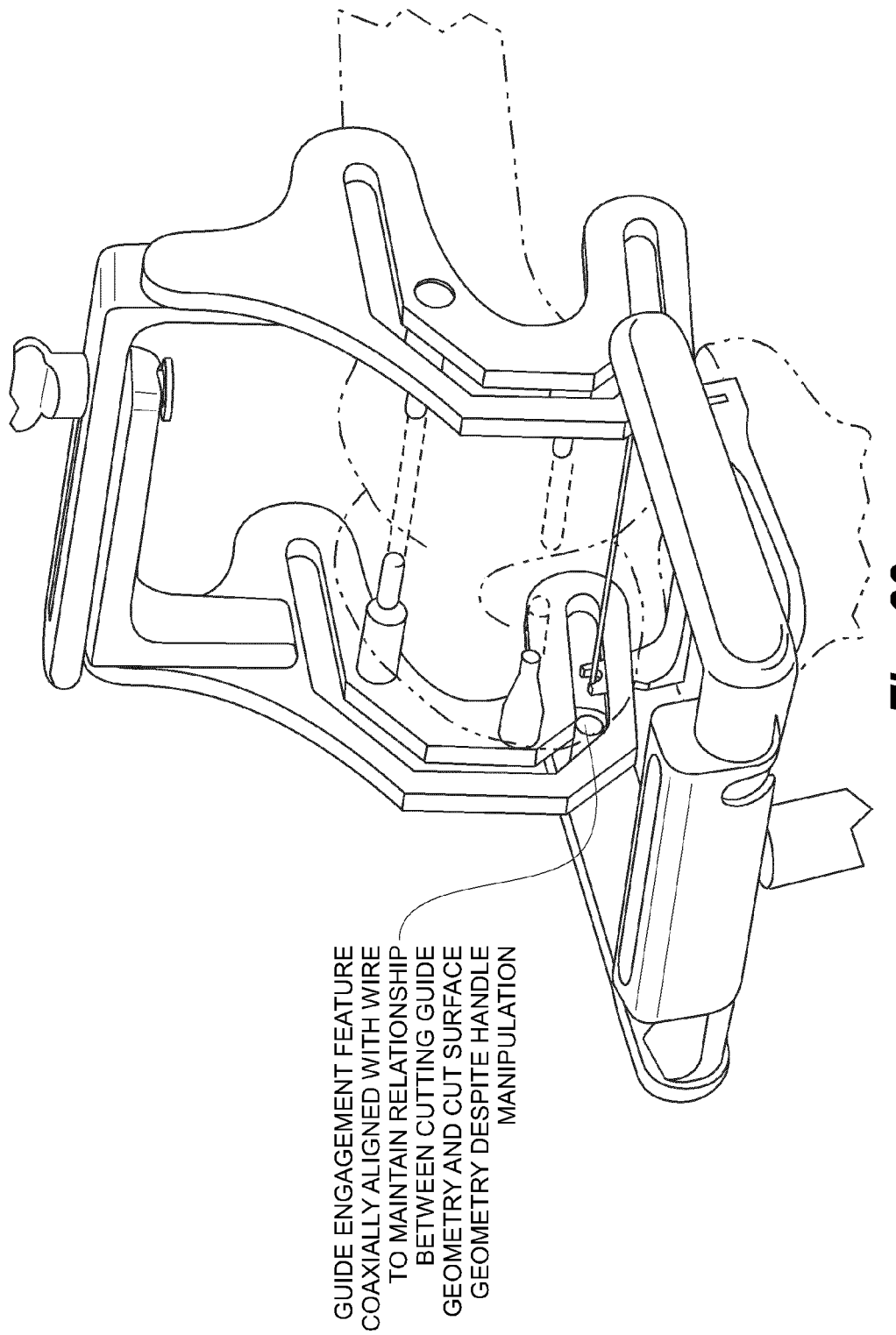

An additional feature that may be desirable to add to different embodiments of the present invention are the soft tissue protection sleeves shown in FIGS. 19 and 20. One clinical application calling for the benefits of this feature would be Transcutaneous Transarticular TKA ("TTTKA" or "Triple TKA" or "T Cubed" or "$T^3$" Procedures) where a PBR cutting guide, as generally shown in FIG. 60 is positioned completely outside of the wound with the exception of fixation features which extend from the externally located guides through skin incisions and into holes or apertures created in bone. As shown in FIG. 20, the cutting tool, in the case of the present invention a wire, is threaded through the handle, the guide, the skin, fat, capsule, etc., (soft tissue), across, through, or beneath the articular surfaces of the joint, and through the soft tissue, guide, and handle on the opposing side of the bone. The soft tissue protection sleeves are then extended through the soft tissue and into contact with the sides of the bone. The retaining lip can be used to maintain the sleeves in contact with the bone and are held there by the edges of the incision through the capsule during cutting. The springs shown in FIGS. 19 and 20 can further bias the sleeves into contact with bone in a manner that would maintain that contact as the width of the bone changed along the cutting path of the resected surface.

One skilled in the art will note that the thicknesses for the soft tissue represented in FIG. 20 will change significantly from patient to patient thus requiring the proportions of the sleeve, spring and other components of the present embodiment of the invention to change accordingly. For example, in an obese patient, the fat layer through which the cutting tool extends can be 5 inches thick per side or more. The diameter of the soft tissue protection sleeve can be significantly reduced with respect to what is shown as the wire diameter is so small, thus requiring a smaller capsular incision.

Figure 71:
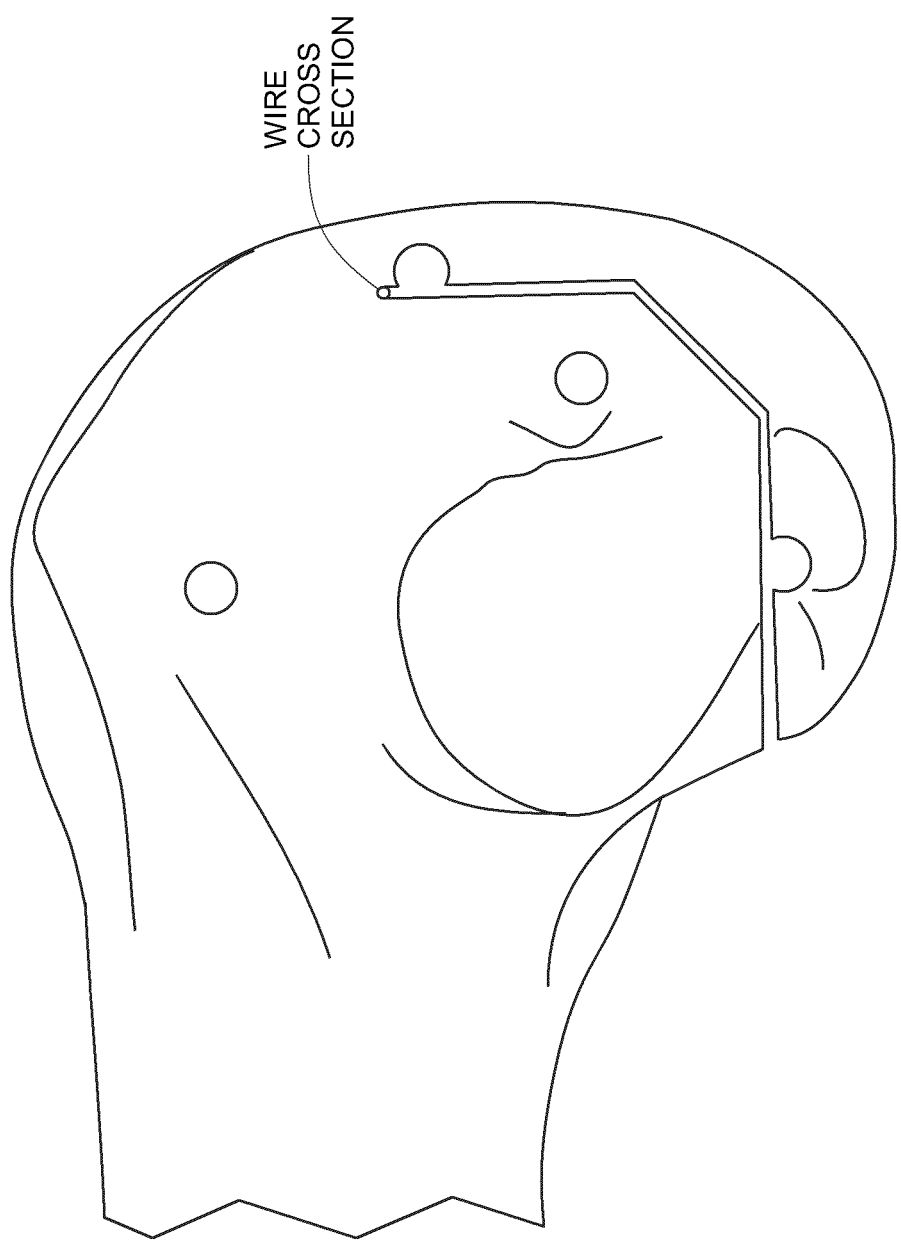
Figure 72:
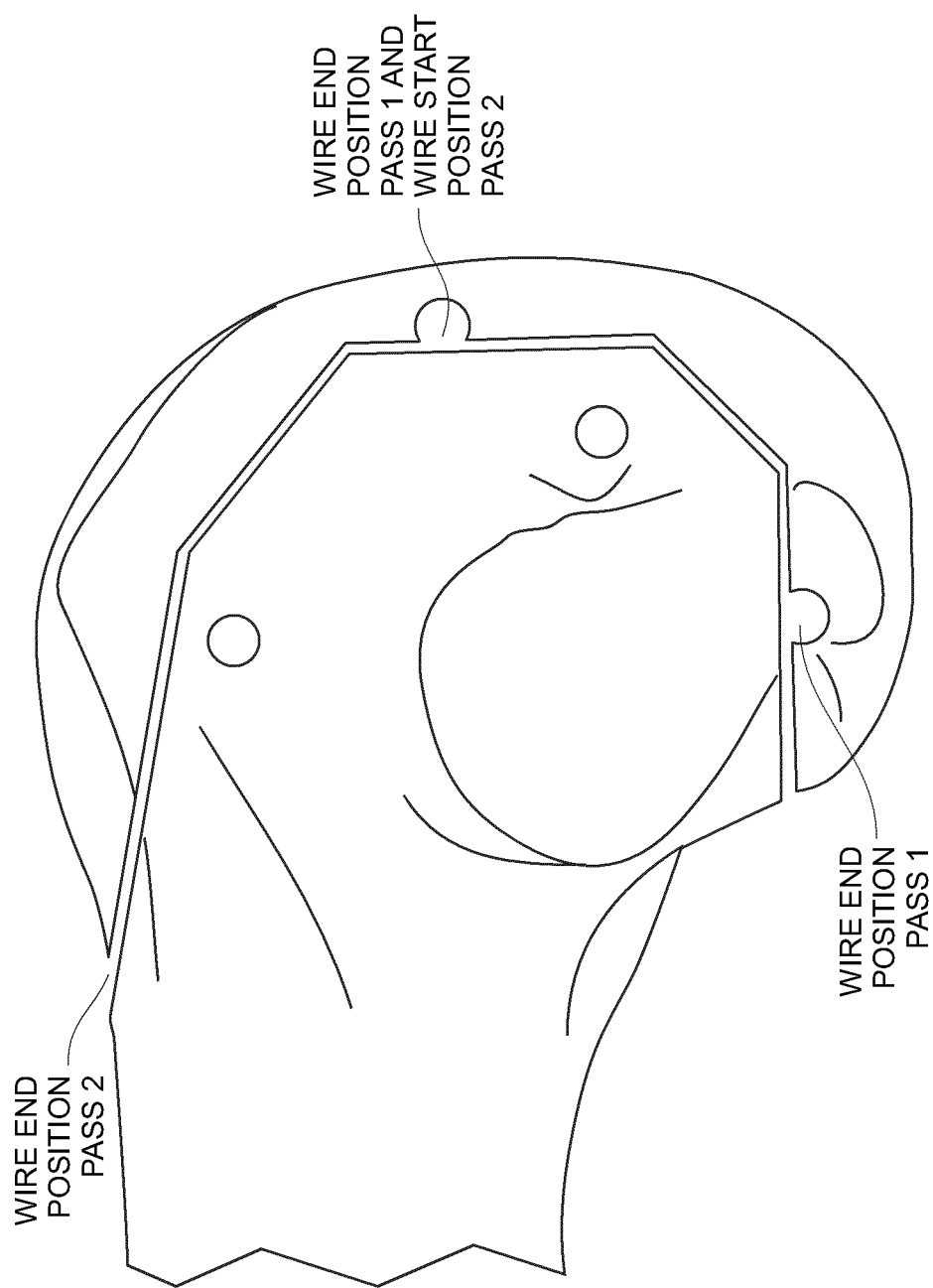
Figure 73:
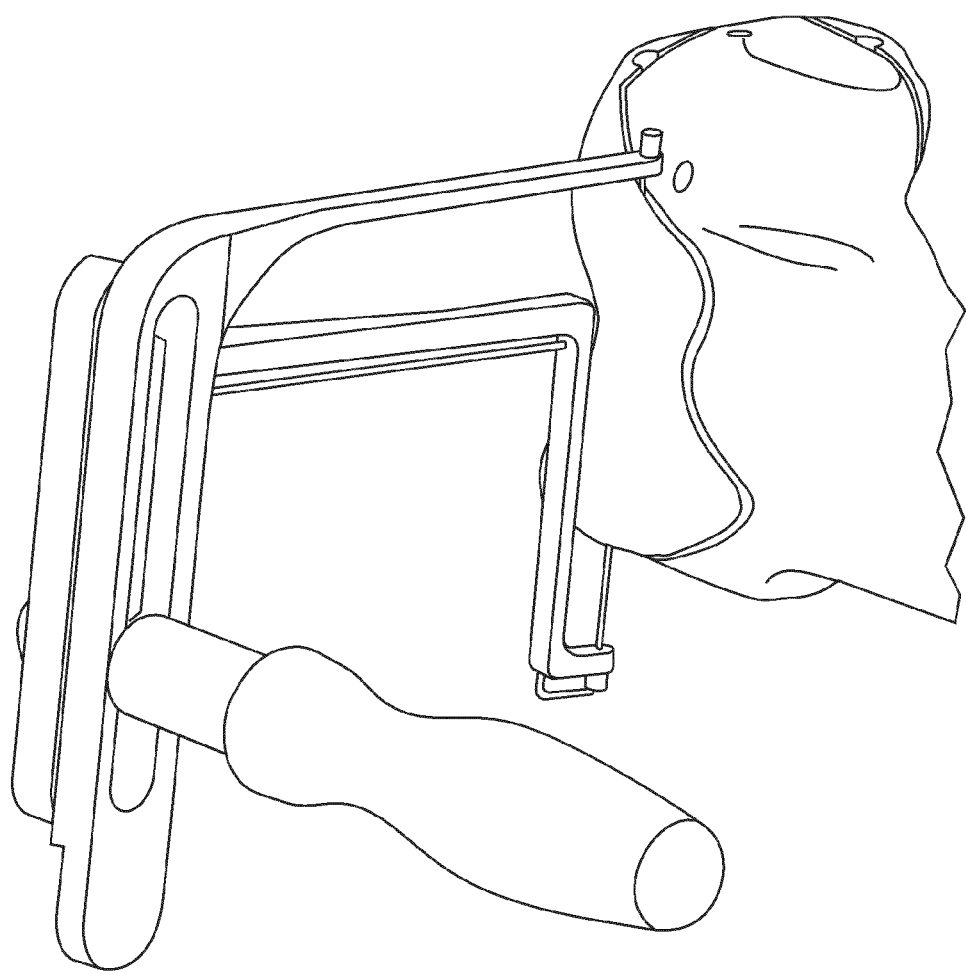

In operation, the handle is manipulated to traverse the cutting path of the cutting guide while the tibia is swung through a range of motion about the femur. This particular principal of operation takes advantage of the fact that the capsule, the patella, and to a lesser or greater extent the skin, moves with the tibia as it moves through a range of motion with respect to the femur. Thus, a small, perhaps 4 mm, stab wound through skin to the medial side of the posterior femoral condyles (roughly in line with the axis of the cutting tool shown in FIG. 60) with the knee bent in flexion, and then looked at the side of the femur (through the portal created by the stab wound) while moving the tibia through a range of motion, the side of the femur would be observed to be passing by/through the portal. In order to complete all of the resected surfaces on the femur necessary to fix a standard femoral prosthesis, it may be necessary in one embodiment to make two passes with the wire sweeping about the femur with the tibia as represented in FIGS. 71 and 72.

Figure 27:
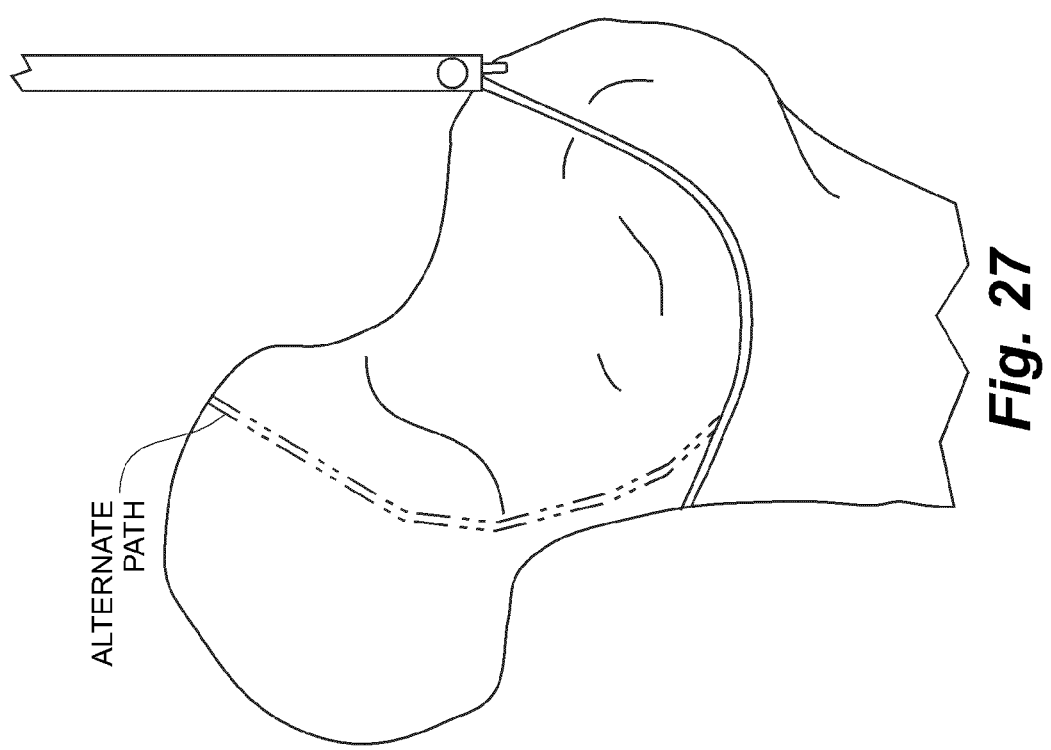
Figure 28:
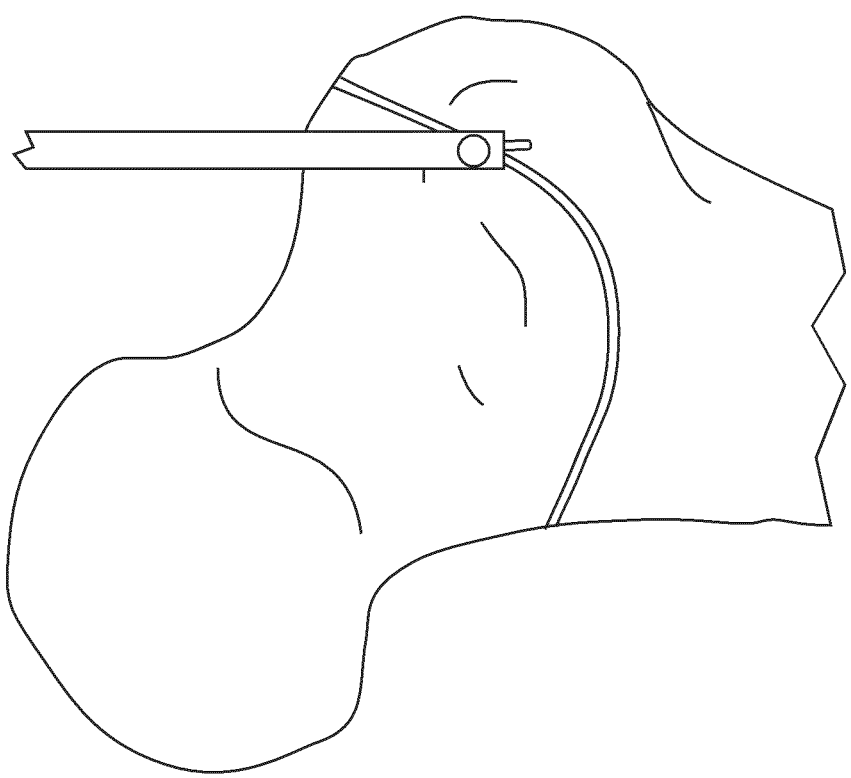
Figure 29:
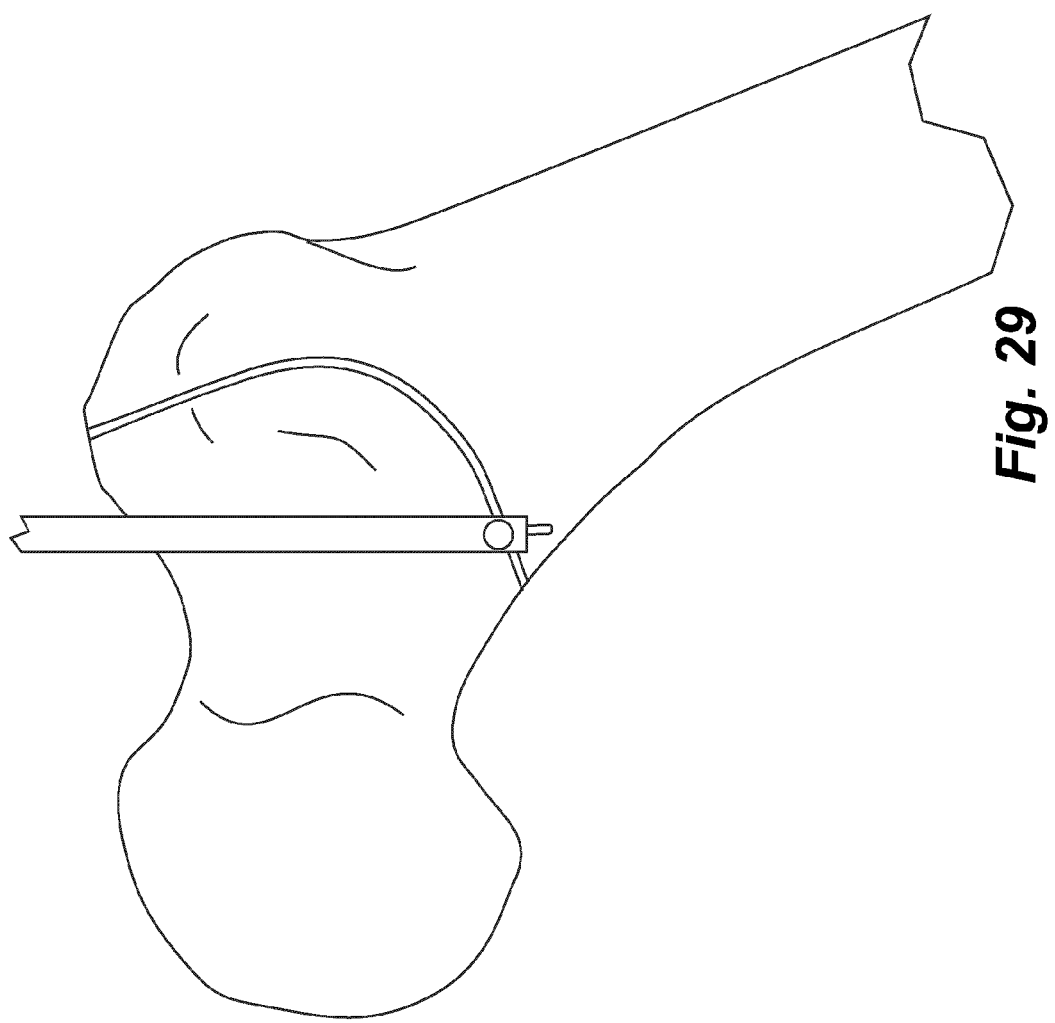
Figure 30:
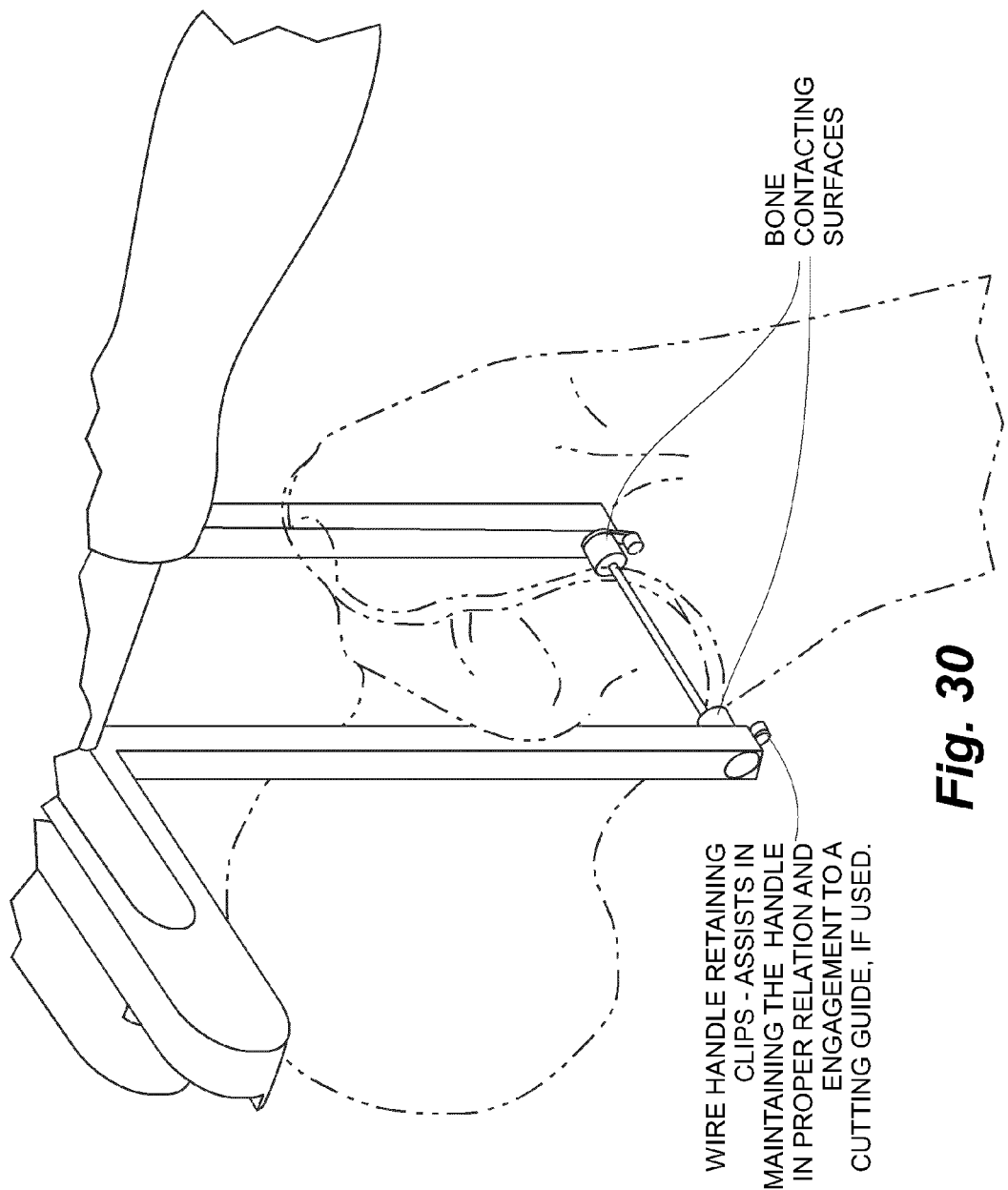
Figure 33:
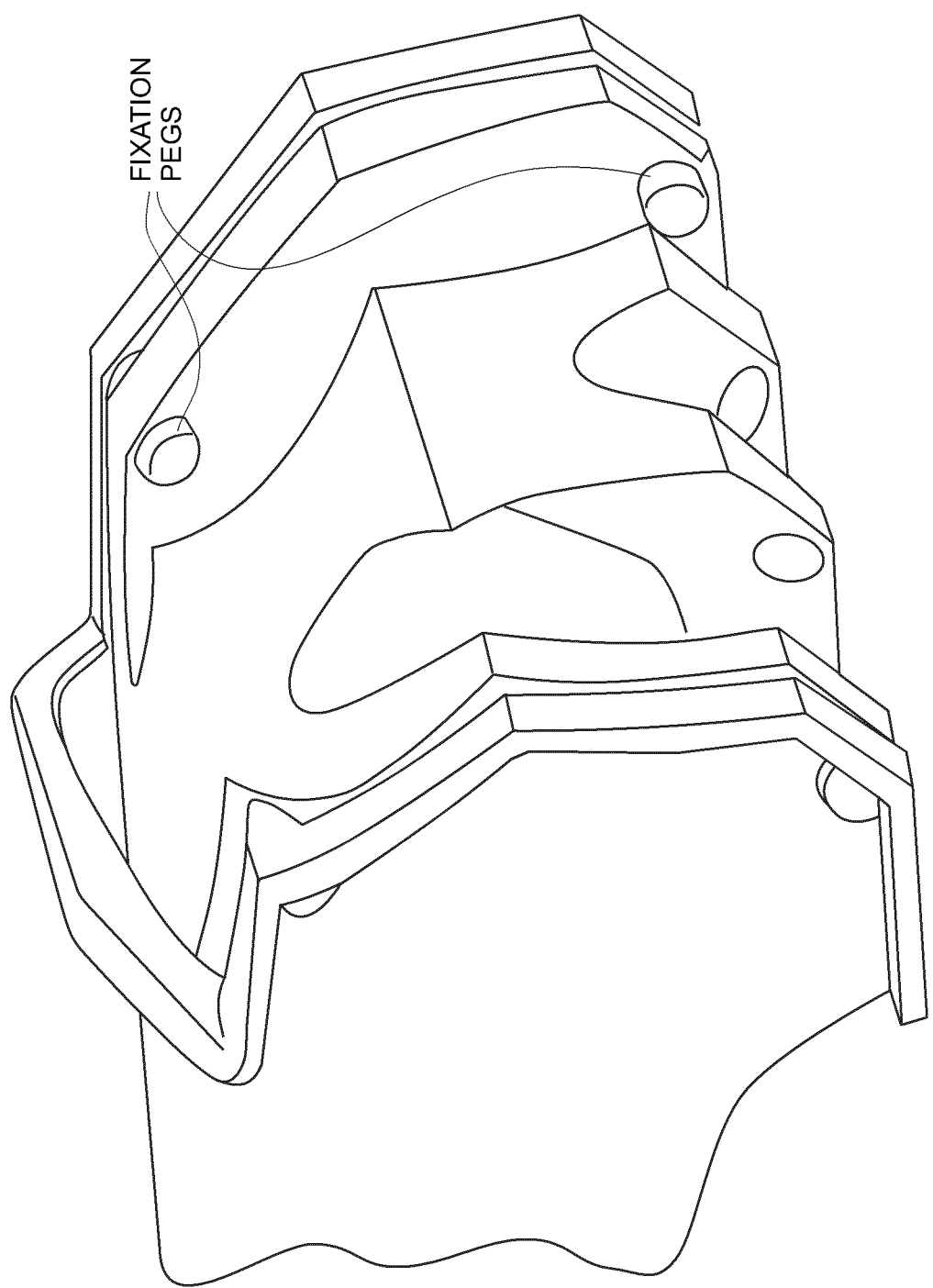
Figure 34:
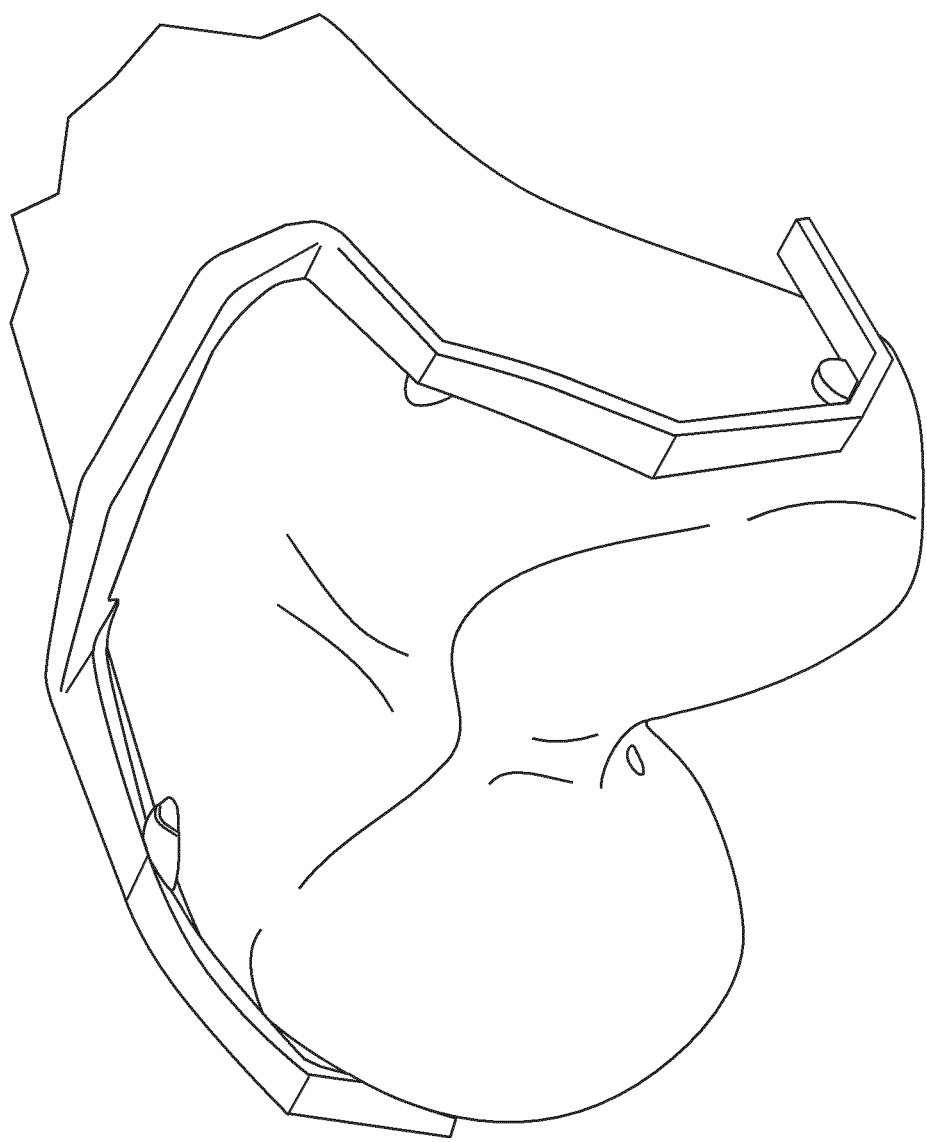
Figure 35:
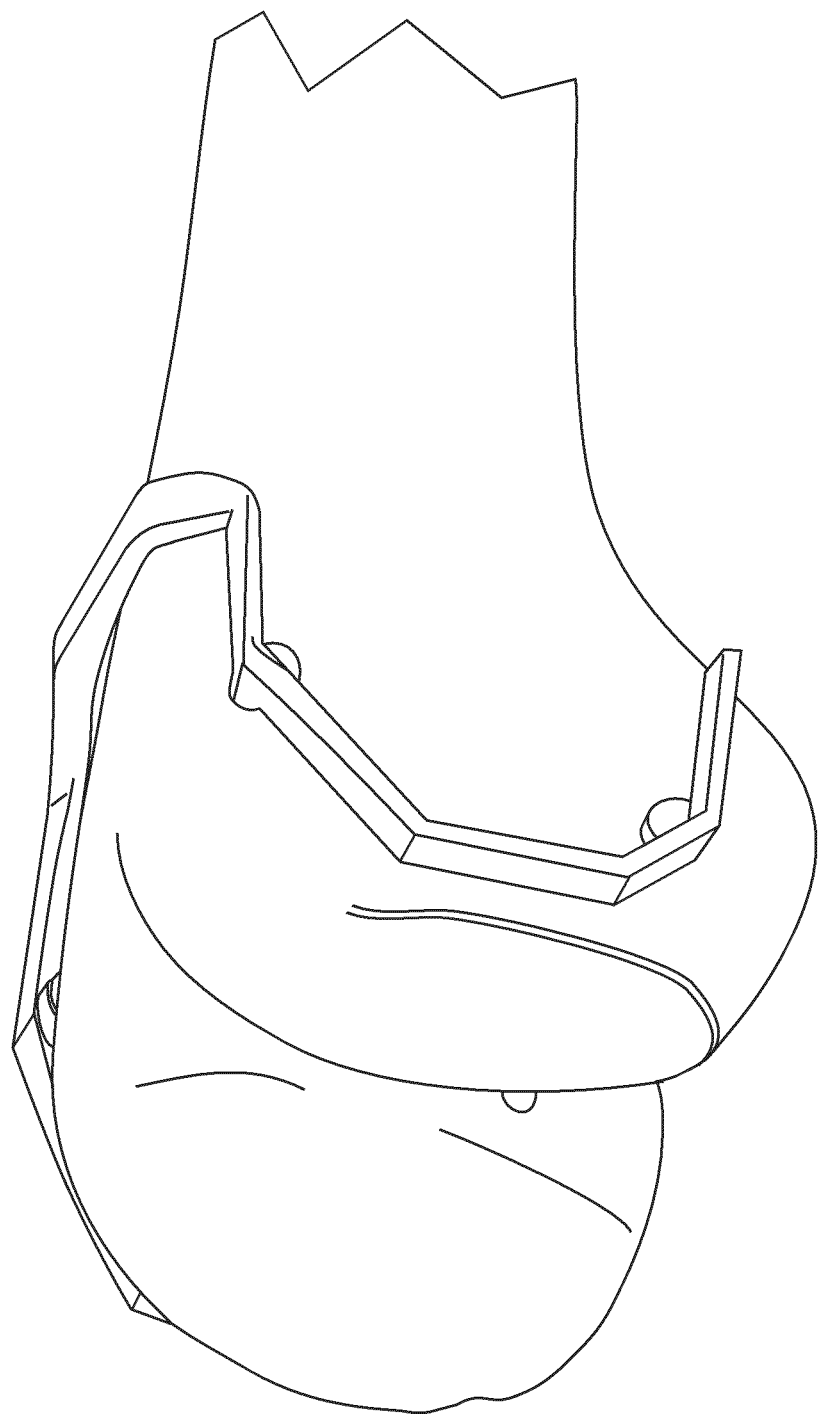
Figure 36:
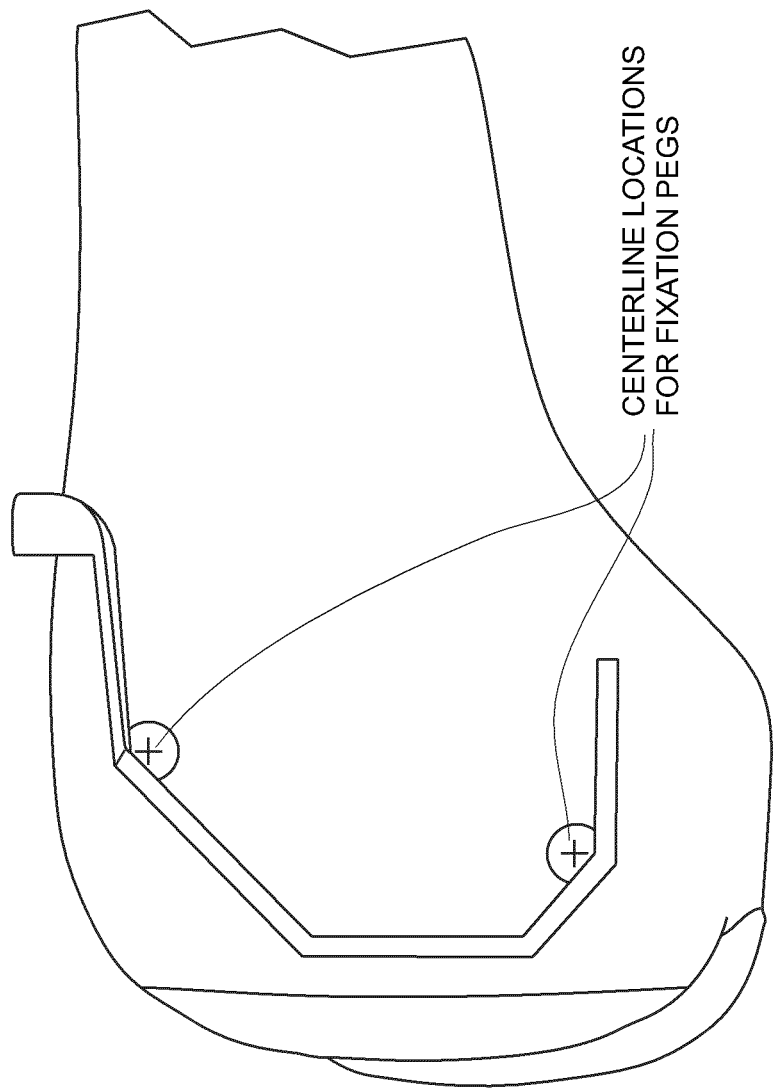

FIGS. 22-31 show an embodiment of the present invention for use in either freehand or guided resection of the proximal femur in total hip arthroplasty. Despite fairly large variations in the width of the resected surface along the cutting path of the surface, the contact surfaces of the handle remain in contact with the bone during freehand use. As noted herein, this is key in both minimizing the size of the incision necessary to allow passage of the tool into the wound and throughout boney removal and in preventing the wire from contacting soft tissue. In guided use, a pair of guide surfaces could straddle the boundary of the resected surface to be created similar to the guide shown in FIG. 33, but in the hip replacement application it may be desirable to mount the 'rails' on a pivoting mechanism, similar to a pair of pliers. Importantly, the cutting path of this kind of cutting guide preferably needs to geometrically correspond to the cut surface to be created. This correspondence can be described as having the guide surfaces being offset from the resected surface by an amount equivalent to the distance between the engagement surfaces of the handle (that contact the guide), and the cutting profile of the wire. It should be noted that the guide can be slotted, in which case the retaining clips shown in FIG. 25 may not be necessary. FIG. 27 shows an alternate cutting path "ending" that allows for complete, or nearly complete femoral preparation without removal of the femoral head from the proximal femur. As limb length discrepancies are a leading cause of problems encountered by orthopedic surgeons, determining head and neck sizes, lengths, and orientations prior to removing the only direct reference to the relationships between final implant location and the preoperative state would be helpful. In other words, the femoral canal could be fully or partially prepared to receive the femoral trial stem, the trial stem inserted, fluoroscopic measurements taken of the trial location and orientation (which is the best predictor of final implant location and orientation), the desired neck length and orientation calculated, and then the femoral neck could be completely resected. This should be extremely useful in avoiding limb length discrepancies, and should not burden the workflow of the procedure too harshly.

Figure 39:
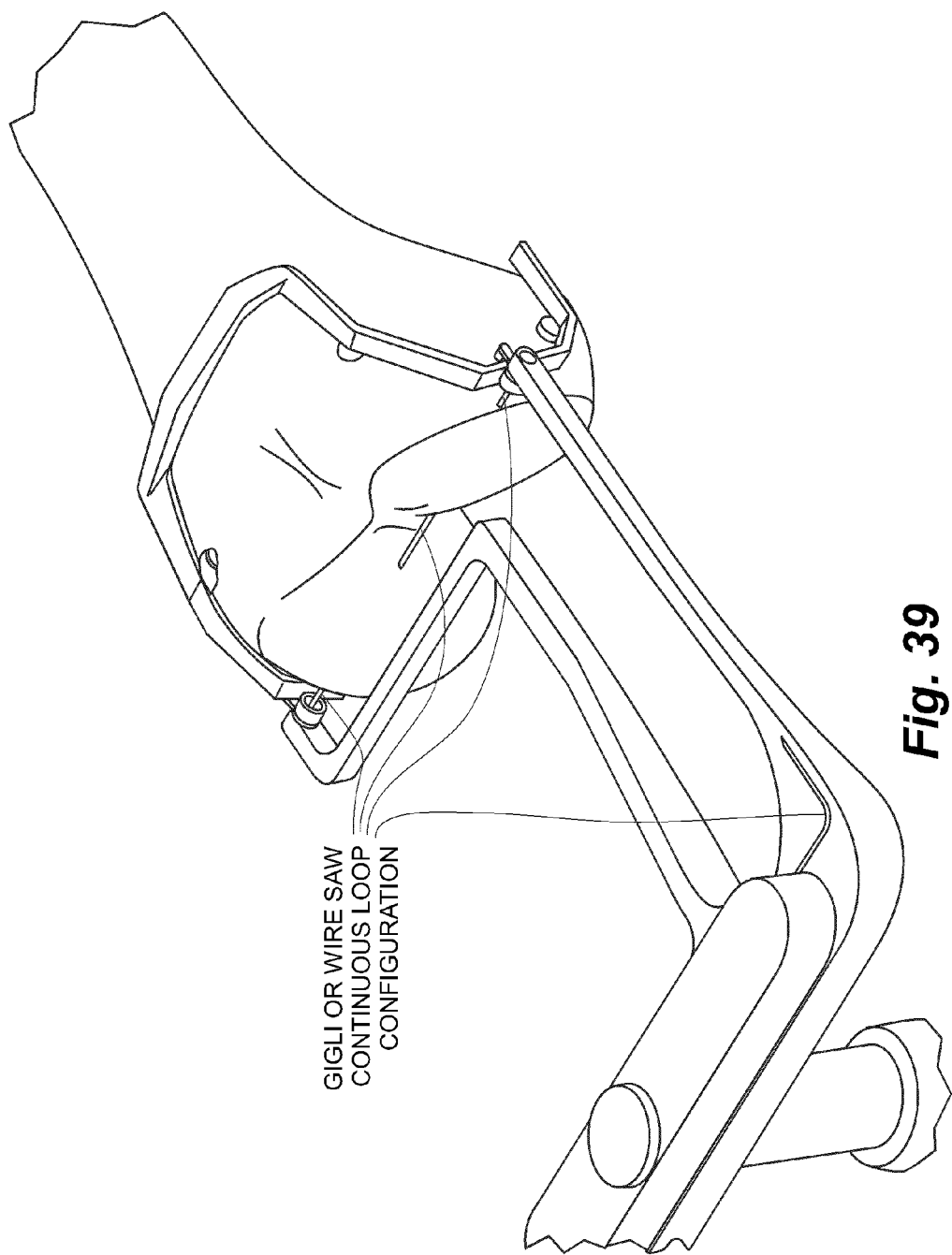
Figure 40:
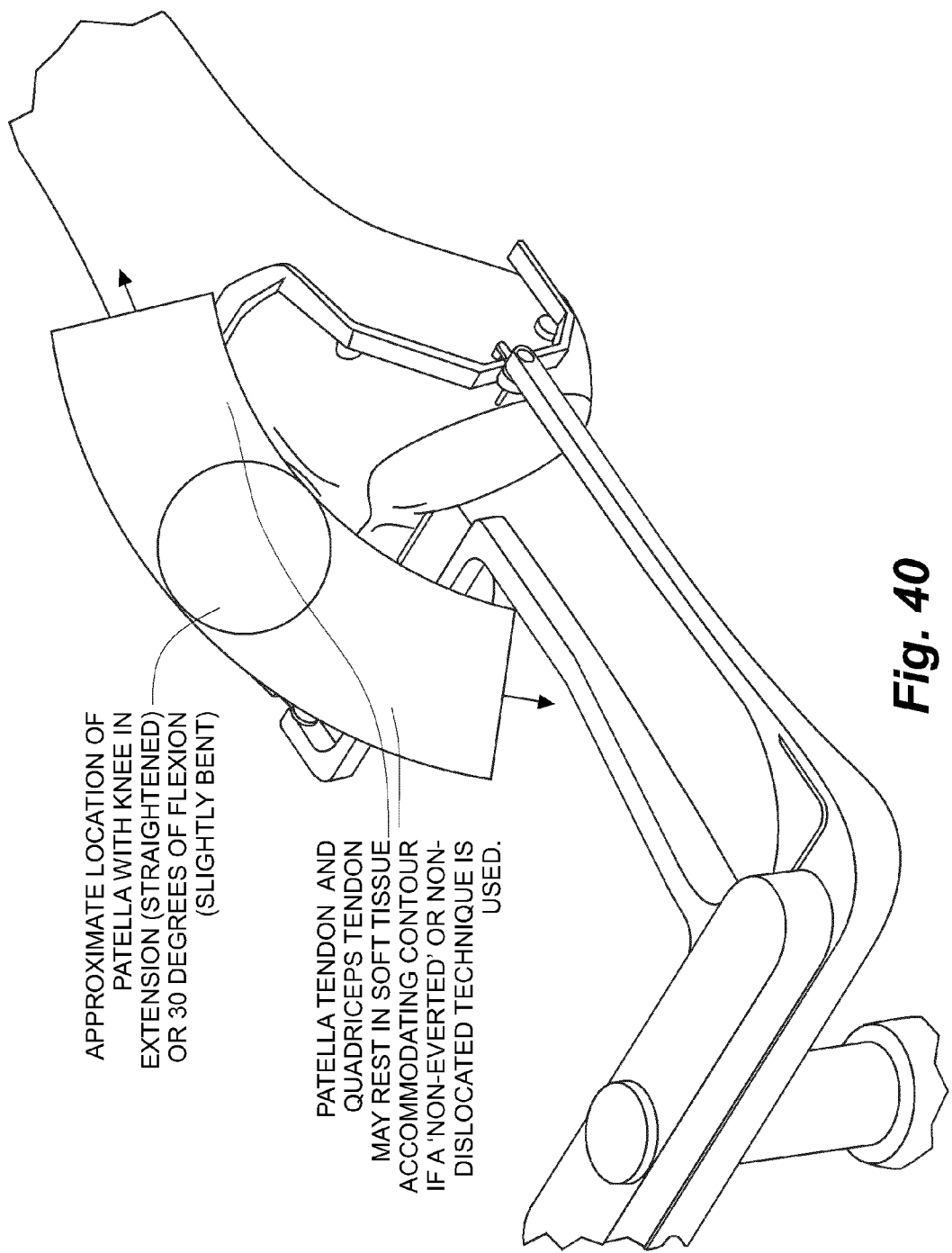

FIGS. 32-41 demonstrate another embodiment of the present invention. In this embodiment, an ultralow profile PBR guide is attached to preformed apertures or fixation bases located about the sides of the boundary of the resected surfaces to be created. It should be noted that the guide can be attached to apertures or fixation bases located to the lateral side of the medial condyle and the medial side of the lateral condyle, thus maintaining the stability of this mode of fixation while minimizing displacement of soft tissue during the insertion of the guide into the wound and during use. The mediolateral width of the guide surfaces shown in FIG. 37 preferably is no more than 6 mm and can be further reduced to as little as 1 mm, thus minimizing mediolateral soft tissue displacement. As seen in FIG. 40, guides of this kind can be utilized in lateral surgical approaches as well as more standard medial or medial parapatellar approaches. Importantly, the guide surfaces for the posterior cut, posterior chamfer cut, and/or distal cut can all be positioned between the side of the bone and the corresponding collateral ligament(s). This is helpful in avoiding contact between the wire and the soft tissues of the knee joint. While it may be helpful to utilize a retractor to prevent contact between the wire and the posterior cruciate ligament (PCL), clinical and cadaveric experience indicates that having cut the proximal tibia first, placing the knee in deep flexion (greater than 100 degrees), and positioning the tibia as far posteriorly with respect to the femur as possible usually prevents contact between the cutter and the PCL. Of course the guide can also possess a stop feature preventing movement of the handle and cutter beyond a certain point on the posterior cut guide surface.

Another point of interest is that, instead of completing all of the cuts in one continuous pass, this guide can be adapted to perform resection in a more incremental manner that can facilitate even less invasive surgical techniques. For instance, a single ultralow profile PBR Guide can be configured to only cut the posterior cut, or alternatively the posterior cut, posterior chamfer cut, and a portion of the distal cut. With the proximal tibia cut and the posterior femoral condylar surfaces cut (and the bone chunks removed from the wound), up to a 25 mm gap has been created between the proximal tibial cut and the posterior femoral cut. Thus, if these cut tibial and femoral surfaces are brought into contact with each other, the soft tissues of the knee joint are amazingly lax allowing for easy insertion of subsequent alignment guides, cutting guides, handles and cutting tools, including the wire cutting tool of the present invention. Furthermore the remaining cuts (whether that be all cuts except for the already completed posterior cut, or all cuts except for the already completed posterior cut and/or posterior chamfer cut and/or the distal cut) can be performed with the knee joint in roughly 45 degrees to 15 degrees of flexion to further allow for additional laxity of the soft tissues of the knee joint, specifically the extensor mechanism (quadriceps, quadriceps tendon, patella, and patella tendon), thus facilitating ease of implementation of the surgical technique. FIGS. 39 and 40 demonstrate the utility of the soft tissue accommodating eccentrically offset contour of the handle which facilitates ease of use without requiring dislocation or eversion of the patella. In comparing FIGS. 41 and 40, it is obvious that ultralow profile PBR guides used in conjunction with the handle and wire of the present invention will allow for dramatic reductions in the incision size necessary to accurately, precisely, easily, and inexpensively prepare the bones of a knee joint to receive prosthetic implants.

Figure 42:
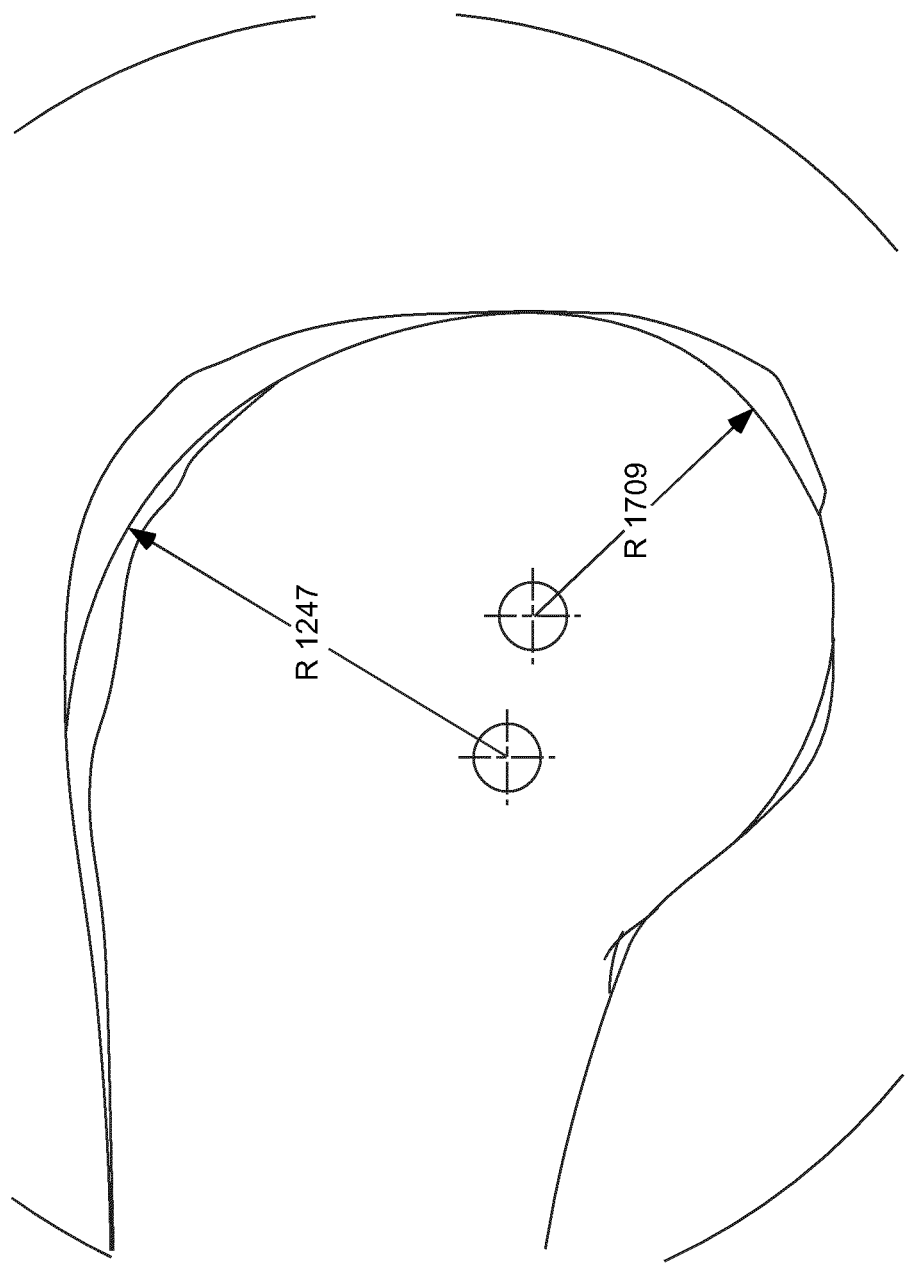
Figure 43:
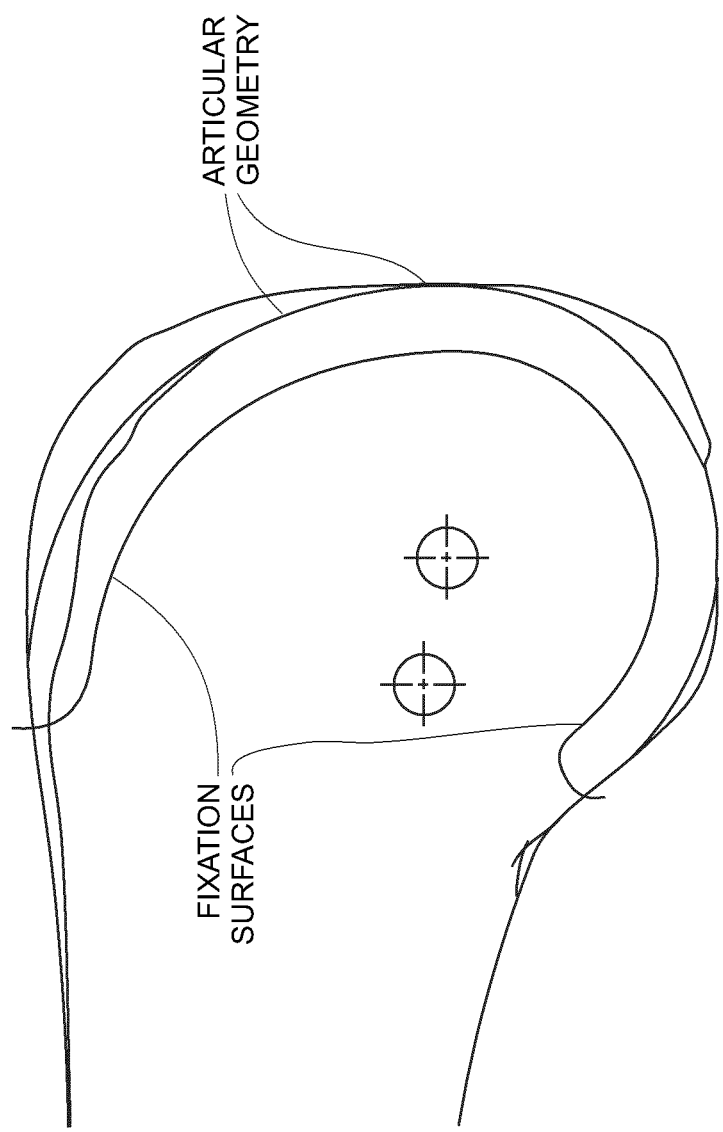
Figure 44:
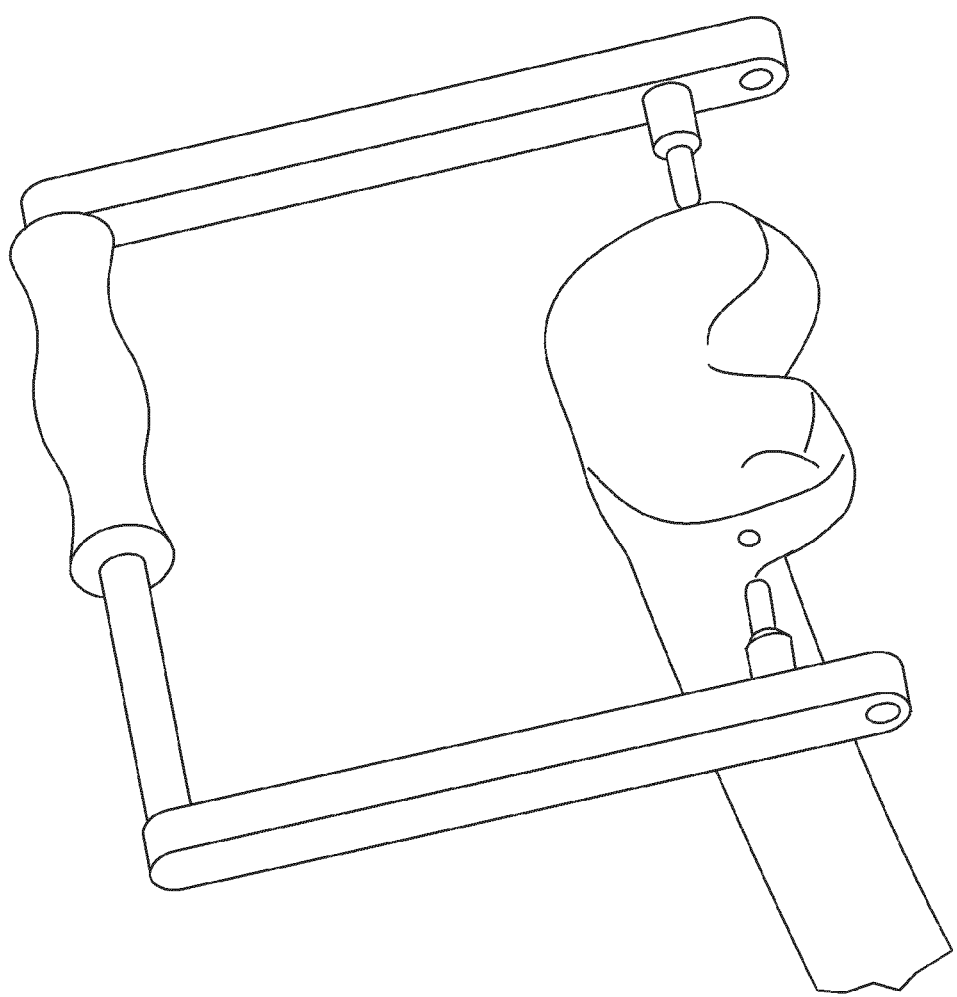
Figure 45:
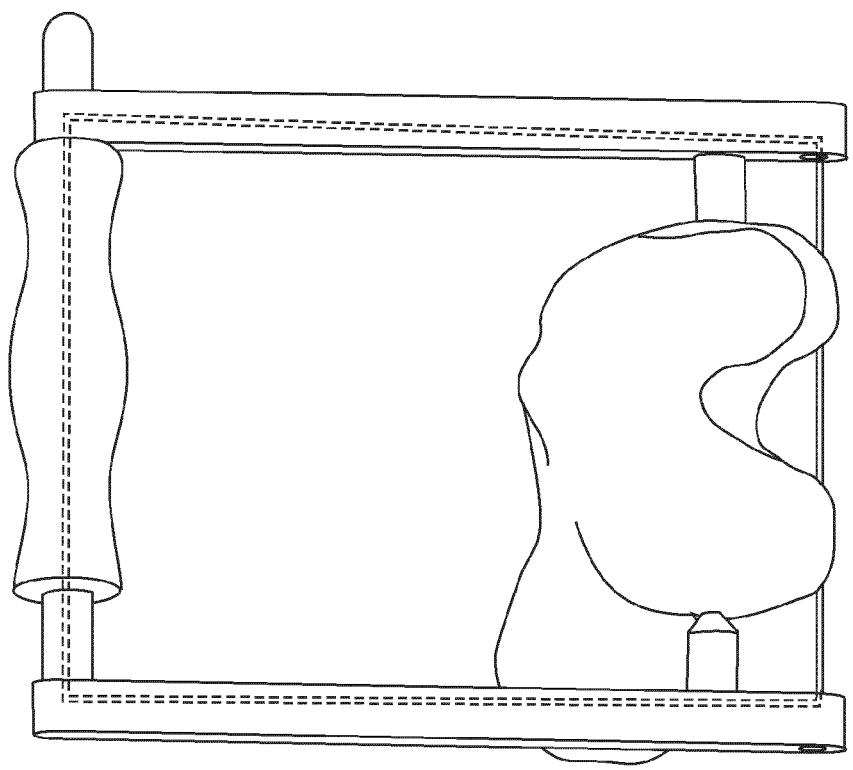

FIGS. 42-45 demonstrate another embodiment of the present invention for use in femoral resection and/or tibial resection. FIGS. 42 and 43 demonstrate that the natural articular geometry of the femur may be approximated by two tangent arcs, and that resected surfaces, and thereby the fixation surfaces can be correspondingly curved. FIGS. 44 and 45 show another embodiment of the handle of the present invention that is attached to apertures drilled in the bone or alternatively formed in a guide structure located about the sides of the bone, and where those apertures are both concentric to and coaxially aligned with the central axis of the arcs of the resected surface to be created. This can be extremely useful for use in conjunction with a Transcutaneous Transarticular TKA approach (TTTKA), where the aforementioned soft tissue protection sleeve embodiment of the present invention is a feature added to the handle shown in FIG. 45 to prevent or mitigate contact between the wire and soft tissue. Implementing a kinematic resection technique (a term describing cutting one bone of a joint while swinging the other bone or bones through a range of motion about the first) with the TTTKA technique enables absolute minimal soft tissue exposure or intraoperative trauma, as noted previously. As the radius of the arcs shown in FIG. 43 may change in size across implant sizes, the handle or handles preferably possess fixation nubs (perhaps better referred to in this embodiment as pivoting nubs) at multiple distances from the cutting profile of the wire. Further, although the arms of the handle shown in FIGS. 44 and 45 are straight, they may be curved or bent in any configuration to accommodate soft tissues and boney geometry of the knee joint whether arms are located partially or completely outside of the surgical exposure to the joint, or whether they are located within the exposure entirely. Specifically, the portion of the arms distally of the pivoting nubs can be configured to reach within the incision of a medial parapatellar exposure, a more medially offset exposure, or analogous exposures to the lateral side of the joint.

It should be noted that the cuts resulting from the techniques discussed result in cylindrical cut surface creation, but that the handle can be modified such that the axis of the pivoting nubs and the axis of the wire suspended between the distal ends of the handle are angled with respect to each other to enable the creation of cut surfaces that are frustoconical, resembling a section of a cone, rather than cylindrical surface. As the lateral condyle, both distally and anteriorly, tends to have a larger radius or radii than the medial compartment of the knee joint (somewhat shown in FIG. 42), this enables implant designs minimizing the quantity of viable boney material removal while facilitating appropriate implant fixation.

It will be noted that such frustoconical resected surfaces can be resected so as to mate with correspondingly frustoconical fixation surfaces of an implant, thus creating a progressively greater interference fit between the implant and the bone as the implant is contacted to the cut surfaces and moved laterally across them under force to achieve press-fit. An exemplary embodiment of an implant that utilizes such an interference fit with frustoconical resected surfaces is shown in FIG. 77. This embodiment is especially useful in medially oriented, less invasive surgical exposures where the ability to insert and impact the implant in a distal to proximal direction is problematic due to soft tissue interference with implant placement. This same concept for implant design is beneficially applied to implants with flat fixation surfaces, or combinations of flat and curved surfaces where the mating fit between the implant and the bone is essentially a wedge of increasing interference or press-fit as the implant is moved laterally. It should be noted that this same embodiment can be applied to laterally oriented surgical exposures and adapted accordingly. Frustoconical or wedge like included angles between 1 degrees and 40 degrees will work well, but in the interests of bone preservation, included angles between 1 degrees and 20 degrees are preferred. These embodiments will significantly increase the ease of use of attaching femoral implants wherein the arc of the posterior femoral condyles extends beyond 30 degrees of arc past the contact point between the femoral and tibial components when the knee is bent to 90 degrees of flexion. It should further be noted that in one embodiment, the wedge is formed by an included angle between the anterior cut(s) and posterior cut(s) only whether they are flat or curved. It should be noted that the resected surfaces for use with this lateral interference technique may be generated by any embodiment of the wire cutting tool disclosed herein, or any resection means disclosed in the prior art, or even by simple modification of standard cutting block designs and alignment techniques. The pinplasty technique described in the provisional patent application previously incorporated by reference will also work well in creating such surfaces, as would all of the inventions contained in the following: U.S. Pat. Nos. 5,514,139, 5,769,855, 5,643,272, 5,810,827, 5,755,803, and U.S. Publ. Application No. US2002/0029038 A1.

Furthermore, as seen in FIGS. 42 and 43, the implementation of curved posterior cut surfaces enables excellent contact areas between the tibial and femoral implants in deep flexion. The extent of such contact areas between the tibial and femoral implants in deep flexion can currently, in terms of commercialized product, only be attained by implants such as the LPS HiFlex® sold by Zimmer, Inc., of Warsaw, Ind., which requires a dramatic posterior cut removing bone to a depth of somewhere between 12 mm to 19 mm deep because their posterior cut is flat and parallel in at least one plane to the mechanical axis of the leg. Curved resected surfaces enable the same benefits in terms of range of motion with excellent contact area (also referred to as conformity) while removing a total volume of living bone from the posterior condyles that is 50% or less than what is required by the LPS HiFlex®. This conservation of living bone not only leaves far more structurally and biologically viable bone available for any subsequent revision, but also conserves structurally viable cortical and dense subcondral bone which is superior for fixation when compared to the cancellous tissue to which the LPS HiFlex® more largely depends on for short and long term fixation during and after primary procedures.

Figure 46:
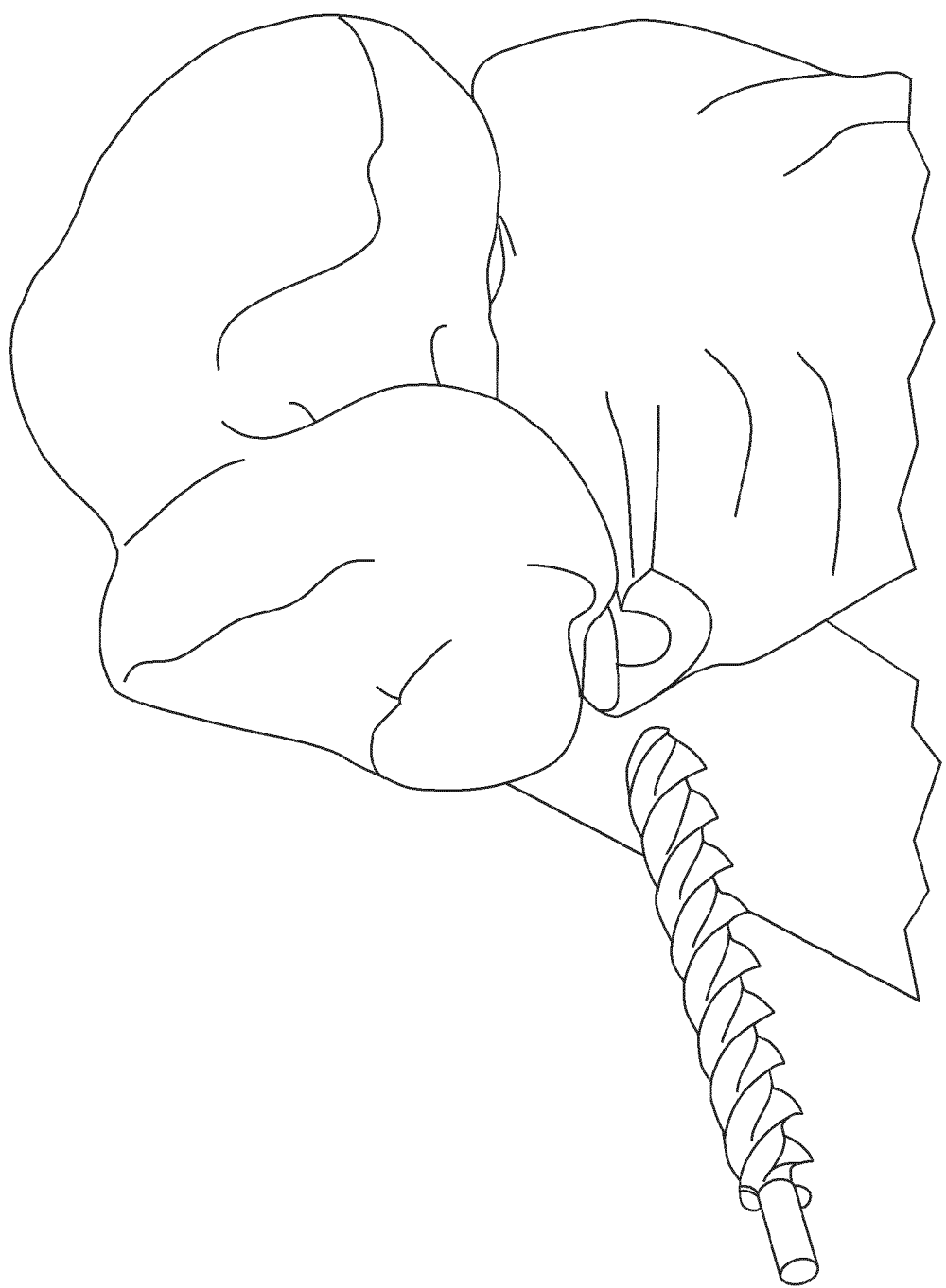
Figure 47:
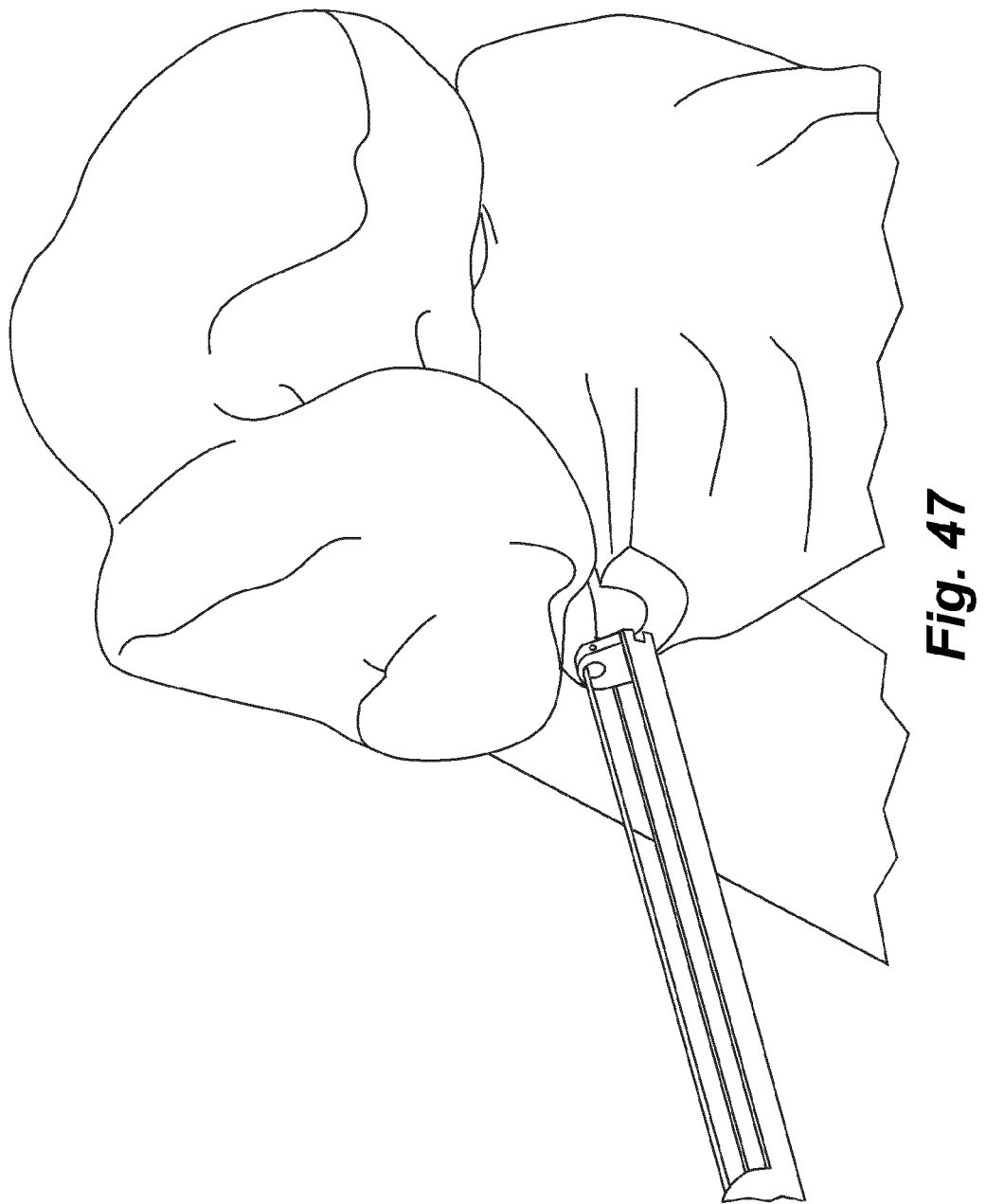
Figure 48:
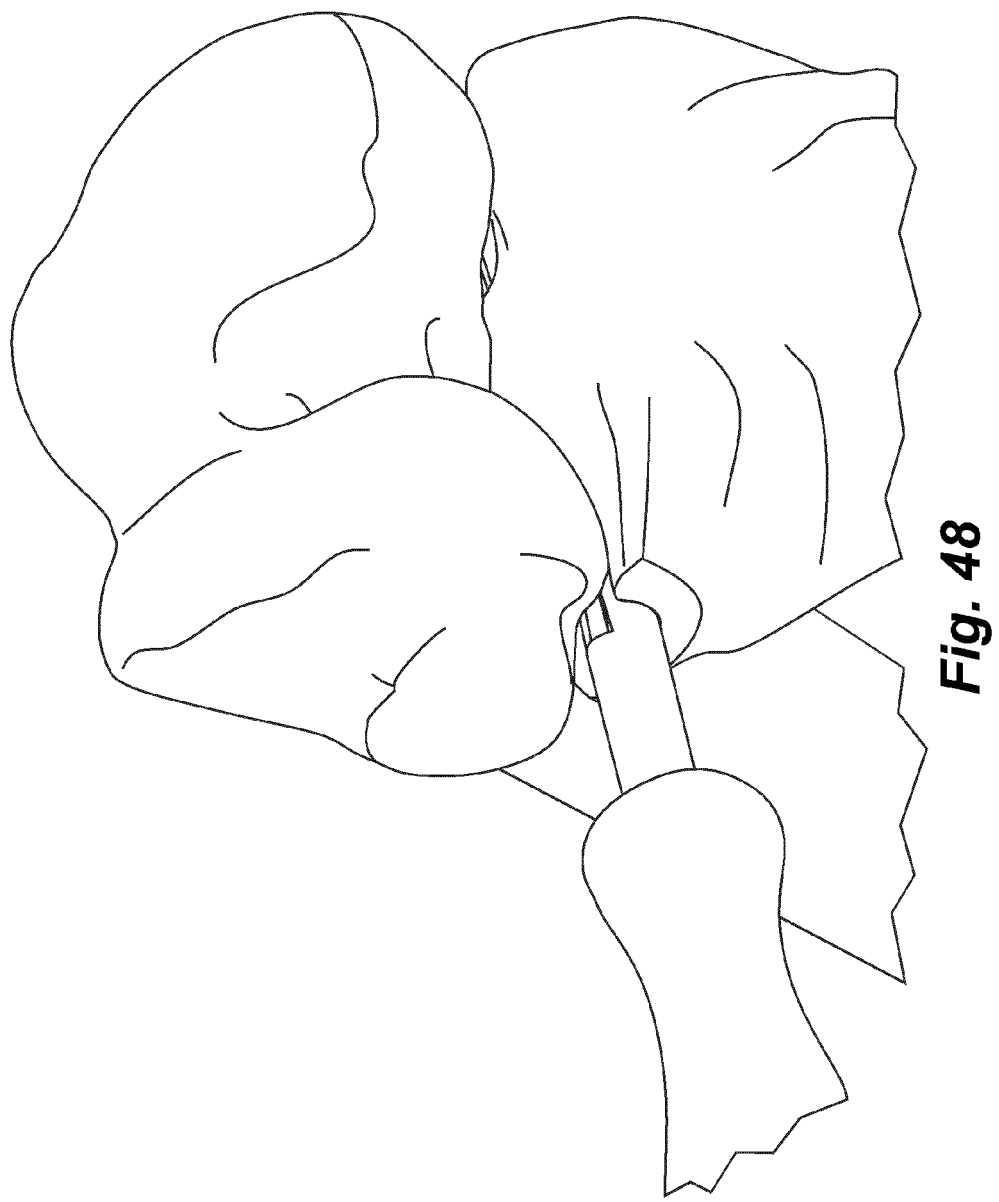
Figure 49:
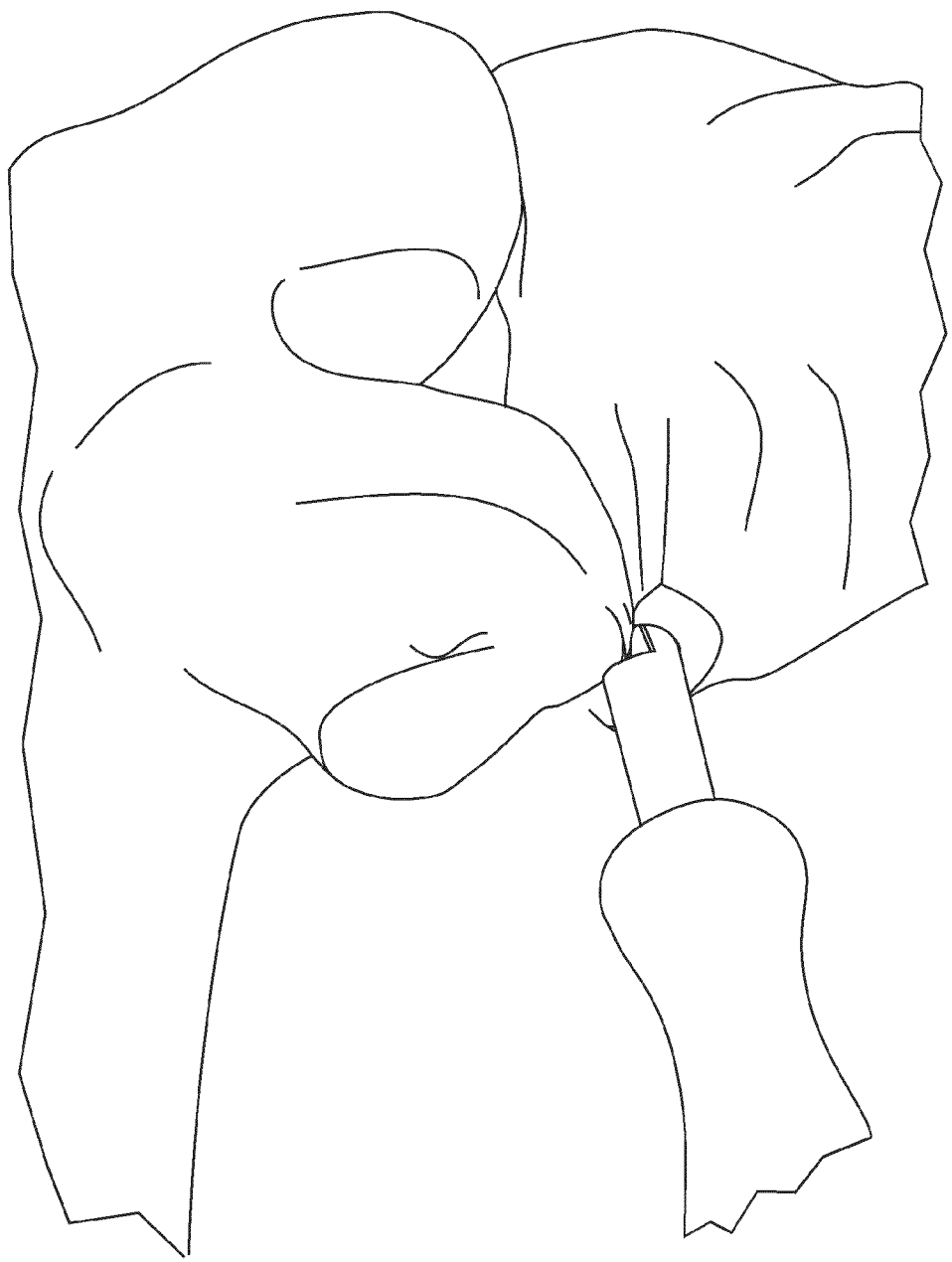
Figure 50:
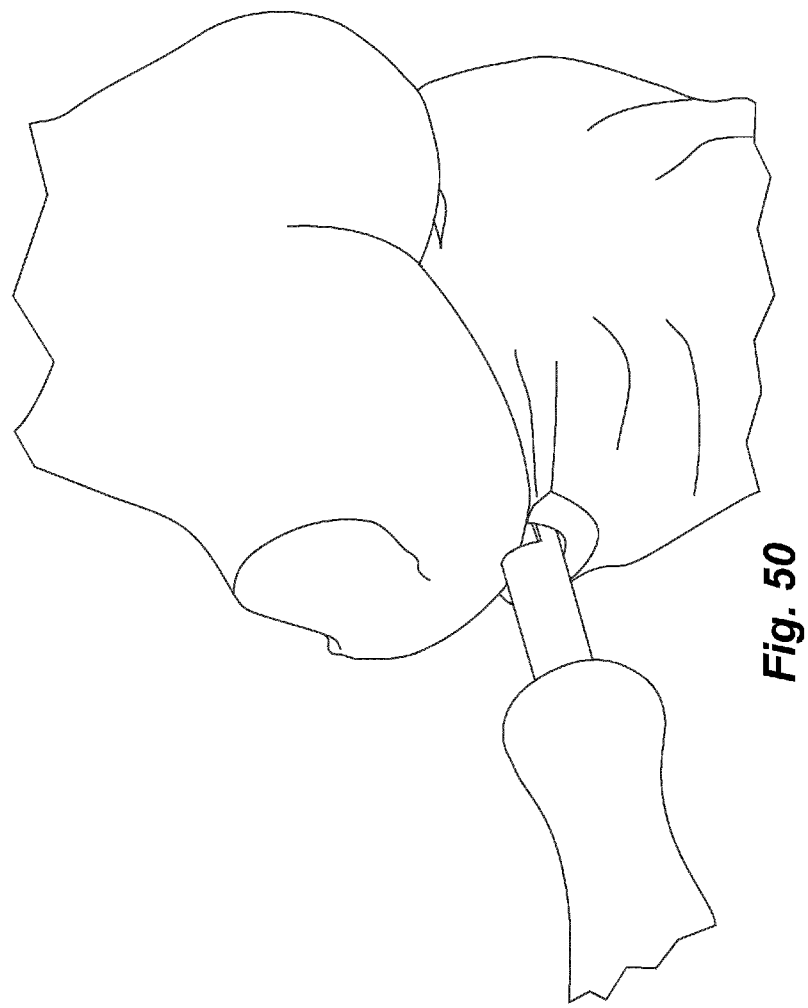
Figure 51:
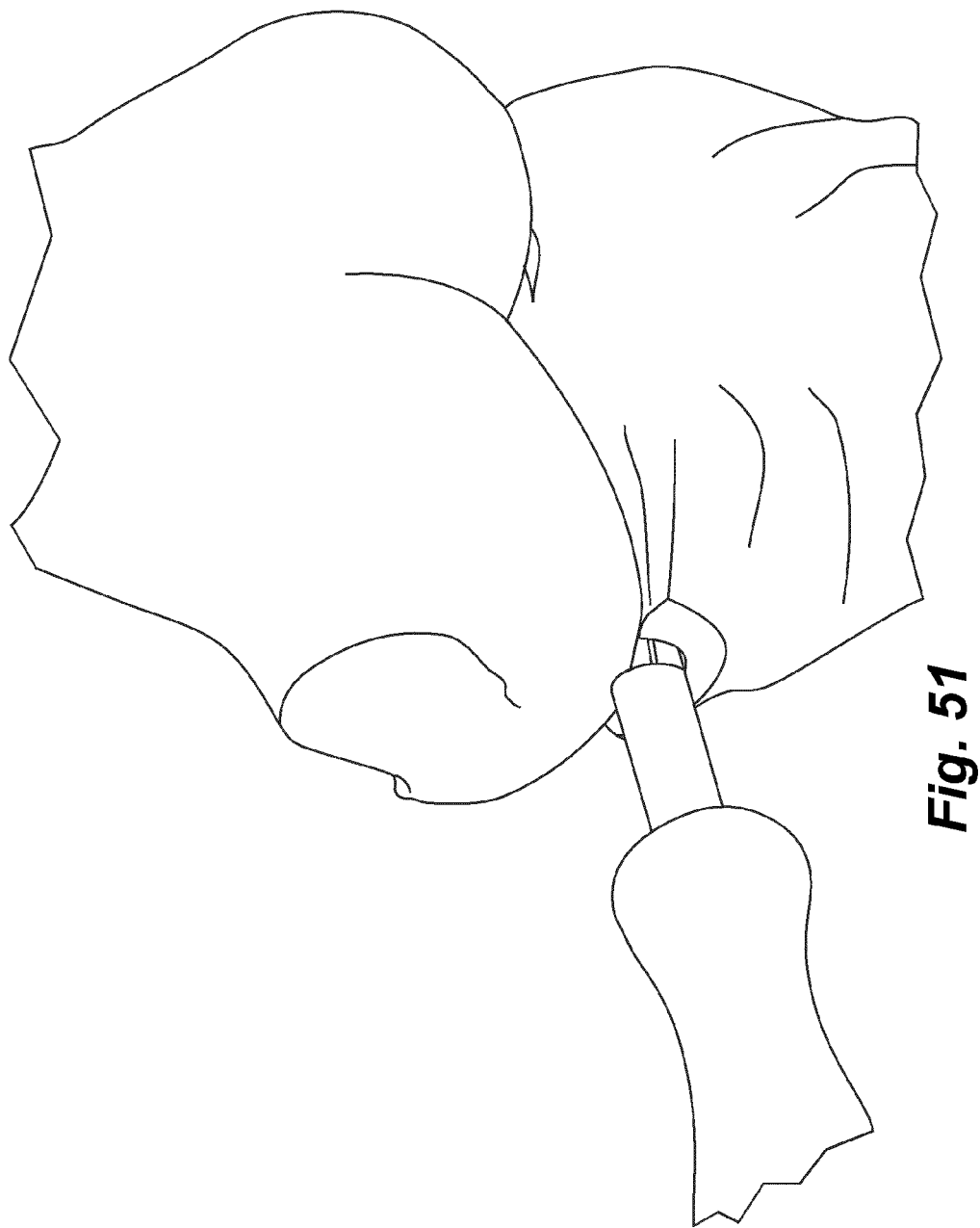
Figure 52:
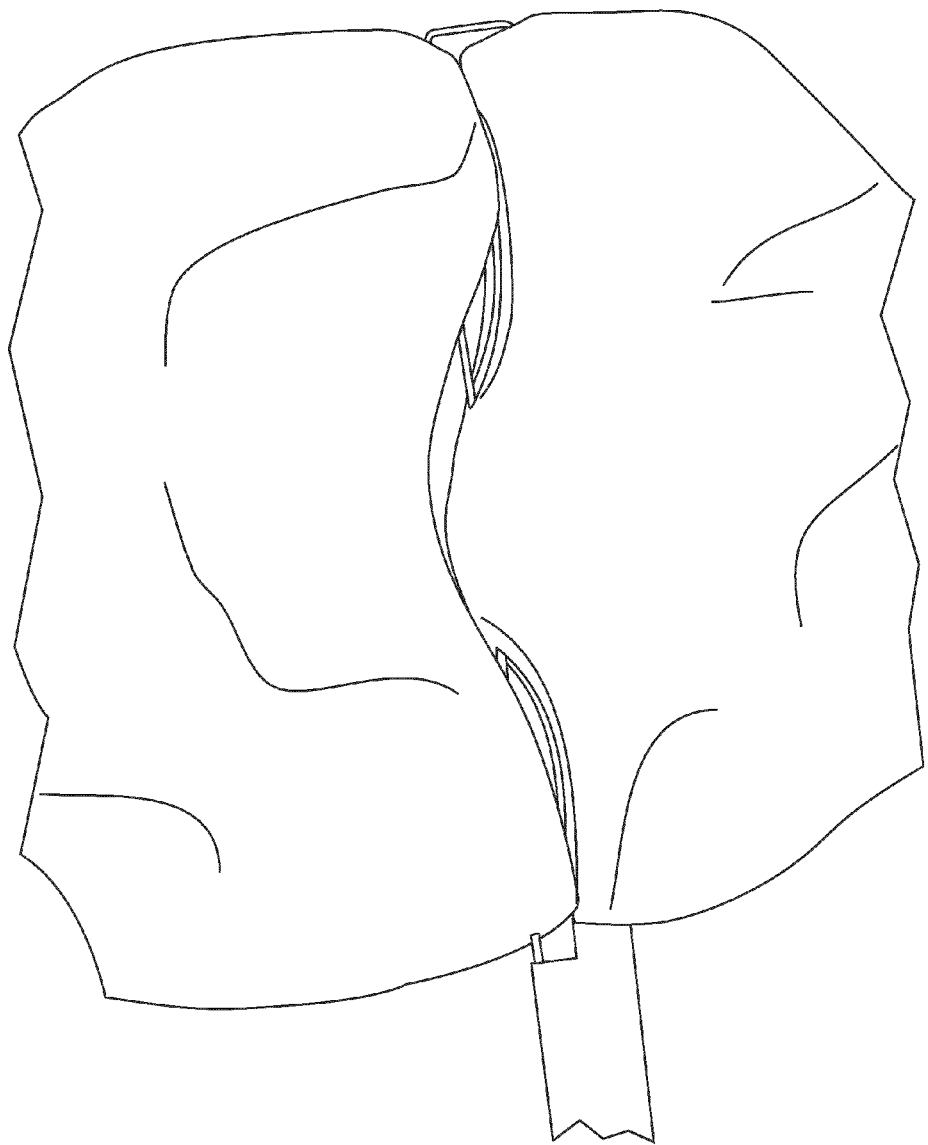

FIGS. 46-53 show an embodiment of the present invention for use in femoral resection, potentially in a modified form of TTTKA where the soft tissue portal is only created on one side of the joint. FIG. 46 shows a pilot drill that could be guided by manual or computerized alignment systems to create a hole in bone at or about the joint line. Another embodiment of the wire and handle of the present invention are then inserted across the joint as shown in FIGS. 47 and 48. A drive mechanism (not shown) is then connected to a manual or powered driver to drive the wire saw to cut bone while moving the tibia through a range of motion about the femur, as shown by comparing FIGS. 49 and 50. A simple twist of the handle, shown in comparing FIGS. 50 and 51 allows for completion of the condylar cuts shown in FIG. 53 (note the proximal tibia is represented as having been cut for the sake of clarity). As is evident by examining FIGS. 51 and 52, both the handle and the wire are almost entirely, and can be easily modified to be entirely, captured within a "tibial bone tunnel," which prevents any form of contact between the wire and soft tissue. Although use in this manner could be described as 'unguided kinematic resection,' an alternate embodiment modifies the embodiment shown to add a single or a plurality of engagement features to contact a cutting guide located about the sides of the knee with guide surfaces located outside of the wound, or guide surface(s) in the wound and outside the wound, or with guide surfaces located within the wound. Further, this embodiment or any embodiment of the current invention, with no or some modification, can be used in conjunction with the cutting guide inventions shown in the co-pending provisional application entitled, "METHOD AND APPARATUS FOR PINPLASTY BONE RESECTION," U.S. Provisional Application No. 60/536,320, the disclosure of which is hereby incorporated by reference.

Figure 53:
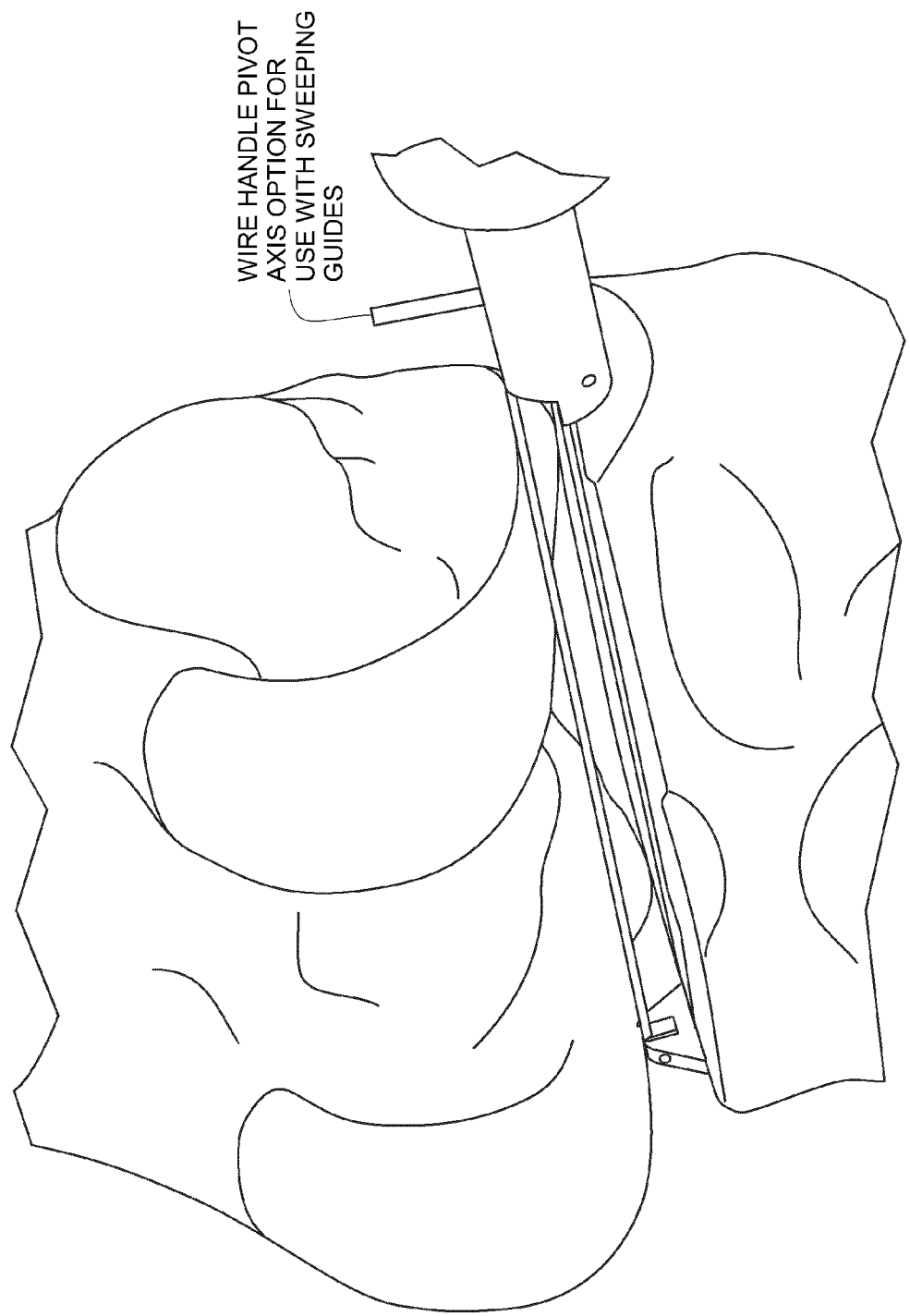
Figure 54:
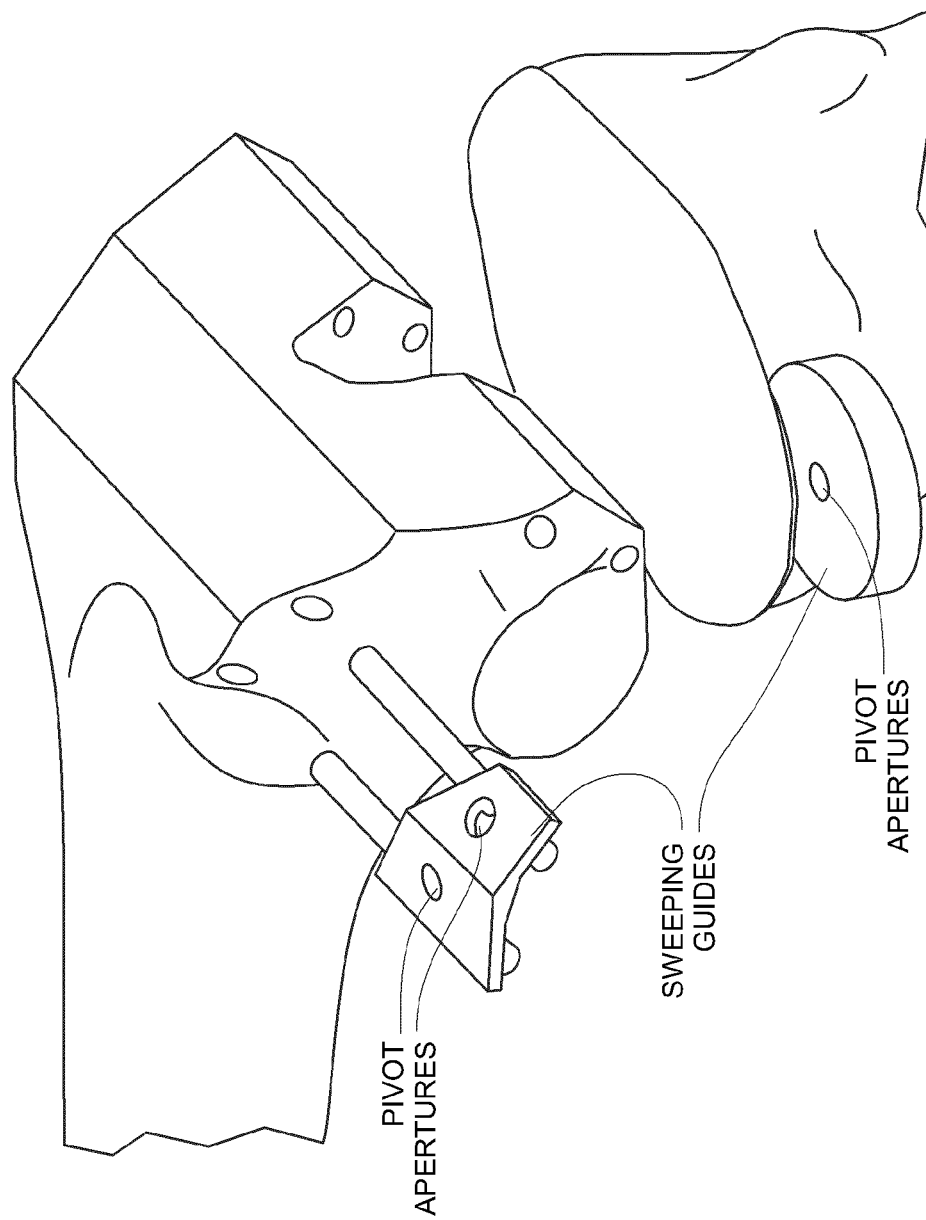
Figure 55:
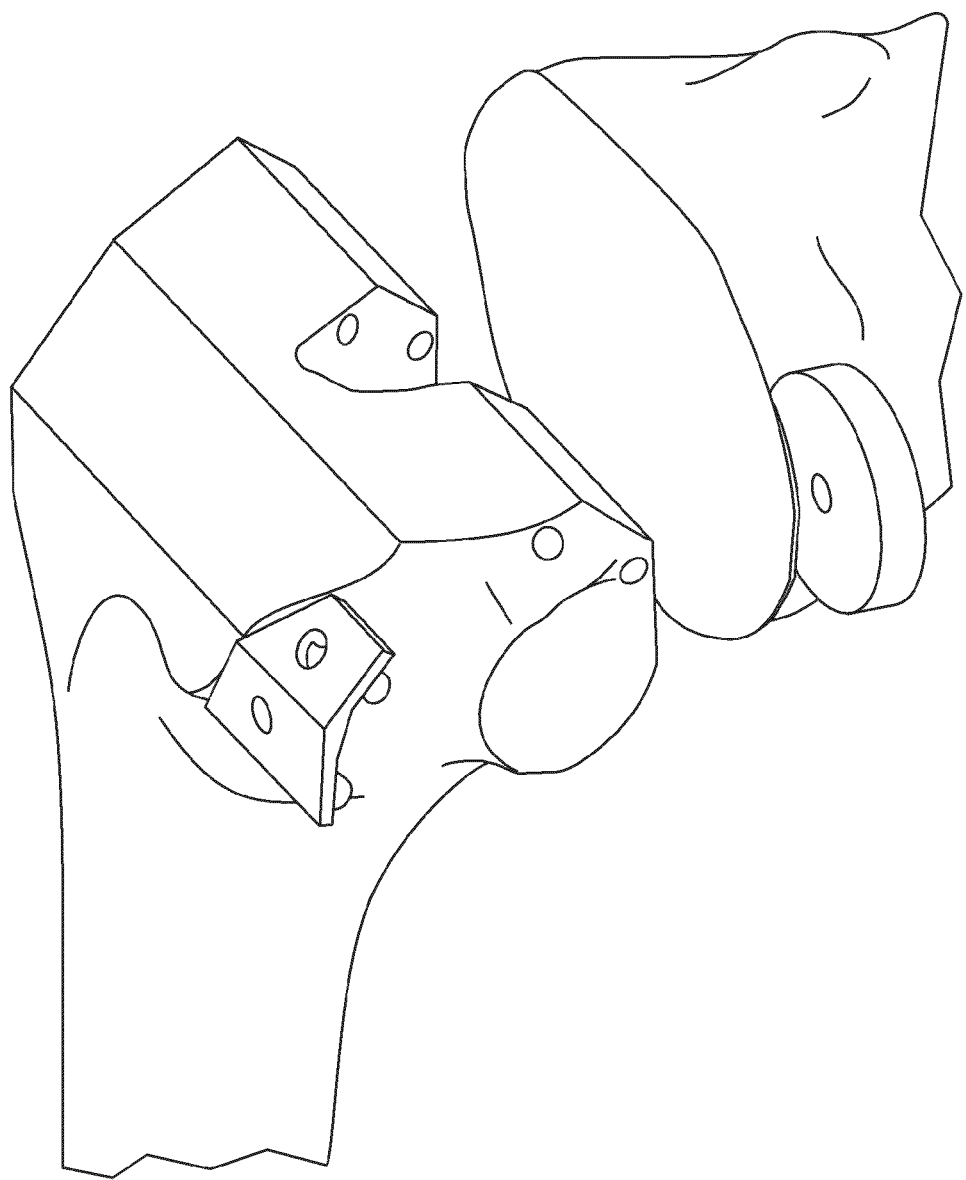
Figure 56:
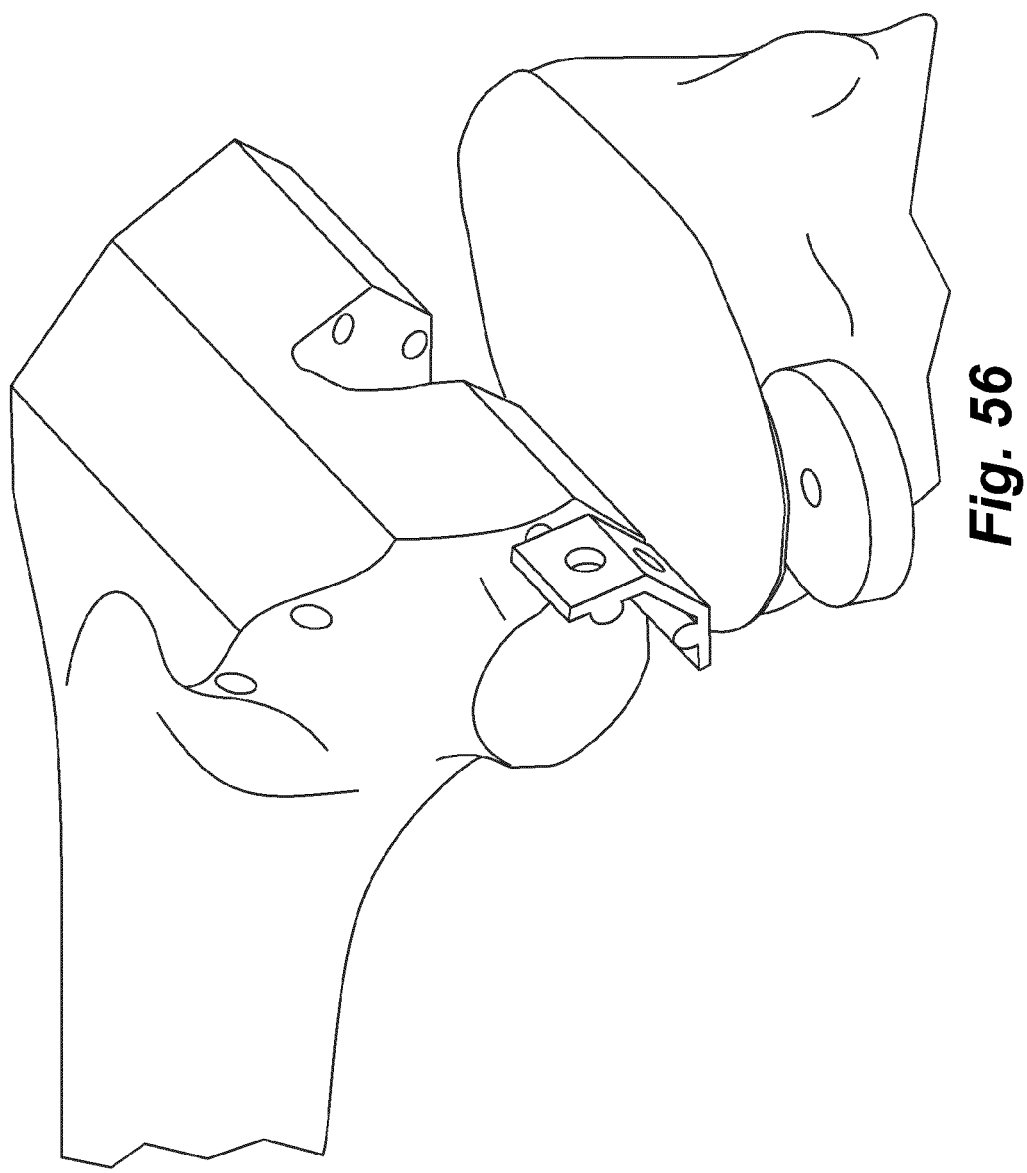
Figure 57:
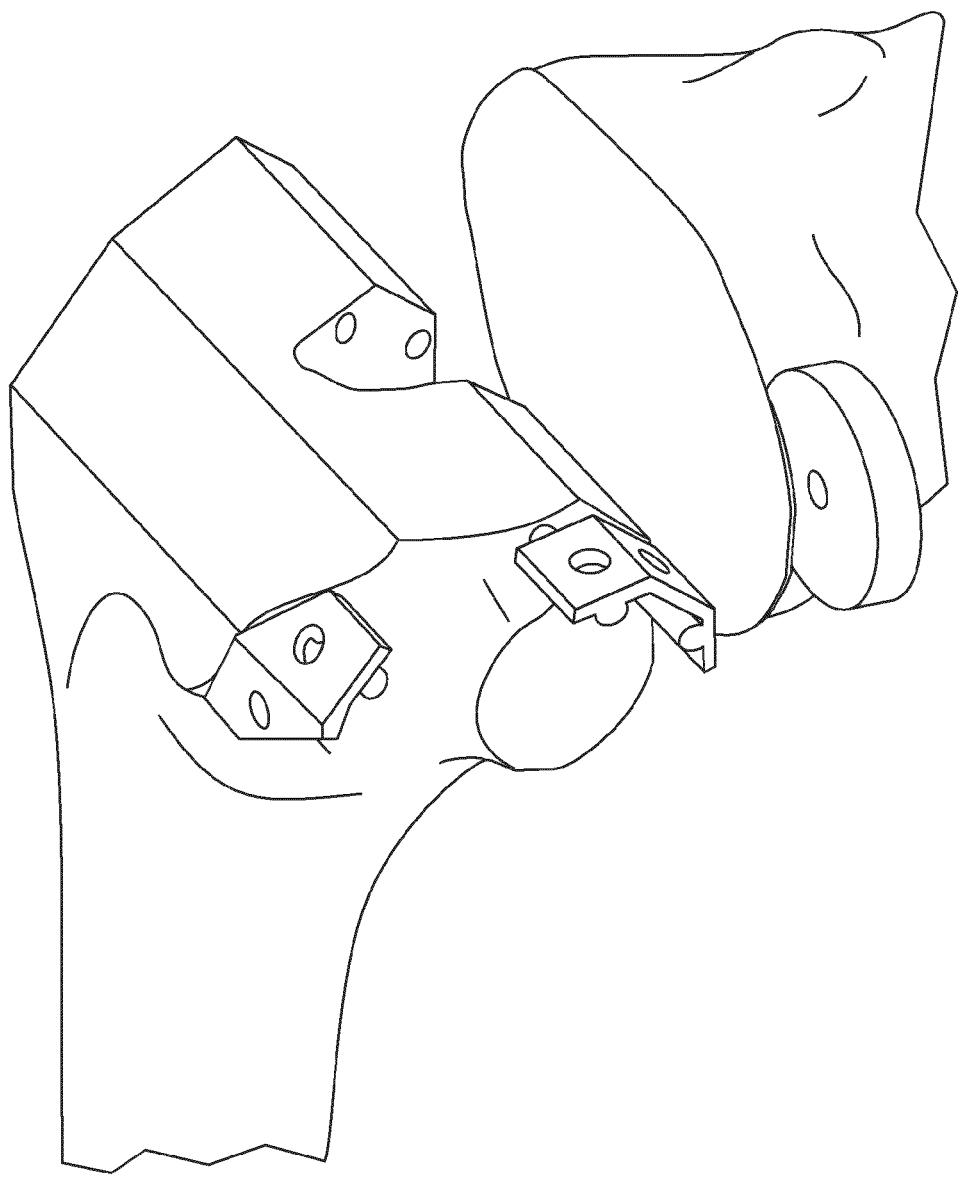
Figure 58:
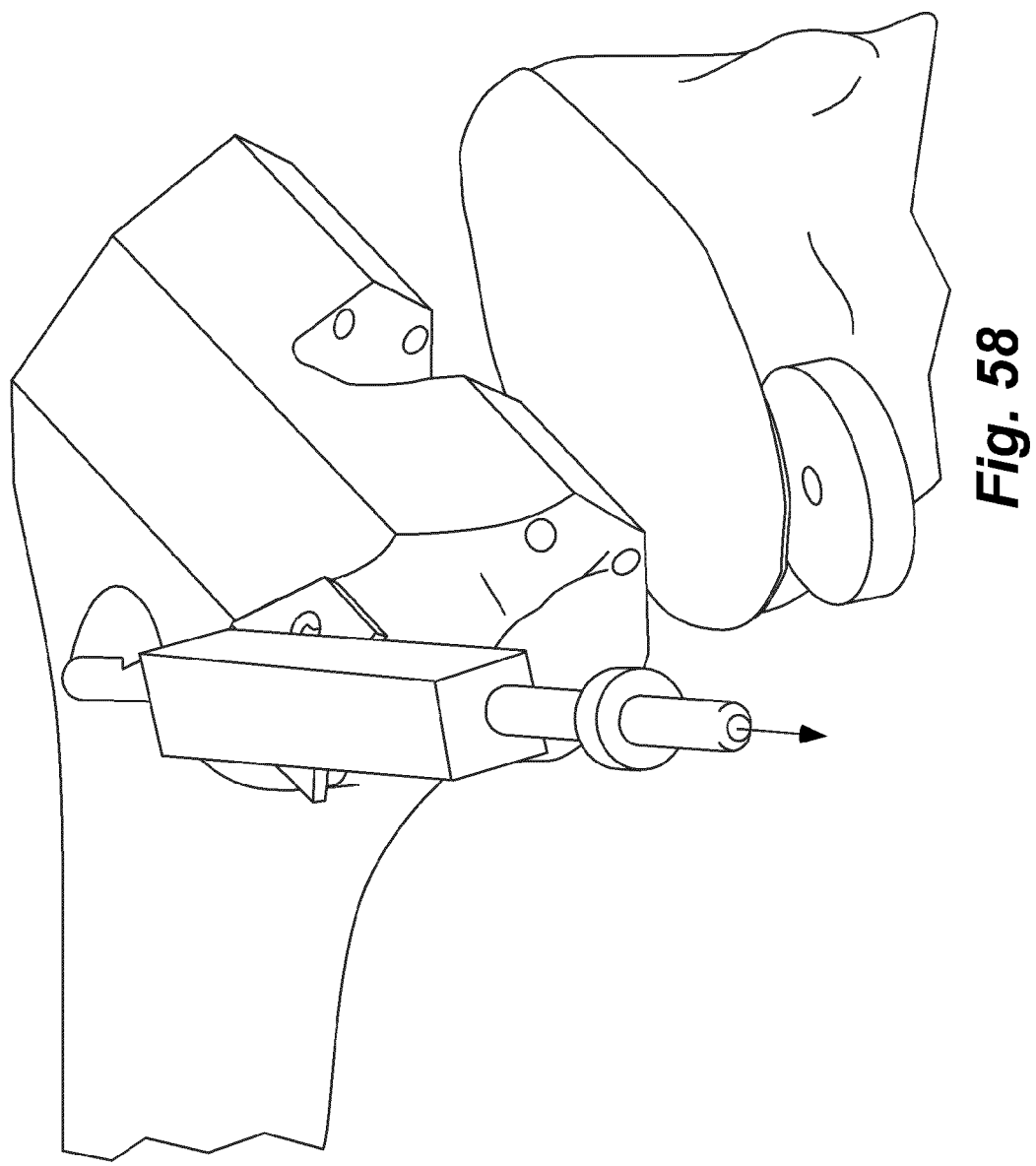
Figure 75:
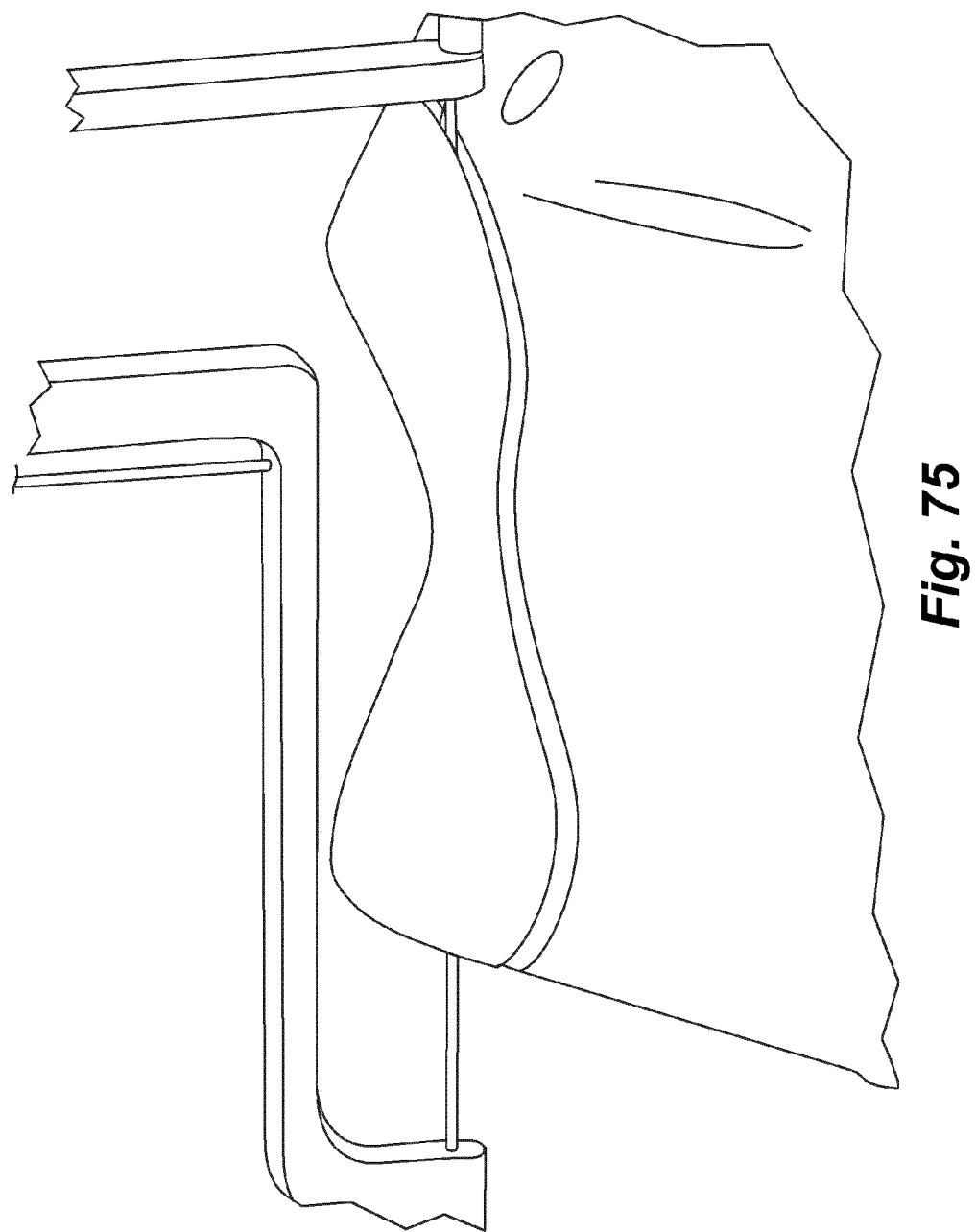
Figure 76:
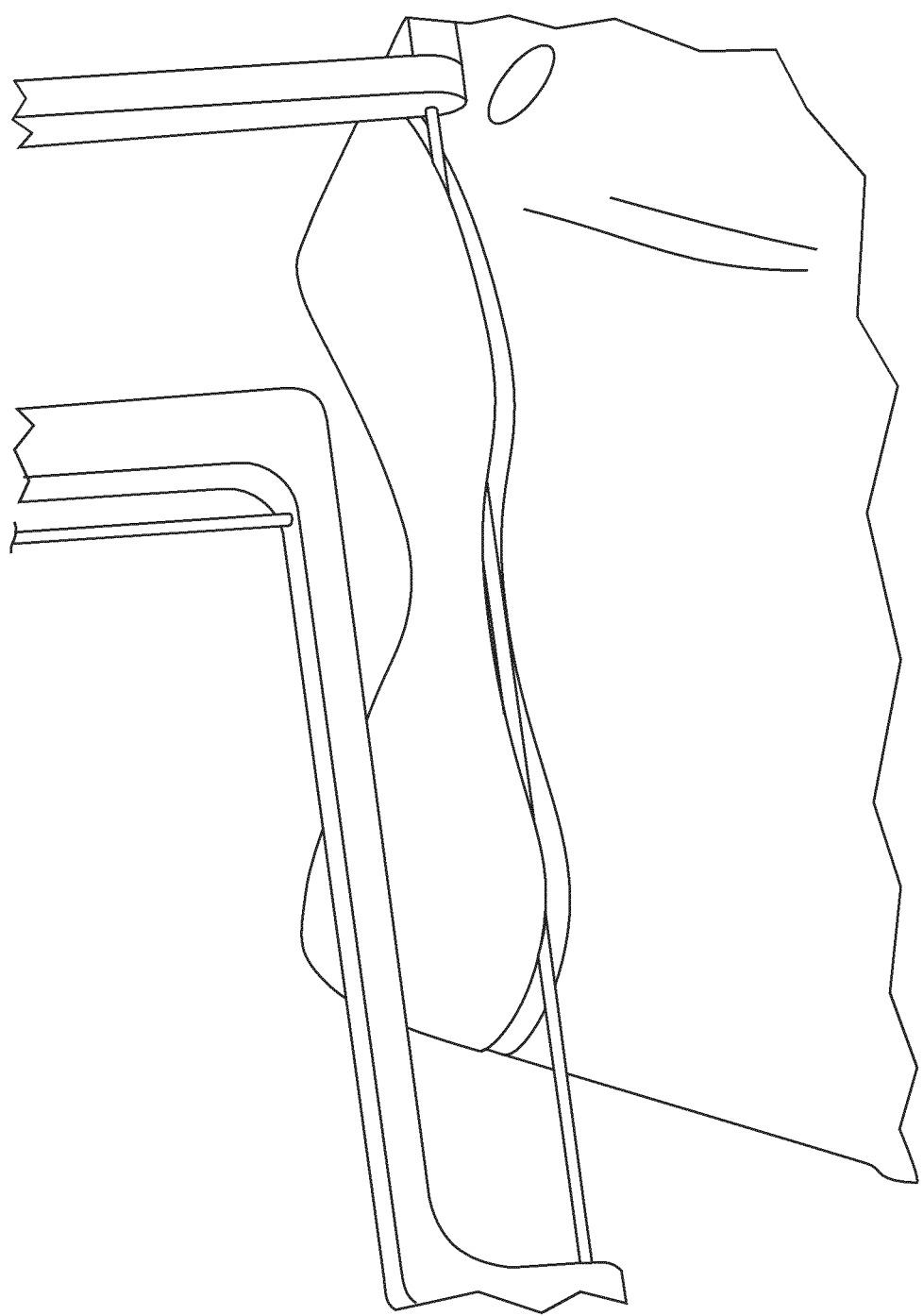

The handle and wire embodiments of the present invention in the embodiment shown in FIG. 47 are modified for use with the Sweeping Guide embodiments of the present invention shown in FIGS. 54-58. In essence, the Sweeping Guides comprise a pivot reference surface and pivot apertures noted in FIGS. 54 and 55 that are positioned and fixed in place appropriately with respect to the resected surfaces they are intended to create. The Wire Handle Pivot Axis feature represented in FIG. 53 is configured to engage the pivot apertures of the sweeping guide and a contact surface (not shown) on the handle engaged to the pivot reference surface of the sweeping guide. The resulting construct can then be manipulated by any combination of plunging, sweeping, and chopping movements (not shown) as shown in FIG. 58 to complete the desired bone cuts. As shown in comparing FIGS. 75 and 76, any of the embodiments of the present invention can be utilized in this manner. Given that the geometric relationships between the anterior cut and anterior chamfer cut with respect to their mutual vertex is consistent for many implant product lines across multiple or all sizes, a guide like that shown in FIG. 55 can provide guidance for all implant sizes' anterior and anterior chamfer cuts. Similarly, the guide shown in FIG. 56 can be universal to all implant sizes to complete the distal cut and/or distal chamfer cut and/or posterior cut.

Figure 59:
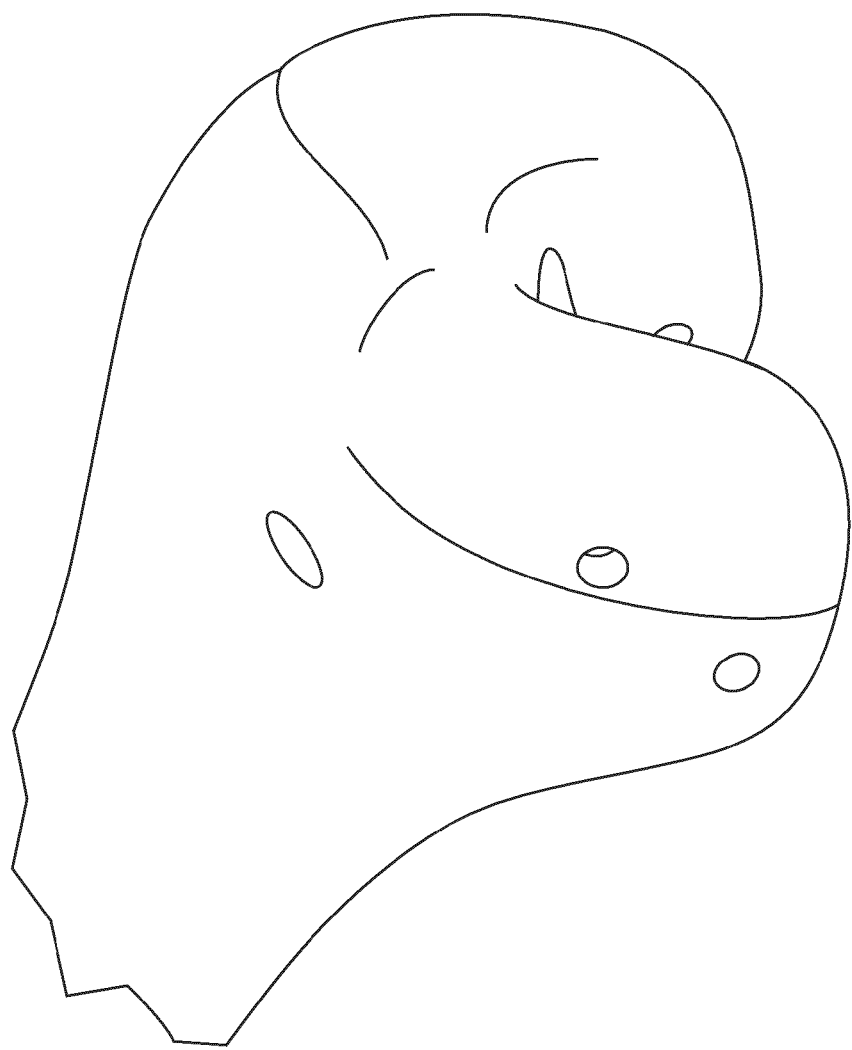

FIG. 59 shows apertures created in the bone for fixation of a single sweeping guide for creating all cut surfaces using a single guide construct with 5 pivot apertures and 5 pivot reference surfaces. Although three apertures in bone are shown, two round, or a single square aperture may also be utilized.

FIG. 60 shows an embodiment of the present invention wherein the guide plates and guide surfaces are located entirely outside the wound, but the wire and handle construct are not passed through mediolateral soft tissue portals described hereinabove. The wire controlling portion of the handle is essentially 'snaked' into the less invasive wound/exposure/approach/incision and the guide engagement features are engaged to the cutting guide at a location entirely outside the wound. As long as the axis of the engagement feature is maintained as coaxial with the wire, the desired cut geometries will be attained despite manipulation of the handle with respect to the guide. This method can be utilized to complete some or all of the desired cuts. Also, this embodiment of the present invention can be used to perform the posterior cut, posterior chamfer cut, and distal cut optionally using kinematic resection to reduce exposure requirements, and then removed from the wound and guide, flipped over 180 degrees from the orientation shown in FIG. 60, reinserted into the wound and engagement with the guide the anterior chamfer cut and anterior cut completed with or without implementation of a kinematic resection technique and, optionally, with the knee in 15 degrees to 45 degrees to facilitate the soft tissue laxity and ease of use hereinbefore described.

Figure 61:
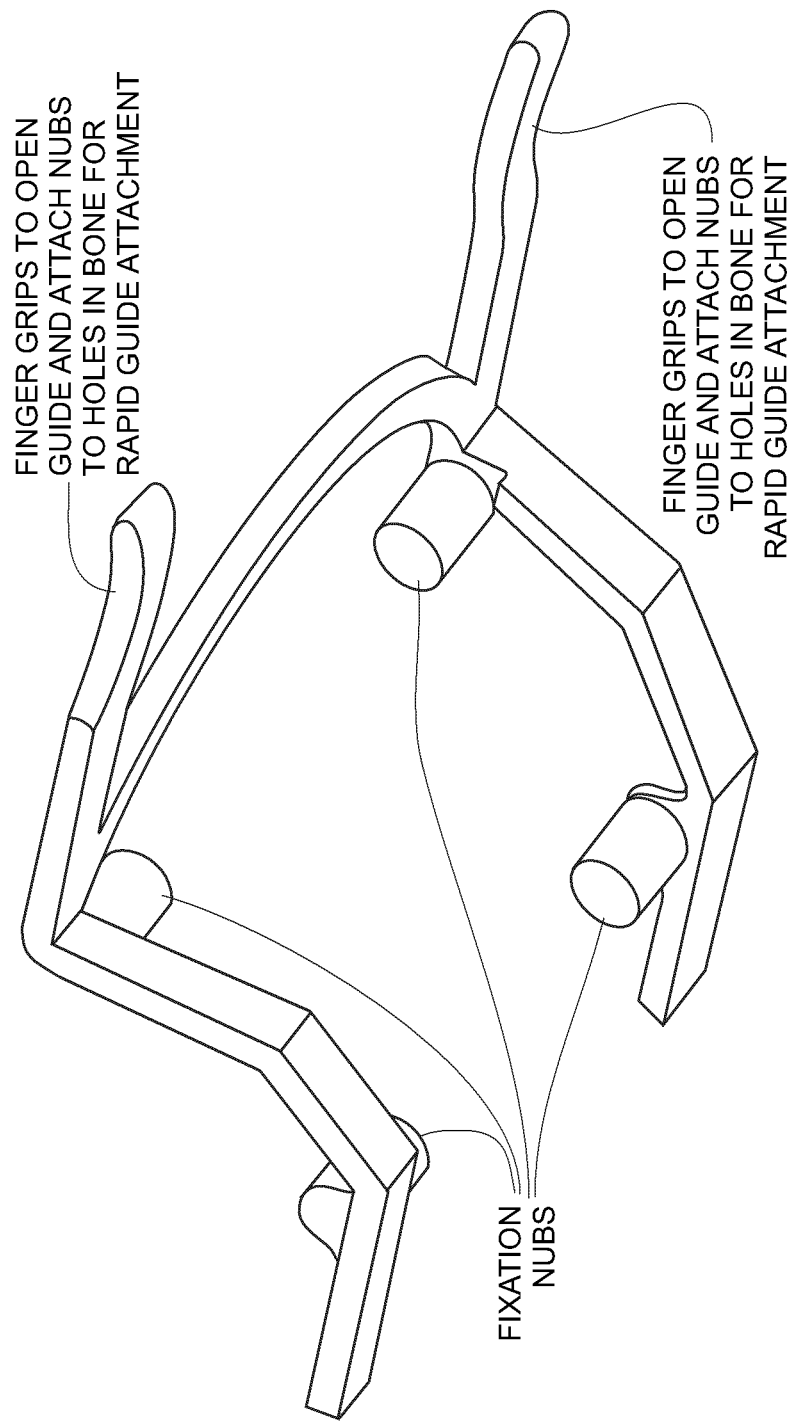
Figure 62:
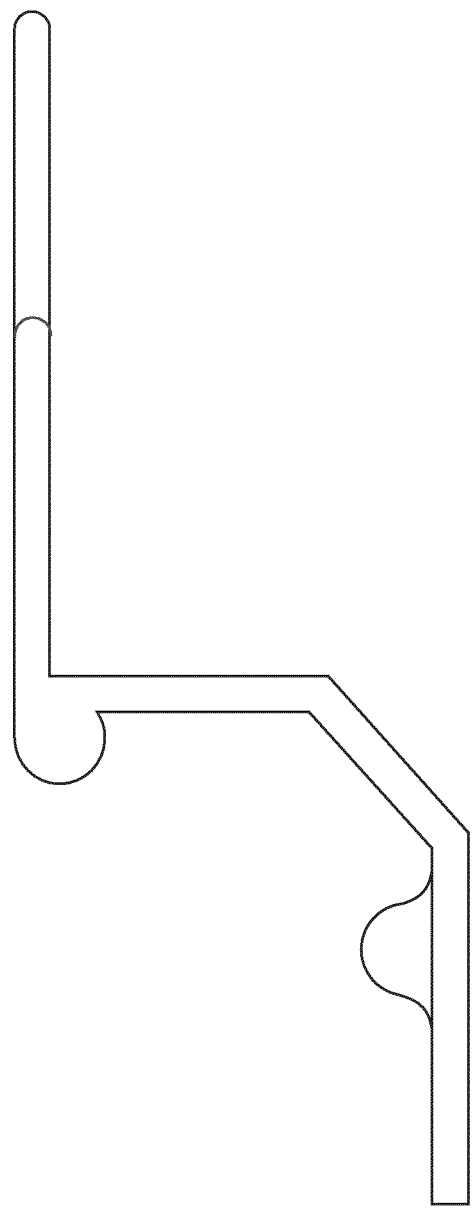
Figure 63:
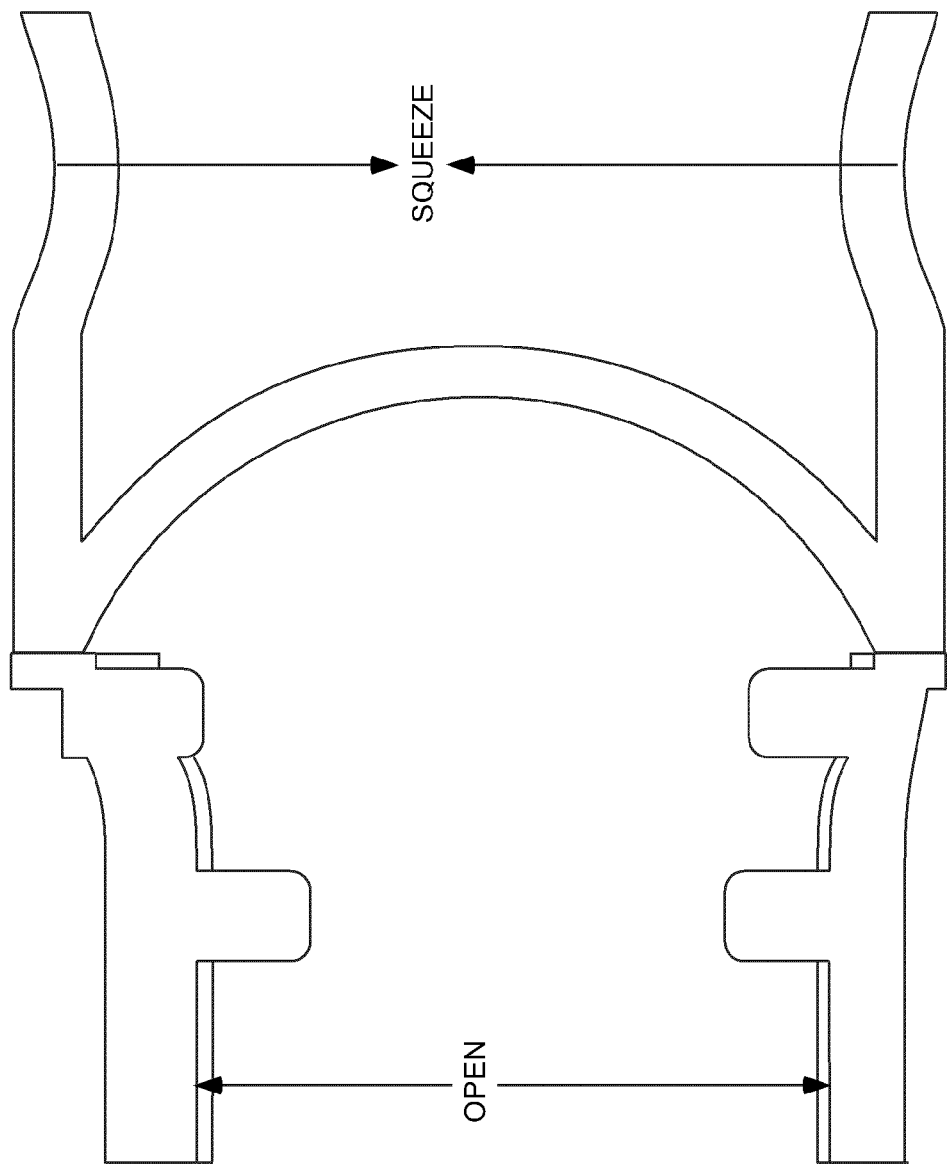
Figure 64:
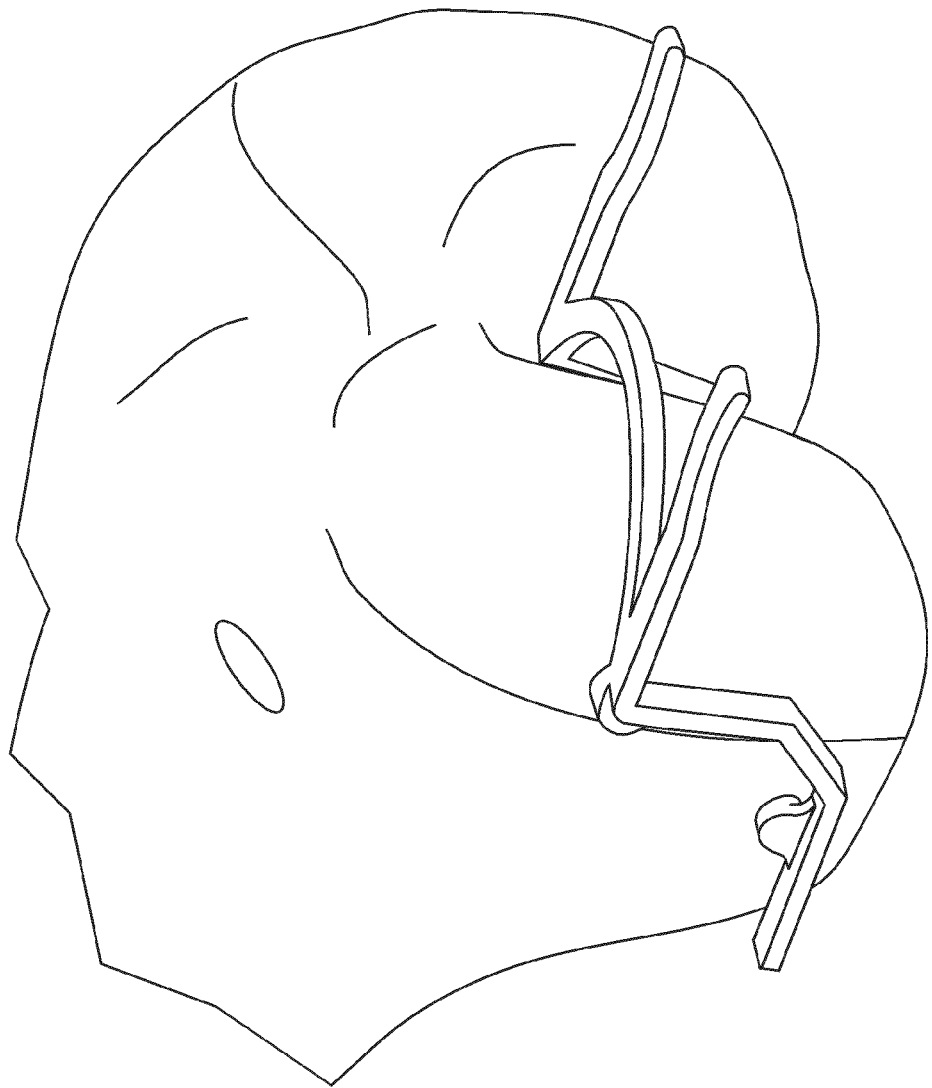
Figure 65:
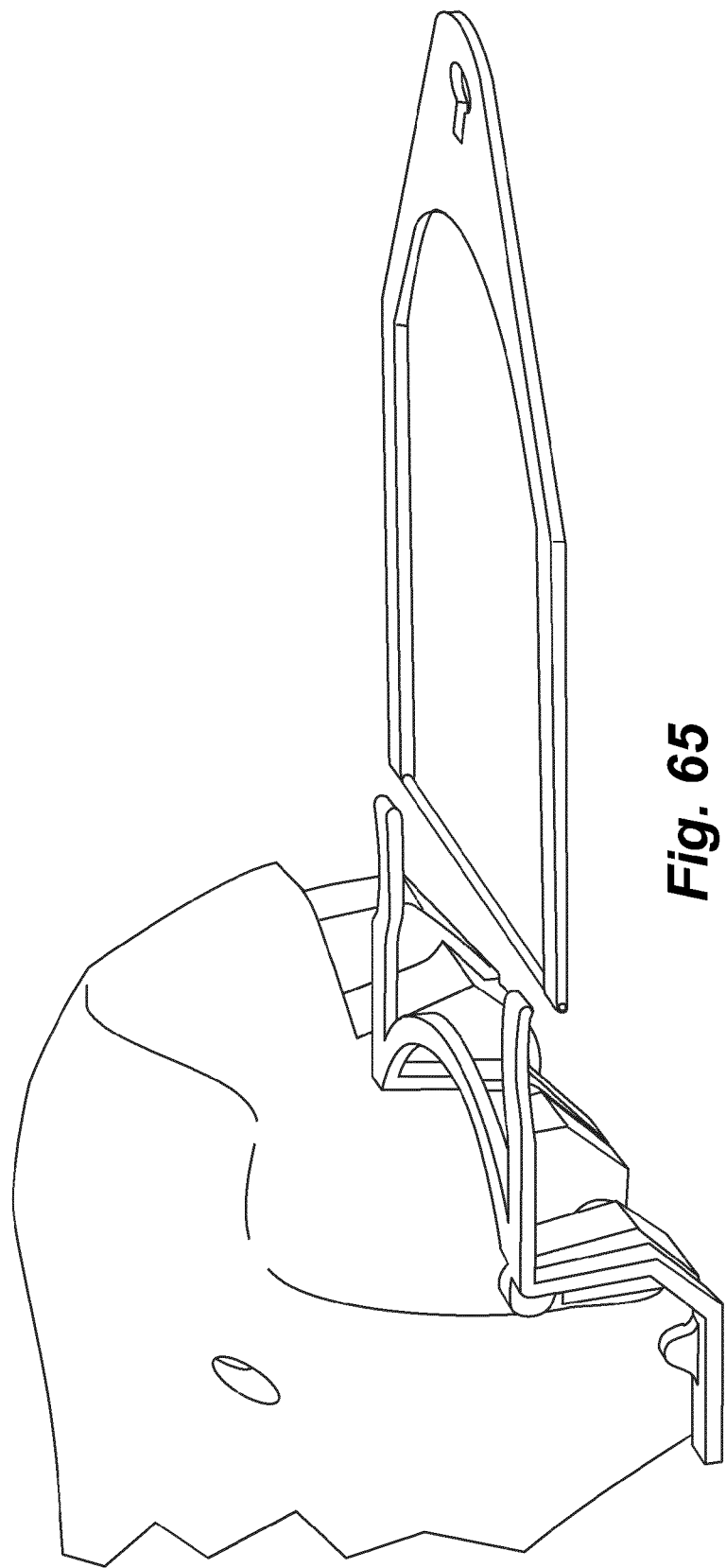
Figure 67:
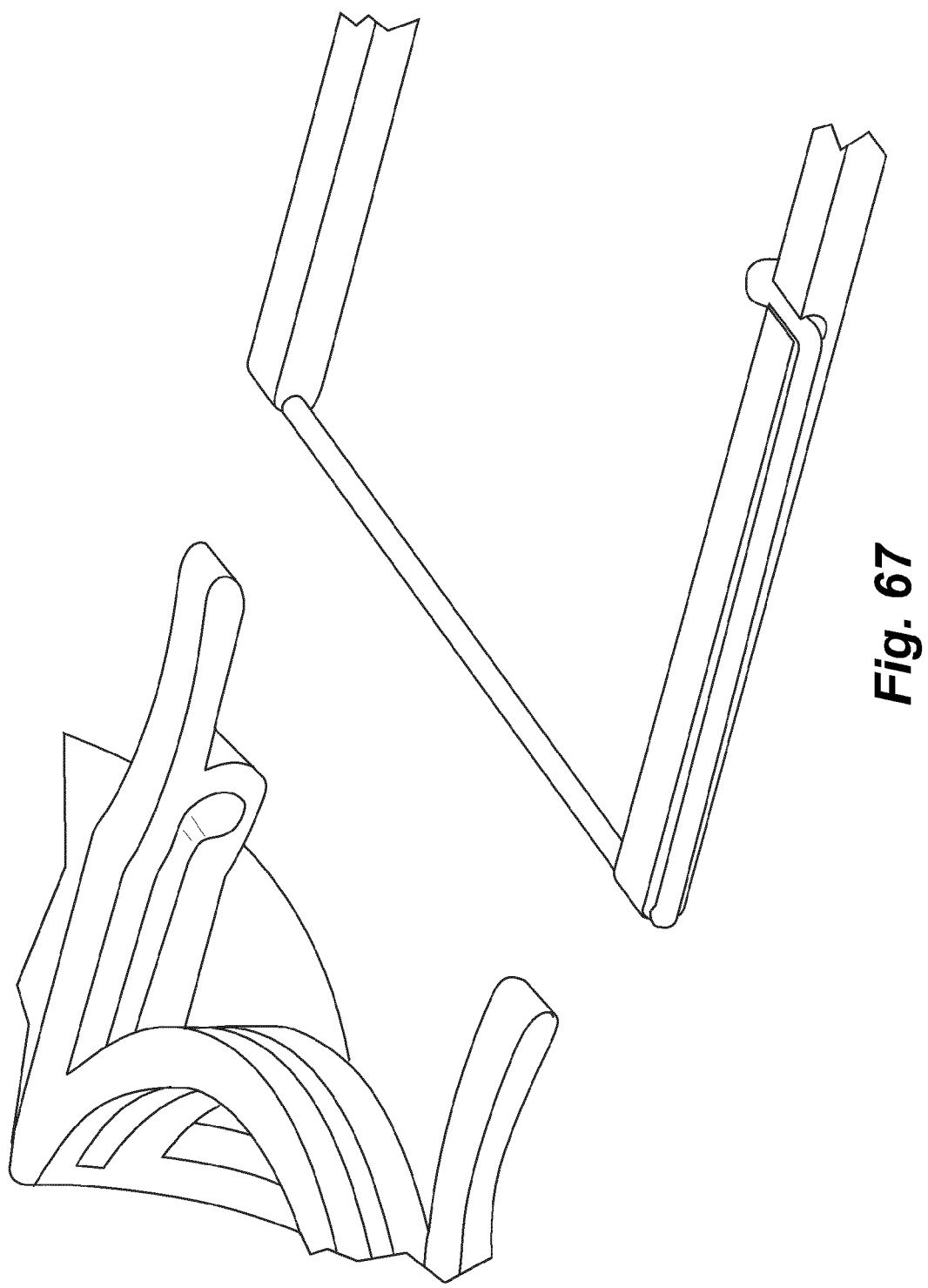
Figure 68:
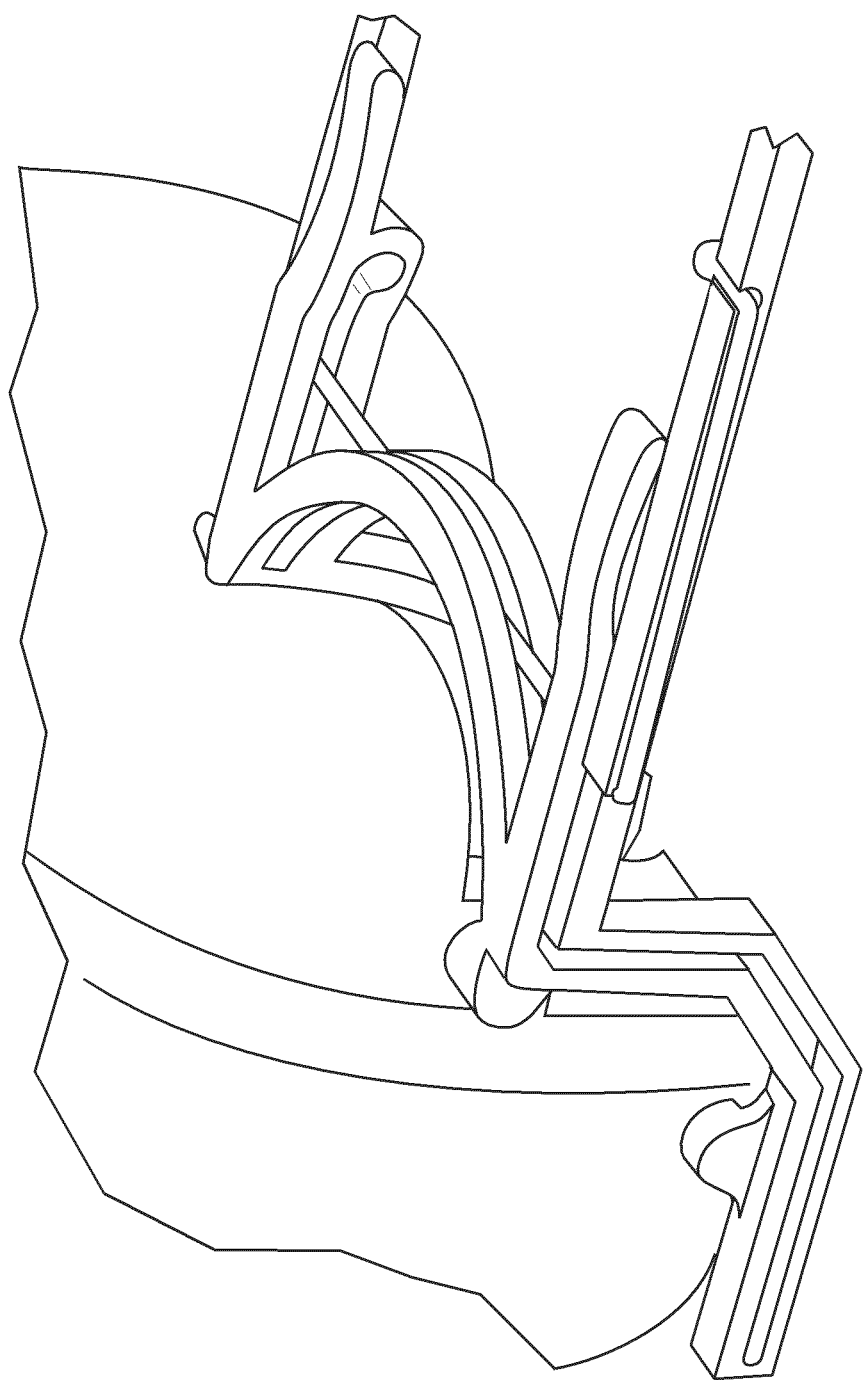
Figure 69:
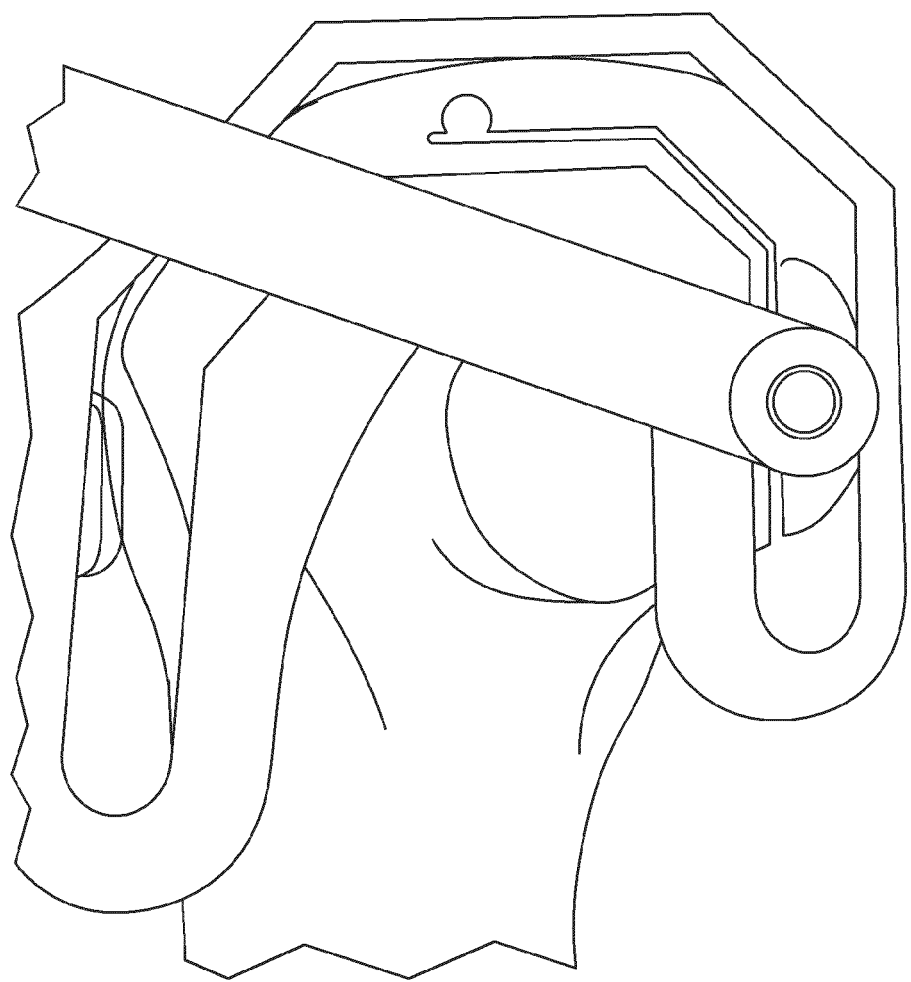
Figure 70:
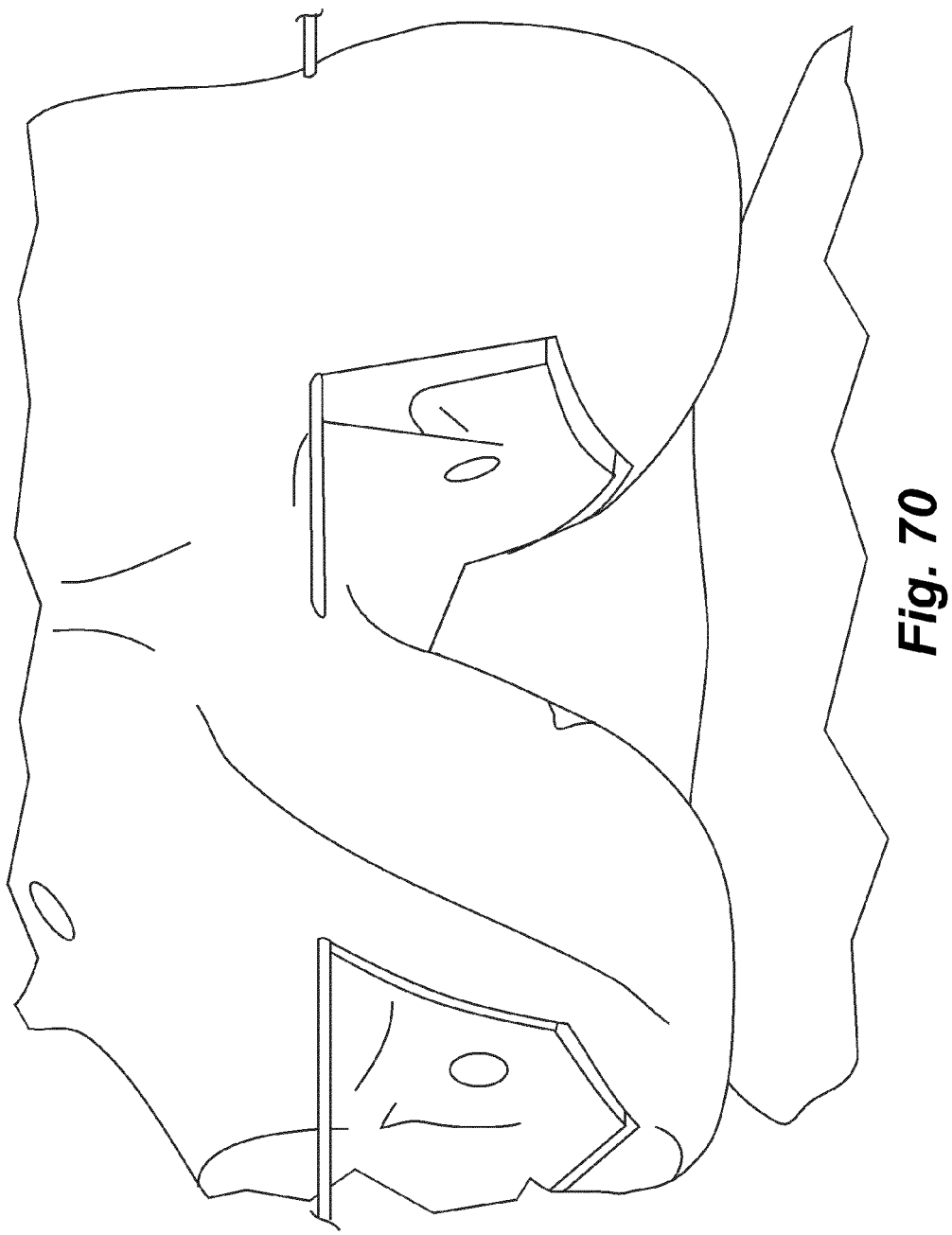

FIGS. 61-68 show an embodiment of the present invention for use in either Unicondylar, Tricompartmental, or Bicompartmental knee arthroplasty. The wire in this embodiment is adapted to be driven by an oscillating saw driver and the wire preferably is formed as a permanent part of the 'saw' as shown in FIG. 65 where the wire is shown in orange, or in an embodiment allowing the wire to be fished through a slot as shown in FIGS. 66-68 and attached to the opposing arm of the saw as shown. The guide of this embodiment of the present invention also contains little finger grips enabling a surgeon to attach the cutting guide to bone about as easily, and in a similar manner to the act of securing separate pieces of paper with a "binder clip" as represented in FIGS. 61, 63 and 64. This allows an oscillating saw driver to be used to cut the continuous and non-colinear cutting path of the cut surfaces shown or continuous and curvilinear cuts while being continuously manipulated along the cutting path of the guides without necessarily being removed from contact with the guide or bone during the process of cutting.

Figure 74:
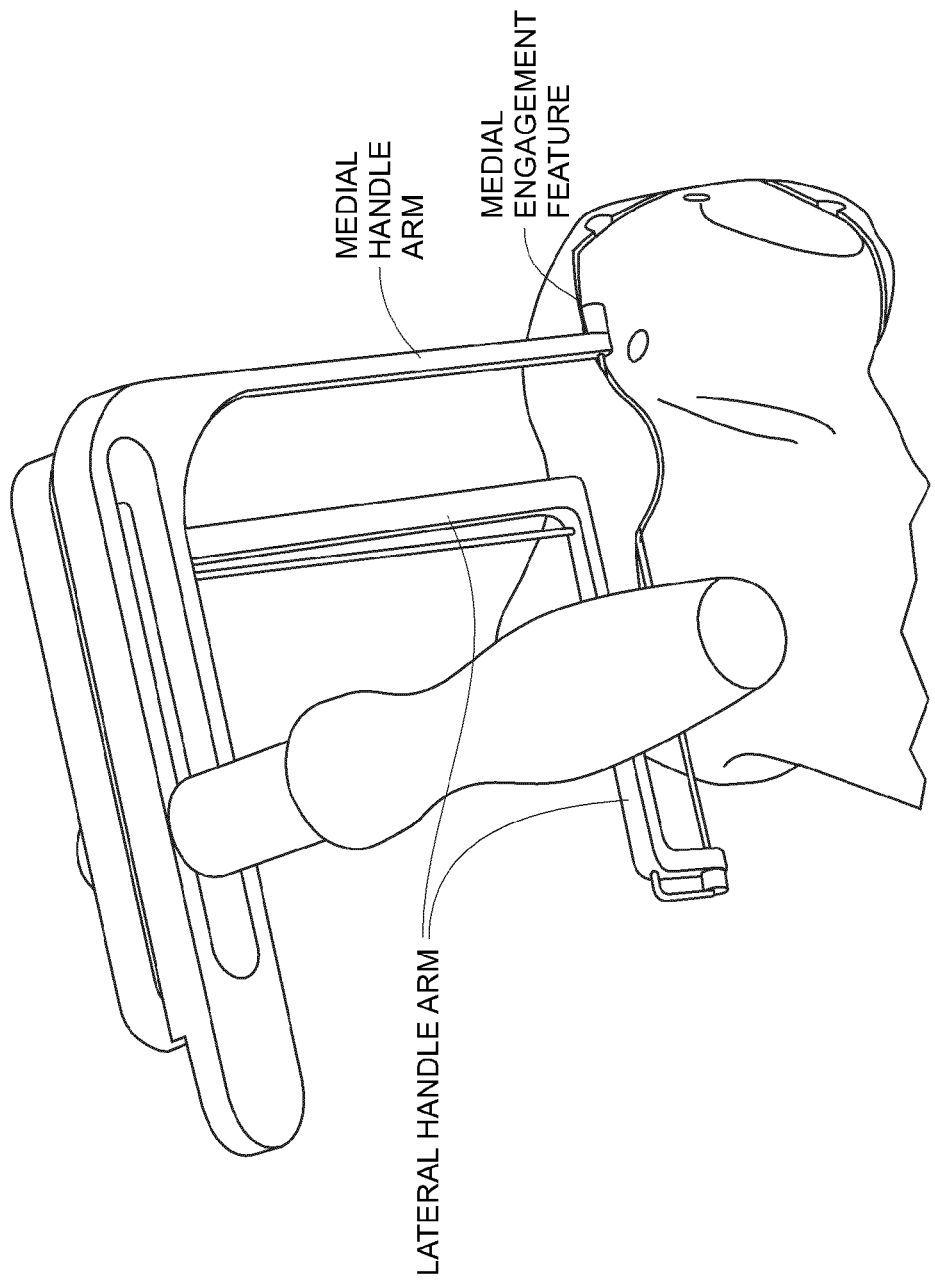

FIG. 74 demonstrates an embodiment of the present invention wherein the handle arm is utilized as an engagement feature for engagement to a cutting guide engagement or guide feature and used to guide the wire to create the cut surface. Using the handle arm in this manner in conjunction with the medial engagement feature shown in FIG. 74 is also an option. In this manner, the wire is manipulated in any manner known in the art including plunging, chopping, and/or sweeping motions while the handle arms open and close to adjust the effective length of the wire available to cut bone thus minimizing the potential for contact between the wire and soft tissue and reducing the incision size necessary to utilize the embodiments of the present invention. Specifically, the end of the lateral handle arm from which the wire emerges can be used to trace the boundary of the cut surface being created (similar to the method described for the devices in FIGS. 22-31) when the engagement feature is located to the medial side of the boundary. This approach may also be applied to individual condyles in either TKA, UKA, or bicompartmental procedures. Alternatively, the engagement feature(s) of the cutting guide can be located above the surface to be created instead of being located completely to the side of the boundary. In other words, the cutting guide can include a cylindrical aperture whose long axis is roughly normal to a planar surface to be created and a slit cut along its length to accommodate the wire during insertion and a window roughly normal to the slit through which the wire extends during cutting, where the medial handle arm is also cylindrical in cross-section to enable smooth articulation with the cylindrical aperture of the cutting guide during cutting. The cylindrical aperture's long axis can be normal or parallel to the plane being cut, and it can be located over or alongside the boundary of all the cuts being made or just an individual resected surface.

It should be noted that, in many of the figures, the cut surface created by the cutting tool in accordance with the technique of the present invention are shown as having already been completed for the sake of clarity. Similarly, the bones or apparatuses may be shown as being transparent or translucent for the sake of clarity. The guides/pins, cutting tool, bones, and other items disclosed are may be similarly represented for the sake of clarity or brevity.

Tibial resection in TKA can be somewhat frustrating to a certain percentage of orthopedic surgeons. This frustration appears to stem from the high demands upon the surgeon's manual skills or craftsmanship. The forms of the present invention help alleviate this issue by providing positive guidance of the cutting tool throughout all or most of the cutting process. Also, it should be noted that the various embodiments of the present invention allow for implementation with very small incisions.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed is:

1. An apparatus for preparing a knee bone to receive a knee arthroplasty implant fixation surface comprising:
    an elongated flexible cutting element adapted to cut the knee bone;
    a handle having a first structure defining an opening and a second structure defining an opening, each defined proximate a distal portion of the handle and the elongated flexible cutting element is tensioned such that the cutting element presents a thin cutting profile between the first structure and the second structure that is exposed to and moved along the bone to create a resected surface to which the knee arthroplasty implant fixation surface can be attached, and wherein the first structure and the second structure are selectively movable relative to one another such that a length of the thin cutting profile dynamically changes in response to a contour of a bone as the resected surface is created.

2. The apparatus of claim 1, further comprising means for energizing the cutting element by mechanical energy in the form of a unidirectional rotation of the cutting element.

3. The apparatus of claim 1, further comprising means for providing a mechanical vibration of the cutting element.

4. The apparatus of claim 1, wherein the handle is configured to permit at least the distal portion to be inserted into a minimally invasive surgical opening.

5. The apparatus of claim 1, wherein a volumetric displacement of bone per unit cutting length of the thin cutting profile is less than or equal to about 0.2in2 per inch cutting length.

6. The apparatus of claim 1, further comprising means for providing an oscillating movement of the cutting element.

7. The apparatus of claim 1, further comprising a spring adapted to maintain tension in the cutting element as the first structure and second structure are selectively moved relative to each other.

8. The apparatus of claim 1, wherein a remainder of the cutting element that does not define the thin cutting profile is disposed around fixtures on the handle.

9. The apparatus of claim 1, wherein a remainder of the cutting element that does not define the thin cutting profile is internally threaded through the handle.

10. The apparatus of claim 1, further comprising a soft tissue protective sleeve encircling the cutting element along the thin cutting profile adjacent each of the first structure and second structure, the soft tissue protective sleeves adapted to prevent the thin cutting profile from being exposed to soft tissue regions adjacent the knee bone and biased into contact with the knee bone.

11. The apparatus of claim 1, further comprising a pair of wire guards adapted to prevent contact between an operator and the cutting element.

12. A method of implanting an orthopedic prosthesis during knee arthroplasty surgery, comprising:
providing a prosthesis having a fixation surface for attachment to a knee bone and an articulation surface adapted to articulate with a surface of an adjacent bone; creating a resected surface on the knee bone to which the fixation surface of the prosthesis can be attached with a cutting tool having an elongated flexible cutting element tensioned to define a thin cutting profile between a first structure defining an opening and a second structure defining an opening, each defined proximate a distal portion of the cutting tool, the step of creating a resected surface including exposing and moving the cutting element along the knee bone such that the first structure and the second structure selectively move relative to one another to dynamically change a length of the cutting profile as the resected surface is created; and
operably attaching the prosthesis to the bone.

13. The method of claim 12, wherein the step of creating a resected surface includes energizing the cutting element by mechanical energy in the form of a unidirectional rotation of the cutting element.

14. The method of claim 12, wherein the step of creating a resected surface includes providing a mechanical vibration of the cutting element.

15. The method of claim 12, wherein the step of creating a resected surface includes providing an oscillating movement of the cutting element.

16. The method of claim 12, further comprising creating a minimally invasive surgical opening in soft tissue adjacent the knee bone and the step of creating a resected surface includes inserting the distal portion of the cutting tool through the minimally invasive surgical opening.

17. The method of claim 12, wherein the step of creating a resected surface includes preventing the cutting profile of the cutting tool from being exposed to soft tissue regions adjacent respective sides of the knee bone with a pair of soft tissue protective sleeves, each soft tissue protective sleeve surrounding the cutting profile proximate one of the soft tissue regions and biased to track along a contour of one of the sides of the knee bone.

18. An apparatus for preparing a knee bone to receive a knee arthroplasty implant fixation surface comprising;
an elongated flexible cutting element adapted to cut the knee bone;
a handle having a first structure defining an opening and second structure defining an opening each defined proximate a distal portion of the handle between which the elongated flexible cutting element is tensioned such that the cutting element presents a thin cutting profile between the first structure and second structure that is exposed to and moved along the bone to create a resected surface to which the knee arthroplasty implant fixation surface can be attached, wherein the first structure and the second structure are selectively movable relative to one another such that a length of the thin cutting profile dynamically changes in response to a contour of a bone as the implant fixation surface is created; and
a capstan drive system connected to the cutting element and adapted to maintain tension in the cutting element and impart a driving force to the cutting element to allow it to create the resected surface.

19. The apparatus of claim 18, wherein the capstan drive system includes a spring for maintaining tension in the cutting element.

20. The apparatus of claim 18, wherein the handle is configured to permit at least the distal portion to be inserted into a minimally invasive surgical opening.

* * * * *